US011572334B2

(12) United States Patent
Quay et al.

(10) Patent No.: US 11,572,334 B2
(45) Date of Patent: Feb. 7, 2023

(54) METHODS FOR MAKING AND USING ENDOXIFEN

(71) Applicant: Atossa Therapeutics, Inc., Seattle, WA (US)

(72) Inventors: Steven C. Quay, Seattle, WA (US); Yao-Lin Sun, Tainan (TW); LungHu Wang, Kaohsiung (TW); ChangJung Wu, Kaohsiung (TW); ChuanDer Huang, Tainan (TW)

(73) Assignee: ATOSSA THERAPEUTICS, INC., Seattle, WA (US)

( * ) Notice: Subject to any disclaimer, the term of this patent is extended or adjusted under 35 U.S.C. 154(b) by 0 days.

(21) Appl. No.: 17/580,428

(22) Filed: Jan. 20, 2022

(65) Prior Publication Data

US 2022/0242816 A1 Aug. 4, 2022

Related U.S. Application Data

(63) Continuation of application No. 16/641,985, filed as application No. PCT/US2018/050272 on Sep. 10, 2018, now Pat. No. 11,261,151.

(60) Provisional application No. 62/693,885, filed on Jul. 3, 2018, provisional application No. 62/624,787, filed on Jan. 31, 2018, provisional application No. 62/556,884, filed on Sep. 11, 2017, provisional application No. 62/556,799, filed on Sep. 11, 2017.

(51) Int. Cl.
| *A61K 31/135* | (2006.01) |
| *C07C 217/18* | (2006.01) |
| *C07C 213/10* | (2006.01) |
| *A61K 9/00* | (2006.01) |
| *A61K 45/06* | (2006.01) |

(52) U.S. Cl.
CPC .......... *C07C 217/18* (2013.01); *C07C 213/10* (2013.01); *A61K 9/0053* (2013.01); *A61K 45/06* (2013.01); *C07B 2200/13* (2013.01)

(58) Field of Classification Search
CPC .................................................... A61K 31/135
USPC ....................................................... 514/648
See application file for complete search history.

(56) References Cited

U.S. PATENT DOCUMENTS

| 3,848,030 | A | 11/1974 | Viterbo et al. |
| 4,851,433 | A | 7/1989 | Kraus |
| 6,774,122 | B2 | 8/2004 | Evans et al. |
| 7,384,418 | B2 | 6/2008 | Hung et al. |
| 7,485,623 | B2 | 2/2009 | Bua |
| 7,507,769 | B2 | 3/2009 | Nestour |
| 7,531,578 | B2 | 5/2009 | Forman et al. |
| 7,704,516 | B2 | 4/2010 | Drouin et al. |
| 7,705,159 | B2 | 4/2010 | Macdonald et al. |
| 7,786,172 | B2 | 8/2010 | De et al. |
| 7,968,532 | B2 | 6/2011 | Le et al. |
| 8,048,927 | B2 | 11/2011 | Le Nestour |
| 8,058,302 | B2 | 11/2011 | Solanki et al. |
| 8,063,249 | B1 | 11/2011 | Kushner et al. |
| 8,119,695 | B2 | 2/2012 | Forman et al. |
| 8,329,680 | B2 | 12/2012 | Evans et al. |
| 8,436,029 | B2 | 5/2013 | Hickey et al. |
| 8,454,945 | B2 | 6/2013 | McCook et al. |
| 8,466,139 | B2 | 6/2013 | Evans et al. |
| 8,822,511 | B2 | 9/2014 | Combs et al. |
| 8,993,605 | B2 | 3/2015 | Combs et al. |
| 9,073,875 | B2 | 7/2015 | Boyall et al. |
| 9,090,640 | B2 | 7/2015 | Bierbach et al. |
| 9,200,045 | B2 | 12/2015 | Liu et al. |
| 9,220,680 | B2 | 12/2015 | Perumal et al. |
| 9,308,181 | B2 | 4/2016 | Kisak et al. |
| 9,333,190 | B2 | 5/2016 | Ahmad et al. |
| 11,261,151 | B2 * | 3/2022 | Quay .................... C07C 217/18 |
| 2002/0025543 | A1 | 2/2002 | Serrero |
| 2003/0021787 | A1 | 1/2003 | Hung et al. |
| 2003/0099694 | A1 | 5/2003 | Cevc et al. |
| 2004/0092894 | A1 | 5/2004 | Hung et al. |
| 2007/0059288 | A1 | 3/2007 | Dinsmore et al. |
| 2007/0161063 | A1 | 7/2007 | Love et al. |
| 2007/0190019 | A1 | 8/2007 | Guo et al. |
| 2008/0138391 | A1 | 6/2008 | Carrara et al. |
| 2008/0319092 | A1 | 12/2008 | Singh |
| 2009/0068190 | A1 | 3/2009 | Bortz |
| 2009/0098069 | A1 | 4/2009 | Vacca |
| 2009/0208944 | A1 | 8/2009 | Goetz et al. |
| 2009/0281063 | A1 | 11/2009 | Inagi et al. |
| 2009/0291102 | A1 | 11/2009 | Fortin |
| 2009/0291134 | A1 | 11/2009 | Ahmad et al. |

(Continued)

FOREIGN PATENT DOCUMENTS

| CN | 101891635 A | 11/2010 |
| CN | 102448467 A | 5/2012 |
| CN | 104203961 A | 12/2014 |
| CN | 104352504 A | 2/2015 |

(Continued)

OTHER PUBLICATIONS

Ahamad A., et al., "Endoxifen, A New Cornerstone of Breast Cancer Therapy: Demonstration of Safety, Tolerability and Systemic Bioavailability in Healthy Human Subjects," Clinical Pharmacology & Therapeutics, Dec. 2010, vol. 88 (6), pp. 814-817.

(Continued)

*Primary Examiner* — Raymond J Henley, III

(74) *Attorney, Agent, or Firm* — DLA Piper LLP

(57) ABSTRACT

The present disclosure provides industrially scalable methods of making (Z)-endoxifen or a salt thereof, crystalline forms of endoxifin, and compositions comprising them. The present disclosure also provides methods for treating hormone-dependent breast and hormone-dependent reproductive tract disorders.

22 Claims, 13 Drawing Sheets

(56) References Cited

U.S. PATENT DOCUMENTS

| | | |
|---|---|---|
| 2010/0015195 A1 | 1/2010 | Jain et al. |
| 2010/0015200 A1 | 1/2010 | McClain et al. |
| 2010/0069781 A1 | 3/2010 | Johansen et al. |
| 2010/0098659 A1 | 4/2010 | Watson et al. |
| 2010/0112041 A1 | 5/2010 | Ahmad et al. |
| 2012/0010245 A1 | 1/2012 | Masini-Eteve |
| 2012/0149761 A1 | 6/2012 | Quay |
| 2012/0164075 A1 | 6/2012 | Ahmad et al. |
| 2012/0301541 A1 | 11/2012 | Haronsky et al. |
| 2013/0046171 A1 | 2/2013 | Johansen et al. |
| 2013/0177590 A1 | 7/2013 | Combs et al. |
| 2013/0197087 A1 | 8/2013 | Schlotzer et al. |
| 2014/0088059 A1 | 3/2014 | Perumal et al. |
| 2014/0193334 A1 | 7/2014 | Bierbach et al. |
| 2014/0199391 A1 | 7/2014 | Birbara |
| 2015/0080339 A1 | 3/2015 | Wang et al. |
| 2015/0132388 A1 | 5/2015 | Angi et al. |
| 2015/0141391 A1 | 5/2015 | Chinnaiyan et al. |
| 2015/0250802 A1 | 9/2015 | Labrie et al. |
| 2016/0346230 A1 | 12/2016 | Ahmad et al. |
| 2016/0375234 A1 | 12/2016 | Quay |
| 2017/0145515 A1 | 5/2017 | Chen et al. |
| 2017/0304232 A1 | 10/2017 | Khan et al. |
| 2018/0049999 A1 | 2/2018 | Quay |
| 2018/0200206 A1 | 7/2018 | Quay |
| 2019/0269697 A1 | 9/2019 | Labrie |
| 2020/0207704 A1 | 7/2020 | Quay et al. |

FOREIGN PATENT DOCUMENTS

| | | |
|---|---|---|
| CN | 105579044 A | 5/2016 |
| CN | 104230723 B | 8/2016 |
| EP | 2350111 A1 | 8/2011 |
| EP | 1709062 B9 | 2/2013 |
| EP | 3202420 A1 | 8/2017 |
| EP | 3202420 B1 | 3/2020 |
| WO | WO-0064416 A3 | 3/2001 |
| WO | WO-0174366 A1 | 10/2001 |
| WO | WO-2008070463 A2 | 6/2008 |
| WO | WO-2008070463 A9 | 9/2008 |
| WO | WO-2009032699 A1 | 3/2009 |
| WO | WO-2009069140 A1 | 6/2009 |
| WO | WO-2009120999 A2 | 10/2009 |
| WO | WO-2009120999 A3 | 12/2009 |
| WO | WO-2010066810 A1 | 6/2010 |
| WO | WO-2010135703 A2 | 11/2010 |
| WO | WO-2011072244 A1 | 6/2011 |
| WO | WO-2012050263 A1 | 4/2012 |
| WO | WO-2013050280 A1 | 4/2013 |
| WO | WO-2013134230 A1 | 9/2013 |
| WO | WO-2014134165 A1 | 9/2014 |
| WO | WO-2014141292 A2 | 9/2014 |
| WO | WO-2014060640 A8 | 5/2015 |
| WO | WO-2015106094 A1 | 7/2015 |
| WO | WO-2015138340 A1 | 9/2015 |
| WO | WO-2015187727 A2 | 12/2015 |
| WO | WO-2016168021 A1 | 10/2016 |
| WO | WO-2017011623 A1 | 1/2017 |
| WO | WO-2017070651 A1 | 4/2017 |
| WO | WO-2017080770 A1 | 5/2017 |
| WO | WO-2019051368 A1 | 3/2019 |
| WO | WO-2019051370 A1 | 3/2019 |
| WO | WO-2019051416 A1 | 3/2019 |

OTHER PUBLICATIONS

Ahmad A., et al., "Endoxifen, A New Treatment Option for Mania: A Double-Blind, Active-Controlled Trial Demonstrates the Antimanic Efficacy of Endoxifen," Clinical and Translational Science, vol. 9 (5), Oct. 2016, pp. 252-259.

Ahmad A., et al., "Endoxifen for Breast Cancer: Multiple Dose, Dose Escalation Study Characterizing Pharmacokinetics and Safety in Metastatic Breast Cancer Patients," Journal of Clinical Oncology, vol. 30 (15), May 20, 2012, Abstarct 3089, 3 pages.

Ahmad A., et al., "Orally Administered Endoxifen is a New Therapeutic Agent for Breast Cancer," Breast Cancer Research Treatment, vol. 122 (2), Jul. 2010, pp. 579-584.

Aydiner, et al., "Meta-Analysis of Trials Comparing Anastrozole and Tamoxifen for Adjuvant Treatment of Oostmenopausal Women with Early Breast Cancer," Trials, vol. 9 (47), Jul. 29, 2008, pp. 1-9.

Bao, et al., "The Clinical Pharmacology of Anastrozole," European Oncology and Hematology, vol. 7 (2), 2011, pp. 106-108.

Bath, et al., "An Improved Sysnthesis of Raloxifene Hydrochoride: A Selective Estrogen Receptor Modulator," Heteroletters, vol. 4 (4), 2014, pp. 515-518.

Bernhard H., et al., "Adoptive Transfer of Autologous, HER2-Specific, Cytotoxic T Lymphocytes for the Treatment of HER2-Overexpressing Breast Cancer," Cancer Immunology, Immunotherapy, 2008, vol. 57, pp. 271-280.

Chang M., "Tamoxifen Resistance in Breast Cancer," Biomolecules Therapeutics, May 2012, vol. 20 (3), pp. 256-267.

Clinical Trials Government, Identifier No. NCT01273168, "Endoxifen in Adults With Hormone Receptor Positive Solid Tumors," Jan. 10, 2011, 10 pages.

Clinical Trials Government, Identifier No. NCT02311933, "Tamoxifen Citrate or Z-Endoxifen Hydrochloride in Treating Patients With Locally Advanced or Metastatic, Estrogen Receptor-Positive, HER2-Negative Breast Cancer," Dec. 9, 2014, 13 pages.

Davison, et al., "In Vitro Effects on MCF-7 Breast Cancer Cells of Signal Transduction Inhibitor/Tamoxifen/ Eicosapentaenoic Acid Combinations and their Simultaneous Delivery Across Skin," Pharmaceutical Research, vol. 25, 2008, pp. 2516-2525.

Dickschen K., et al., "Physiologically Based Pharmacokinetic Modeling of Tamoxifen and its Metabolites in Women of Different CYP2D6 Phenotypes Provides New Insight into the Tamoxifen Mass Balance," Frontiers in Pharmacology, vol. 3 (92), May 2012, 15 pages, www.frontiersin.org.

Donneyong M.M., et al., "Risk of Mortality with Concomitant use of Tamoxifen and Selective Serotonin Reuptake Inhibitors: Multi-Database Cohort Study," BMJ, Sep. 30, 2016, vol. 354 (i5014), 20 pages.

Dowsett, et al., "The Effect of Anastrozole on the Pharmacokinetics of Tamoxifen in Post-Menopausal Women with Early Breast Cancer," British Journal of Cancer, vol. 79 (2), 1999, pp. 311-315.

Extended European Search Report for European Application No. EP18853361.6, dated May 28, 2021, 5 pages.

Fauq A.H., et al., "A Convenient Synthesis of (Z)-4-Hydroxy-N-Desmethyltamoxifen (Endoxifen)," Bioorganic and Medicinal Chemistry Letters, vol. 20 (10), 2010, pp. 3036-3038.

Final Rejection for U.S. Appl. No. 16/641,985, dated Oct. 26, 2021, 9 pages.

Forbes, et al., "Anastrozole Versus Tamoxifen for the Prevention of Locoregional and Contralateral Breast Cancer in Postmenopausal Women with Locally Excised Ductal Carcinoma in Situ (IBIS-II DCIS): A Double-Blind," Randomised Controlled trial Lancet, vol. 387, 2016, pp. 866-873.

Forefront., "Endoxifen Shows Promise As Breast Cancer Treatment", Mayo Clinic Cancer Center's Online Magazine, vol. 3, Issue 1, 2014, 3 pages.

Galeana P.C., et al., "Ki67 Changes Identify Worse Outcomes in Residual Breast Cancer Tumors After Neoadjuvant Chemotherapy," The Oncologist, vol. 23 (6), Jun. 2018, pp. 670-678.

Gauthier S., et al., "New Highly Stereoselective Synthesis of (Z)-4-Hydroxytamoxifen and (Z)-4-Hydroxytoremifene via McMurry Reaction," The Journal of Organic Chemistry, vol. 61 (11), May 31, 1996, pp. 3890-3893.

Gelmon, et al., "Targeting Triple-Negative Breast Cancer: Optimizing Therapeutic Outcomes," Annals of Oncology, vol. 23 (9), Sep. 2012, pp. 2223-2234.

Goetz M.P., et al., "Abstract PD2-03: Final Results of a First-in-Human Phase I Study of the Tamoxifen (TAM) Metabolite, Z-Endoxifen Hydrochloride (Z-Endx) in Women with Aromatase Inhibitor (AI) Refractory Metastatic Breast Cancer (MBC) (NCT01327781)," San Antonio breast cancer symposium, Dec. 8-12, 2015, 5 pages.

Goetz M.P., et al., "Final Results of a First in Human Phase I Study of the Tamoxifen (TAM) Metabolite, Endoxifen Hydrochloride in

(56) References Cited

OTHER PUBLICATIONS

Women with Aromatase Inhibitor (AI) Refractory Metastatic Breast Cancer (MBC) (NCT01327781)," San Antonio Breast Conference, 2015, PD203, 1 page.

Goetz M.P., et al., "First-in-Human Phase I Study of the Tamoxifen Metabolite Z-Endoxifen in Women With Endocrine-Refractory Metastatic Breast Cancer," DOI: https://ascopubs.org/doi/10.1200/JCO. 2017.73.3246, vol. 35, No. 30, Oct. 20, 2017, 16 pages.

Hawse J.R., et al., "Endoxifen's Molecular Mechanisms of Action are Concentration Dependent and Different than that of other Anti-Estrogens," PLOS one, vol. 8 (1), Jan. 2013, e54613, 18 pages.

Henderson S.L., et al., "Profound Reduction in Tamoxifen Active Metabolite Endoxifen in a Breast Cancer Patient Treated with Rifampin Prior to Initiation of an Anti-TNF a Biologic for Ulcerative Colitis: a Case Report," BMC cancer, vol. 16 (304), May 11, 2016, 6 pages.

Hershman, et al., "Early Discontinuation and Non-adherence to Adjuvant Hormonal Therapy in a Cohort of 8, 769 early Stage Breast Cancer Patients," Journal of Clinical Oncology, vol. 26(27), Sep. 20, 2010.

Ikeda H., et al., "Combination Treatment with Fulvestrant and various Cytotoxic Agents (Doxorubicin, Paclitaxel, Docetaxel, Vinorelbine, and 5-Fluorouracil) has a Synergistic Effect in Estrogen Receptor-Positive Breast Cancer," Cancer Science, vol. 102 (11), Nov. 2011, pp. 2038-2042, 5 Pages.

Ingle, et al., "Variation in Anastrozole Metabolism and Pharmacodynamics in Women with Early Breast Cancer," Cancer Research, vol. 70 (8), Apr. 15, 2010, pp. 3278-3286.

International Preliminary Report on Patentability for the application No. PCT/US2020/040757, dated Jan. 13, 2022, 9 pages.

International Report on Patentability for International Application No. PCT/US2018/050193, dated Mar. 26, 2020, 7 pages.

Jansen, et al., "High miR-26a and Low CDC2 Levels Associate with Decreased EZH2 Expression and with Favorable Putcome on Tamoxifen in Metastatic Breast Cancer," Breast Cancer ResearchTreatment, vol. 133, 2012, pp. 937-947.

Johnson M.D., et al., "Pharmacological Characterization of 4-Hydroxy-N-Desmethyl Tamoxifen, A Novel Active Metabolite of Tamoxifen," Breast Cancer Research and Treatment, vol. 85, 2004, pp. 151-159.

Johnson R.E., et al., "Gynecomastia—Evaluation and Current Treatment Options," Therapeutics and Clinical Risk Management, vol. 7, 2011, pp. 145-148.

Jordan V.C., "New Insights into the Metabolism of Tamoxifen and its Role in the Treatment and Prevention of Breast Cancer," Steroids, vol. 72 (13), Nov. 2007, pp. 829-842.

Kamdem, et al., "In Vitro and in Vivo Oxidative Metabolism and Glucuronidation of Anastrozole," British Journal of Clinical Pharmacology, vol. 70 (6), 2010, pp. 854-869.

Karlsson H., et al., "CAR T-Cell Therapy: The Role of Physical Barriers and Immunosuppression in Lymphoma," Gene Ther, Aug. 2015, vol. 26(8), https://pubmed.ncbi.nlm.nih.gov/26230974/, pp. 498-505.

Kaur, et al., "Design, Synthesis and Evaluation of Ospemifene Analogs as Anti-Breast Cancer Agents," European Journal of Medicinal Chemistry, vol. 86, Oct. 30, 2014, pp. 211-218.

Kebamo., et al., "The Role of Biotransformation in Drug Discovery and Development," Journal of Drug Metabolism and Toxicology, vol. 6 (5), 2015, pp. 1-13.

Lancet, "Aromatase Inhibitors Versus Tamoxifen in Early Breast Cancer: Patient-Level Meta-Analysis of the Randomised Trials," vol. 386, 2015, pp. 1341-1352.

Lari, et al., "Biological Markers in DCIS and Risk of Breast Recurrence: A Systematic Review," Journal of Cancer, vol. 2, 2011, pp. 232-261.

Lazzeroni M., et al., "Oral Low Dose and Topical Tamoxifen for Breast Cancer Prevention: Modern Approaches for an Old Drug," Breast Cancer Research, vol. 14(214), 2012, 11 pages.

Lee O., et al., "In Vitro Human Skin Permeation of Endoxifen: Potential for Local Transdermal Therapy for Primary Prevention and Carcinoma in Situ of the Breast," Breast Cancer: Targets and Therapy, vol. 3, 2011, pp. 61-70.

Lee O., et al., "Local Transdermal Therapy to the Breast for Breast Cancer Prevention and DCIS Therapy: Preclinical and Clinical Evaluation," Cancer Chemother Pharmacol, vol. 76(6), Dec. 2015, pp. 1235-1246.

Lemaine, et al., "Gynecomastia in Adolescent Males," Seminars Plastic Surgery, vol. 27 (1), Feb. 2013, pp. 56-61.

Liby, et al., "The Combination of the Rexinoid, LG100268, and a Selective Estrogen Receptor Modulator, Either Arzoxifene or A colbifene, Synergizes in the Prevent and Treatment of Mammary Tumors in an Estrogen Receptor-Negative Model of Breast Cancer," Clinical Cancer Research, vol. 12 (19), Oct. 2006, pp. 5902-5909.

Mah, et al., "A Miniaturized Flow-through Cell to Evaluate Skin Permeation of Endoxifen," International Journal of pharmaceutics, vol. 441,2013, pp. 433-440.

Mahoney M.E., et al., "Intraductal Therapy of Ductal Carcinoma In Situ: A Presurgery Study," Clinical Breast Cancer, Aug. 2013, 13(4), pp. 280-286.

Manni, et al., "Combination of Antiestrogens and Omega-3 Fatty Acids for Breast Cancer Prevention," Biomed Research International, Jan. 1, 2015, 10 pages.

Mansel R., et al., "A Phase II Trial of Afimoxifene (4-hydroxyTamoxifen gel) for Cyclical Mastalgia in Premenopausal Women," Breast Cancer Research Treatment, Dec. 2007, vol. 106 (3), pp. 389-397.

Maximov P. Y., et al., "Structure-Function Relationships of Estrogenic Triphenylethylenes Related to Endoxifen and 4-Hydroxytamoxifen," Journal of Medicinal Chemistry, Apr. 22, 2010, vol. 53 (8), pp. 3273-3283.

Melnikow J., et al., "Preferences of Women Evaluating Risks of Tamoxifen (POWER) study of preferences for Tamoxifen for Breast Cancer Risk Reduction," Cancer, vol. 103 (10), May 15, 2005, pp. 1996-2005.

Memorial Sloan Kettering: "T-Cell Therapy for Advanced Breast Cancer," 2016, pp. 1-8.

Miller, et al., "Stereospecific Synthesis of (Z)-Tamoxifen via Carbometallation of Alkynylsilanes," The Journal of Organic Chemistry, vol. 50 (12), 1985, pp. 2121-2123.

Non-Final Office Action for U.S. Appl. No. 16/641,985 dated Sep. 7, 2021, 13 pages.

Notice of Allowance for U.S. Appl. No. 16/641,985 dated Nov. 17, 2021, 9 pages.

Ogawa K., et al., "Synthesis and Antiestrogenic Activity of the Compounds Related to the Metabolites of (Z)-4[1-[4-[2-(Dimethylamino)ethoxy]phenyl]-2-(4-isopropylphenyl)-1-butenyl]phenyl monophosphate (TAT-59)," Chemical and Pharmaceutical Bulletin, Apr. 1991, vol. 39(4), pp. 911-916.

Partridge, et al., "Adherence to Initial Adjuvant Anastrozole Therapy among Women with Early Stage Breast Cancer," Journal Clinical Oncology, Feb, 1, 2008, vol. 26 (4).

Partridge, et al., "Nonadherence to Adjuvant Tamoxifen Therapy in Women with Primary Breast Cancer," Journal of Clinical Oneology, Feb. 15, 2003, vol. 21.

Robertson, et al., "Fulvestrant: Pharmacokinetics and Pharmacology," British Journal of Cancer, 2004, vol. 90, pp. S7-S10.

Robertson, et al., "Pharmacokinetic Profile of Intramuscular Fulvestrant in Advanced Breast Cancer," Clinical Pharmacokinetics, 2004, vol. 43 (8), pp. 529-538.

Rouanet P., et al., "Neoadjuvant Percutaneous 4-Hydroxytamoxifen Decreases Breast Tumoral Cell Proliferation: A Prospective Controlled Randomized Study Comparing Three Doses of 4-hydroxytamoxifen Gel to Oral Tamoxifen," Journal of Clinical Oncology, May 1, 2005, vol. 23(13), pp. 2980-2987.

Sano, et al., "Short-step Synthesis of Droloxifene via the Three-Component Coupling Reaction among Aromatic Aldehyde, Cinnamyltrimethylsilane, and 13-Chlorophenetole," Tetrahedron Letters, Mar. 6, 2006, vol. 47 (10), pp. 1631-1635.

Stearns, et al., "Preclinical and Clinical Evaluation of Intraductally Administered Agents in Early Breast Cancer," Science Translational Medicine, Oct. 26, 2011, vol. 3 (106), 9 pages, 106ra108.

Umareddy, et al., "Improved Process for Centchroman, A Selective Estrogen Receptor Modulator (SERM)," Journal of Chemical and Pharmaceutical Research, 2015, vol. 7 (7), pp. 736-741.

(56) References Cited

OTHER PUBLICATIONS

Umareddy, et al., "Total Synthesis of Lasofoxifene and Nafoxidine," An International Journal for Rapid Communication of Synthetic Organic Chemistry, 2016, vol. 46 (4), pp. 309-313.

Vergote, et al., "Fulvestrant is an Effective and Well-Tolerated Endocrine Therapy for Postmenopausal Women with Advanced Breast Cancer," Results from Clinical Trials, British Journal of Cancer, 90 (Suppl), 2004, pp. S11-S14.

Welsh J., "Induction of Apoptosis in Breast Cancer Cells in Response to Vitamin D and Antiestrogens," Biochemistry and Cell Biology, 1994, vol. 72 (11-12), pp. 537-545.

Wu, et al., "Single Cell MicroRNA Analysis using Microfluidic Ftow Cytometry," PLOS One, 2013, vol. 8 (1), e55044.

Yan Yaodong., "Design and Development of Sustained-Release and Controlled-Release Formulations," Chinese Medicine Science and Technology Publishing House, Jun. 30, 2006 (Jun. 30, 2006), pp. 421-428.

Yang Y., et al., "Dendron-Based Micelles for Topical Delivery of Endoxifen: A Potential Chemo-Preventive Medicine for Breast Cancer," Advanced Functional Materials, 2014, vol. 24, pp. 2442-2449.

Yao, et al., "Synthesis and Reactivity of Potential Toxic Metabolites of Tamoxifen Analogues: Droloxifene and Toremifene a-Quinones," Chemical Research in Toxicology, 2001, vol. 14 (12), pp. 1643-1653.

Yoneya, et al., "Thiochroman Derivative CH4986399, A New Nonsteroidal Estrogen Receptor Down-regulator, Is effective in Breast Cancer Models," Anticancer Research, 2010, vol. 30, pp. 873-878.

Zhang B., et al., "The Safety Parameters of the Study on Intraductal Cytotoxic Agent Delivery to the Breast Before Mastectomy," http://dx.doi.org/10.3978/j.issn.1000-9604.2014.10.06, Sep. 9, 2014, Chinese Journal of Cancer Research, vol. 26(5), pp. 579-587.

Ackerman A.B., et al., "Contrary View: The Breast is not an Organ Per Se, but a Distinctive Region of Skin and Subcutaneous Tissue," The American Journal of Dermatopathology, Apr. 2007, vol. 29(2), pp. 211-218.

Anonymous, "History of Changes for Study: NCT02547961," Sep. 10, 2015, XP055669980, retrieved from the URL: https://clinicaltrials.gov/ct2/history/NCT02547961?V_1=View#StudyPageTop, on Feb. 19, 2020, 4 pages.

Bhatnagar P., et al., "Tumor Lysing Genetically Engineered T Cells Loaded with Multi-Modal Imaging Agents," Scientific Reports, vol. 4, No. 4502, DOI: 10.1038/srep04502, published on Mar. 28, 2014, 21 pages.

Extended European Search Report for EP Application EP17857260.8, dated Mar. 24, 2020, 16 pages.

Fasching P.A., et al., "Ki67, Chemotherapy Response and Prognosis in Breast Cancer Patients receiving Neoadjuvant Treatment," BMC Cancer, vol. 11, Article 486, 2011, 13 pages.

Goetz M.P., et al., "A First-in-Human Phase I Study of the Tamoxifen (TAM) Metabolite, Z-Endoxifen Hydrochloride (Z-Endx) in Women with Aromatase Inhibitor (AI) Refractory Metastatic Breast Cancer (MBC) (NCT01327781)," San Antonio Breast Conference, Dec. 2013, PD3-4, 4 pages.

International Search Report and Written Opinion for International Application No. PCT/US2018/050193, dated Jan. 4, 2019, 9 pages.

International Search Report and Written Opinion for International Application No. PCT/US2018/050272, dated Jan. 3, 2019, 12 pages.

Li L., et al., "Prognostic Values of Ki-67 in Neoadjuvant Setting for Breast Cancer: A Systematic Review and Meta-Analysis," Future Oncology, vol. 13(11), May 2017, pp. 1021-1034.

Love, et al., "A Feasibility Study of the Intraductal Administration of Chemotherapy," Cancer Prevention Research, vol. 1, 2012, pp. 51-58.

Oken M.M., et al., "Toxicity and Response Criteria of the Eastern Cooperative Oncology Group," American Journal of Clinical Oncology, Dec. 1982, vol. 5(6), pp. 649-655.

Search Report and Written Opinion for Singapore Patent Application No. SG11202002105W dated Apr. 21, 2021, 8 pages.

Stearns, et al. Active tamoxifen metabolite plasma concentrations after coadministration of tamoxifen and the selective serotonin reuptake inhibitor paroxetine. J Natl Cancer Inst. Dec. 3, 2003;95(23):1758-64.

Sun M., et al., "Construction and Evaluation of a Novel Humanized HER2-Specific Chimeric Receptor," Breast Cancer Research, 2014, vol. 16:R61, 10 pages.

Wu X., et al., "The Tamoxifen Metabolite, Endoxifen, is a Potent Antiestrogen that Targets Estrogen Receptor Alpha for Degradation in Breast Cancer Cells," Cancer Research, Mar. 1, 2009, vol. 69(5), , pp. 1722-1727.

Zhao Y., et al., "A Herceptin-Based Chimeric Antigen Receptor with Modified Signaling Domains Leads to Enhanced Survival of Transduced T Lymphocytes and Antitumor Activity," The Journal of Immunology, https://www.researchgate.net/publication/38024914, Nov. 2009, vol. 183(9), pp. 5563-5574.

Lehmann, "Identification of Human Triple-Negative Breast Cancer Subtypes and Preclinical Models for Selection of Targeted Therapies," Journal of Clinical Invest, vol. 121 (7), 2011, pp. 2750-2767.

Journal of Pharmaceutical Science and Technology, Japan, 2006, vol. 66, No. 6, pp. 435-439.(No English Translation available. Document showing a well-known technique).

Love, Susan M., et al. "A Feasibility Study of the Intraductal Administration of Chemotherapy." Cancer Prevention Research, vol. 6, No. 1, Jan. 2013, pp. 51-58.

Taiwanese Patent Application No. 107131790 Search Report dated Jun. 30, 2022. English Translation included.

* cited by examiner

PRIOR ART

METHODS FOR MAKING AND USING ENDOXIFEN

CROSS-REFERENCE

This application is a continuation of U.S. patent application Ser. No. 16/641,985, filed Feb. 25, 2020, which is a U.S. National Phase Application under 35 U.S.C. § 371 of International Application No. PCT/US2018/050272, filed Sep. 10, 2018, which claims the benefit of U.S. Provisional Application No. 62/556,799, filed Sep. 11, 2017; U.S. Provisional Application No. 62/556,884, filed Sep. 11, 2017; U.S. Provisional Application No. 62/624,787, filed Jan. 31, 2018; and U.S. Provisional Application No. 62/693,885, filed Jul. 3, 2018, each incorporated herein by reference in their entireties.

BACKGROUND OF THE INVENTION

Breast cancer is by far the most common form of cancer in women, and it is the second leading cause of cancer death in humans. Despite advances in diagnosing and treating breast cancer, the prevalence of this disease has been steadily rising at a rate of about 1% per year since 1940. Today, the likelihood that a woman living in North America will develop breast cancer during her lifetime is one in eight. In addition to breast cancers, other breast disorders affecting a large number of women include benign but often precancerous lesions, such as ductal hyperplasia, lobular hyperplasia, atypical ductal hyperplasia, and atypical lobular hyperplasia.

Current best practice for the treatment of breast cancer is to diagnose breast cancer with mammography and then treat the patient with surgery, radiation therapy, and chemotherapy. The current widespread use of mammography has resulted in improved detection of breast cancer. Although breast cancer is about 100 times less common among men than among women, the lifetime risk of men getting breast cancer is about 1 in 1,000. About 2,470 new cases of invasive breast cancer will be diagnosed in men and about 460 men will die from breast cancer. American Cancer Society estimates that in 2017, 255,180 new cases of breast cancer will be diagnosed in both men and women combined and 41,070 subjects will die of breast cancer. Nonetheless, the death rate due to breast cancer has remained relatively unchanged at about 21 deaths per 100,000 women and 0.4 deaths per 100,000 men. All too often, breast cancer is discovered at a stage that is too far advanced, when therapeutic options and survival rates are severely limited.

Breast cancers include any malignant tumor of breast cells. There are several types of breast cancer. Exemplary breast cancers include, but are not limited to, ductal carcinoma in situ, lobular carcinoma in situ, invasive (or infiltrating) ductal carcinoma, invasive (or infiltrating) lobular carcinoma, inflammatory breast cancer, triple-negative breast cancer, ER+ breast cancer, HER2+ breast cancer, adenoid cystic (or adenocystic) carcinoma, low-grade adenosquamous carcinoma, medullary carcinoma, mucinous (or colloid) carcinoma, papillary carcinoma, tubular carcinoma, metaplastic carcinoma, and micropapillary carcinoma. A single breast tumor can be a combination of these types or be a mixture of invasive and in situ cancer.

Tamoxifen is a selective estrogen receptor modulator that is used for the treatment of women with endocrine responsive breast cancer, i.e., hormone-dependent or hormone-sensitive breast cancer. Adjuvant therapy primarily via oral delivery of tamoxifen is known to have severe side effects such as vasomotor symptoms, for example hot flashes, and reproductive tract (gynecologic) cancers. Patient compliance remains a problem with tamoxifen therapy. Further, the majority of the individuals on adjuvant tamoxifen therapy do not respond to the drug and 30-50% of the patients subsequently die of their disease.

Several cytochrome P450 (CYP) mutations have been proposed to cause reduced conversion of tamoxifen to its active metabolite, endoxifen, and reduce tamoxifen efficacy and increase resistance to the drug (Dickschen et al. Front Pharmacol. 2012; 3: 92. PMCID: PMC3357105). So far, over 140 allelic variants of CYP2D6 have been described and a substantial part of these are associated with reduced or absent activity of the encoded enzyme. Based on the combination of the carried alleles, each individual subject can be classified into one of four phenotypic groups: poor metabolizer (PM) with plasma endoxifen levels less than 30 nM, intermediate metabolizer (IM), extensive metabolizer (EM) and ultra-rapid metabolizer (UM), reflecting variations in levels of serum endoxifen. However, changes in the CYP genotype do not fully explain the tamoxifen resistance and the reduced endoxifen levels observed in some subjects.

Therefore, several alternatives to tamoxifen are being developed for the treatment of breast cancer, which include low dose-tamoxifen (Lazzeroni M et al. Breast Cancer Res. 2012 Oct. 29; 14(5):214) and tamoxifen's active metabolites, afimoxifene (see, U.S. Pat. Nos. 7,485,623; 7,507,769; 7,704,516; 7,786,172; 7,968,532; and 8,048,927; Mansel R et al. Breast Cancer Res Treat. 2007 December; 106(3):389-97. PubMed PMID: 17351746; Rouanet P et al. J ClinOncol. 2005 May 1; 23(13):2980-7. PubMed PMID: 15860853), endoxifen (see, U.S. Pat. Nos. 9,333,190; 9,220,680; 9,090,640; and 9,200,045; U.S. Publication Nos. 2009/0291134 and US20100112041), and their derivatives (see, U.S. Pat. No. 8,063,249; U.S. Publication Nos. 2015/0080339 and 2014/0193334). It is widely accepted that (Z)-endoxifen is the main active metabolite responsible for the clinical efficacy of tamoxifen.

While hydrochloride and citrate salts of endoxifen (See, e.g., Fauq et al., Bioorganic & Medicinal Chemistry Letters. 20 (2010) 3036-3038; Stearns et al., J. Natl. Cancer Inst. Vol 95, No. 23, 2003; US Publication Nos. 2009/0291134 and 2010/0112041; Clinical Trials Gov. Identifier Nos. NCT01273168 and NCT02311933; Goetz et al., 2015, San Antonio Cancer Symposium; Ahmad et al., Clinical Pharmacology & Therapeutics. 88(6) 814-817, 2010; and J Clin. Oncol. 30, 2012 (suppl; abstr 3089); Ahmad et al. Breast Cancer Research and Treatment 2010, 122, 579-584) are known in the art and currently under evaluation for metastatic cancer, there remains unmet medical need for new compositions and methods for the treatment and/or prevention of hormone-dependent breast and reproductive tract (gynecologic) disorders.

SUMMARY OF THE INVENTION

The present disclosure addresses this need by providing compositions and methods for the treatment and/or prevention of hormone-dependent breast and reproductive tract (gynecologic) disorders. In certain aspects, the present disclosure provides novel industrially scalable methods of making Z-endoxifen or salts thereof, crystalline forms of endoxifen, and compositions comprising them. In certain aspects, the present disclosure provides novel crystalline forms of endoxifen which may provide advantages including improved bioavailability and stability relative to other crystalline or amorphous forms.

In certain aspects, the present disclosure provides a composition comprising a crystalline form of a compound of Formula (III):

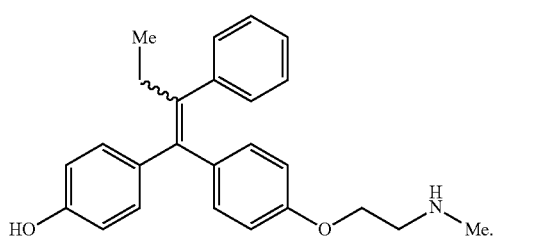

Formula (III)

In some embodiments, at least 90% by weight of the compound of Formula (III) in the composition is the (Z)-isomer. In some embodiments, the crystalline form is Form I of the compound of Formula (III). Crystalline Form I may be characterized by an x-ray powder diffraction pattern comprising major peaks at 16.8±0.3°, 17.1±0.3° and 21.8±0.3° two theta, and optionally further comprising at least one peak selected from 16.0±0.3°, 18.8±0.3° and 26.5±0.3° two theta. In some embodiments, the x-ray powder diffraction pattern further comprises at least one peak selected from 12.3±0.3°, 28.0±0.3° and 29.0±0.3° two theta. The x-ray powder diffraction pattern may further comprise peaks at 12.3±0.3°, 16.0±0.3°, 18.8±0.3°, 26.5±0.3°, 28.0±0.3° and 29.0±0.3° two theta. In some embodiments, crystalline Form I is characterized by an x-ray powder diffraction pattern substantially as set forth in FIG. 9 or FIG. 10. Greater than 90%, 95% or 99% by weight of the compound of Formula (III) in the composition may be crystalline Form I. In some embodiments, the composition comprises 0.01 mg to 200 mg of crystalline Form I, such as about 1 mg, 2 mg, 4 mg, 6 mg, 10 mg or 20 mg of crystalline Form I.

In some embodiments, the composition comprises the (E)-isomer and the (Z)-isomer of the compound of Formula (III) in an E/Z ratio between 0.9 and 1.3, such as about 1.1. In some embodiments, the crystalline form is Form II of the compound of Formula (III). Crystalline Form II may be characterized by an x-ray powder diffraction pattern comprising major peaks at 7.0±0.3°, 11.9±0.3°, 14.0±0.3° and 18.4±0.3° two theta, and optionally further comprising a peak at 22.0±0.3° two theta. In some embodiments, the x-ray powder diffraction pattern further comprises at least one peak selected from 6.6±0.3°, 13.3±0.3° and 20.0±0.3° two theta. The x-ray powder diffraction pattern may further comprise peaks at 6.6±0.3°, 13.3±0.3°, 20.0±0.3° and 22.0±0.3° two theta. In some embodiments, crystalline Form II is characterized by an x-ray powder diffraction pattern substantially as set forth in FIG. 11 or FIG. 12. Greater than 90%, 95% or 99% by weight of the compound of Formula (III) in the composition may be crystalline Form II. In some embodiments, the composition comprises 0.01 mg to 200 mg of crystalline Form II, such as about 1 mg, 2 mg, 4 mg, 6 mg, 10 mg or 20 mg of crystalline Form II.

In some embodiments, the composition comprises the (E)-isomer and the (Z)-isomer of the compound of Formula (III) in an E/Z ratio between 0.9 and 1.3, such as about 1.1. In some embodiments, the crystalline form is Form III of the compound of Formula (III). Crystalline Form III may be characterized by an x-ray powder diffraction pattern comprising major peaks at 11.9±0.3°, 13.9±0.3°, 17.1±0.3° and 17.7±0.3° two theta, and optionally further comprising a peak at 25.3±0.3° two theta. In some embodiments, the x-ray powder diffraction pattern further comprises at least one peak selected from 18.2±0.3°, 22.5±0.3° and 26.8±0.3° two theta. The x-ray powder diffraction pattern may further comprise peaks at 18.2±0.3°, 22.5±0.3°, 25.3±0.3° and 26.8±0.3° two theta. In some embodiments, crystalline Form III is characterized by an x-ray powder diffraction pattern substantially as set forth in FIG. 13. Greater than 90%, 95% or 99% by weight of the compound of Formula (III) in the composition may be crystalline Form III. In some embodiments, the composition comprises 0.01 mg to 200 mg of crystalline Form III, such as about 1 mg, 2 mg, 4 mg, 6 mg, 10 mg or 20 mg of crystalline Form III.

In certain aspects, the present disclosure provides a pharmaceutical composition comprising a pharmaceutically acceptable carrier or diluent and the composition comprising a crystalline form of a compound of Formula (III). A composition of the present disclosure may be formulated for oral, parenteral, topical, or intraductal delivery. In some embodiments, the composition is formulated for oral delivery as a tablet, a caplet, a capsule, or a pill. In some embodiments, a mean half-life of endoxifen in a subject treated with the composition is between 30 hours to 60 hours. A composition comprising a crystalline form of a compound of Formula (III) may be formulated for oral delivery as an enteric tablet, an enteric caplet, an enteric capsule, a delayed-release tablet, a delayed-release caplet or a delayed-release capsule. In some embodiments, the composition is administered to a subject for the treatment or prevention of a hormone-dependent breast disorder, a hormone-dependent reproductive tract disorder, or both in the subject.

In certain aspects, the present disclosure provides an oral composition comprising 1 mg to 200 mg per unit dose of the composition comprising a crystalline form of a compound of Formula (III) for administration to a subject in need thereof, wherein daily administration of the oral composition achieves in the subject:

a steady state plasma level of endoxifen within 7 to 21 days;

a steady state plasma level of endoxifen ranging from 25 nM to 300 nM;

a steady state plasma level of endoxifen greater than 30 nM;

maximal plasma levels of endoxifen within 2 to 10 hours after administering; or any combination thereof.

In some embodiments, a mean half-life of endoxifen in a subject treated with the composition comprising a crystalline form of a compound of Formula (III) is between 40 hours to 55 hours. In some embodiments, the composition is formulated as an enteric tablet, an enteric caplet, an enteric capsule, a delayed-release tablet, a delayed-release caplet or a delayed-release capsule. In some embodiments, at least 40%, at least 50%, at least 60%, at least 70%, at least 80%, or at least 90% of endoxifen in the composition is released in the intestines. In some embodiments, the composition comprising a crystalline form of a compound of Formula (III) exhibits a mean area under the curve extrapolated to time infinity ($AUC_{0-inf}$) of endoxifen of 200 hr*ng/mL to 10000 hr*ng/mL, of 300 hr*ng/mL to 8000 hr*ng/mL, of 400 hr*ng/mL to 6000 hr*ng/mL or of 700 hr*ng/mL to 6000 hr*ng/mL.

In certain aspects, the present disclosure provides a method of treating a subject in need thereof, the method comprising administering to the subject the composition comprising a crystalline form of a compound of Formula (III). In some embodiments, the subject has or is at risk of having a hormone-dependent breast disorder, a hormone-dependent reproductive tract disorder, or both. The hormone-dependent breast disorder or the hormone-dependent reproductive tract disorder may be a benign breast disorder, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancer, or vulvar cancer. In some embodiments, the subject has prostate cancer and has or is at risk of having gynecomastia. The subject may have tamoxifen-refractory or tamoxifen resistant hormone-dependent breast disorder or hormone-dependent reproductive tract disorder. In some embodiments, the subject is or will be treated with an SSRI drug selected from the group consisting of citalopram, escitalopram, fluoxetine, paroxetine, sertraline, and vilazodone.

In practicing any of the subject methods, the composition may comprise 0.01 mg to 200 mg of (Z)-endoxifen. In some embodiments, the subject is administered about 1 mg, 2 mg, 4 mg, 6 mg, 10 mg or 20 mg of (Z)-endoxifen daily. In some embodiments, a steady state plasma level of endoxifen in the subject is greater than 30 nM. The steady state plasma level of endoxifen may be achieved within 7 to 21 days of the first administration of the composition. In some embodiments, time to maximum plasma levels of endoxifen ranges from 2 hours to 10 hours or from 4 hours to 8 hours after administering the composition.

In certain aspects, the present disclosure provides a method of treating a subject having or at risk of having a hormone-dependent breast disorder, a hormone-dependent reproductive tract disorder, or both, the method comprising administering the composition comprising a crystalline form of a compound of Formula (III), wherein administration of the composition achieves:

a mean half-life of endoxifen in the subject ranging from 30 hours to 60 hours after administration;

a time to maximum plasma levels of endoxifen ranging from 4 hours to 8 hours after administration; and a steady state plasma level of endoxifen greater than 30 nM.

In some embodiments, the hormone-dependent breast disorder and the hormone-dependent reproductive tract disorder are selected from the group consisting of benign breast disorders, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancer, and vulvar cancer.

In practicing any of the subject methods, the composition may comprise 0.01 mg to 200 mg of (Z)-endoxifen. In some embodiments, the subject is administered about 1 mg, 2 mg, 4 mg, 6 mg, 10 mg or 20 mg of (Z)-endoxifen. The mean area under the curve extrapolated to time infinity ($AUC_{0-inf}$) of endoxifen may be 200 hr*ng/mL to 10000 hr*ng/mL, 300 hr*ng/mL to 8000 hr*ng/mL, 400 hr*ng/mL to 6000 hr*ng/mL or 700 hr*ng/mL to 6000 hr*ng/mL. In some embodiments, the composition is formulated as an enteric tablet, an enteric caplet, an enteric capsule, a delayed-release tablet, a delayed-release caplet or a delayed-release capsule. In some embodiments, at least 40%, at least 50%, at least 60%, at least 70%, at least 80%, or at least 90% of endoxifen in the composition is released in the intestines. The composition may be administered once a day, twice a day, thrice a day, four times a day, every other day, twice a week, weekly, fortnightly, twice a month, monthly, quarterly, once every six months, or annually.

In one aspect, the present disclosure provides an industrially scalable process for manufacturing (Z)-endoxifen or salts thereof, comprising the steps of: (a) subjecting a mixture of (E)-endoxifen and (Z)-endoxifen, compounds of Formula (III), represented by

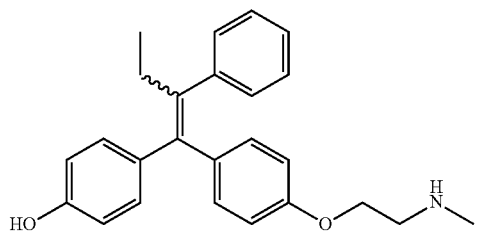 [SMILES: CCC(=C(c1ccc(O)cc1)c1ccc(OCCNC)cc1)c1ccccc1]

to fractional crystallization from a first solvent to form a first crystalline solid and first crystalline mother liquor, wherein the first mother liquor has an E/Z ratio of at least 50% higher (Z) endoxifen as compared with the E/Z ratio of the mixture of (E)-endoxifen and (Z)-endoxifen; (b) subjecting the first mother liquor to recrystallization from a second solvent by concentrating the first mother liquor or by swapping out the first solvent from the first mother liquor one or more times with the second solvent, to form a second crystalline solid and a second mother liquor, wherein the second crystalline solid is ≥90% (Z)-endoxifen; and (c) optionally, subjecting the second crystalline solid to recrystallization from a third solvent or chromatographic treatment one or more times to form a third crystalline solid. In some embodiments, any one or more of the first solvent, the second solvent, and the third solvent are preheated to a temperature ranging from 40° C. to 80° C.

In some aspects, the present disclosure provides an industrially scalable process for manufacturing crystalline Form I of the compound of Formula (III), comprising the steps of (a) subjecting a mixture of (E)-endoxifen and (Z)-endoxifen, compounds of Formula (III), represented by

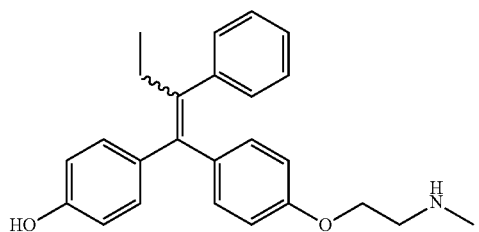 [SMILES: CCC(=C(c1ccc(O)cc1)c1ccc(OCCNC)cc1)c1ccccc1]

to fractional crystallization from a first solvent to form a first crystalline solid and first mother liquor, wherein the first mother liquor has an E/Z ratio of at least 50% higher (Z) endoxifen as compared with the E/Z ratio of the mixture of (E)-endoxifen and (Z)-endoxifen; (b) subjecting the first mother liquor to recrystallization from a second solvent by concentrating the first mother liquor or by swapping out the first solvent from the first mother liquor with the second solvent one or more times, to form a second crystalline solid and a second mother liquor, wherein the second crystalline solid is ≥90% (Z)-endoxifen; and (c) subjecting the second crystalline solid to recrystallization from a third solvent or chromatographic treatment one or more times to form a third crystalline solid, wherein the third crystalline solid is crystalline Form I of the compound of Formula (III).

In certain aspects, the present disclosure provides a crystalline form of a compound of Formula (III) produced according to a method described herein. In some embodiments, the crystalline form is Form I of the compound of Formula (III). In some embodiments, the crystalline form is Form II of the compound of Formula (III). In some embodiments, the crystalline form is Form III of the compound of Formula (III).

In another aspect, the present disclosure provides that the mixture of (E)-endoxifen and (Z)-endoxifen, compounds of Formula (III), in step a is pretreated with 6N HCl and neutralized with 8N NaOH.

In another aspect, the industrially scalable process further comprises preparing the mixture of (E)-endoxifen and (Z)-endoxifen by coupling the compound of Formula (II), (4-hydroxyphenyl)(4-(2-(methylamino)ethoxy)phenyl) methanone, to propiophenone mediated by a McMurry reaction via a titanium salt and a reducing agent in an inert organic solvent to form the mixture of (E)-endoxifen and (Z)-endoxifen; and wherein the compound of Formula (II) has a structure represented by

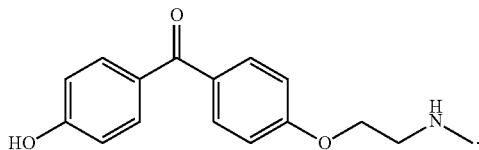

In yet another aspect, the industrially scalable process further comprises preparing the compound of Formula (II) by demethylating [4-[2-(dimethylamino)ethoxy]phenyl](4-hydroxyphenyl)methanone, the compound of Formula (I), wherein the compound of Formula (I) has the structure

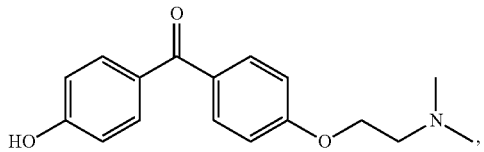 [SMILES: CN(C)CCOc1ccc(C(=O)c2ccc(O)cc2)cc1]

with a demethylating agent and a proton acceptor in an inert organic solvent to form the compound of Formula (II).

The present disclosure also provides an industrially scalable process for manufacturing (Z)-endoxifen and salts thereof, comprising the steps of: (a) subjecting a mixture of (E)-endoxifen and (Z)-endoxifen, compounds of Formula (III) represented by

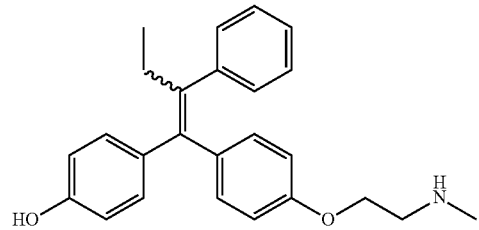 [SMILES: CCC(=C(c1ccc(O)cc1)c1ccc(OCCNC)cc1)c1ccccc1]

to fractional crystallization from ethyl acetate to form a first crystalline solid and first crystalline mother liquor, wherein the first mother liquor has an E/Z ratio of at least 30% higher (Z) endoxifen as compared with the E/Z ratio of the mixture of (E)-endoxifen and (Z)-endoxifen; (b) subjecting the first mother liquor to recrystallization from IPA or IPA/PPW (1:1 v/v) by concentrating the first mother liquor, or by swapping out ethyl acetate from the first mother liquor one or more times with IPA or IPA/PPW, to form a second crystalline solid and a second mother liquor, wherein the second crystalline solid is ≥90% (Z)-endoxifen; and (b) optionally, subjecting the second crystalline solid to recrystallization from ethanol or column chromatographic treatment one or more times to form a third crystalline solid.

In some embodiments, the mixture of (E)-endoxifen and (Z)-endoxifen, compounds of Formula (III), is prepared by coupling the compound of Formula (II), (4-hydroxyphenyl)(4-(2-(methylamino)ethoxy)phenyl) methanone, to propiophenone mediated by a McMurry reaction comprising the steps of: (a) reacting the compound of Formula (II) with propiophenone (1:0.01 to 1.5 wt/wt) in an inert organic solvent (1:1 to 1: 20 wt/wt); (b) preparing a titanium salt (1:0.1 to 1:12 wt/wt) and a reducing agent (1:0.01 to 1:10 wt/wt) in an inert organic solvent (1:1 to 1: 20 wt/wt); and (c) reacting the compound of Formula (II) of step (a) with the titanium salt and a reducing agent in an inert organic solvent of step (b) to form the mixture of (E)-endoxifen and (Z)-endoxifen; and wherein wt/wt is with respect to the compound of Formula (II).

In other embodiments, the mixture of (E)-endoxifen and (Z)-endoxifen, compounds of Formula (III), is prepared by coupling the compound of Formula (II), (4-hydroxyphenyl)(4-(2-(methylamino)ethoxy)phenyl) methanone, to propiophenone mediated by a McMurry reaction comprising the steps of: (a) reacting the compound of Formula (II) with propiophenone (1:0.01 to 1:5 wt/wt) in THF (1:1 to 1:20 wt/wt); (b) preparing a TiCl$_4$ (0.1 to 4 wt/wt) and Zn (0.01 to 1:2 wt./wt) in THF (1:1 to 1:20 wt/wt; and (c) reacting the compound of Formula (II) of step (a) with the TiCl$_4$ and Zn in THF of step (b) to form the mixture of (E)-endoxifen and (Z)-endoxifen; and wherein wt/wt is with respect to the compound of Formula (II).

In some embodiments, the compound of Formula (II) is generated by demethylating the compound of Formula (I) with a demethylating agent (1:0.5 to 1:10 wt/wt) and a proton acceptor (1:0.5 to 1:10 wt/wt) in an inert organic solvent (1:1 to 1:20 wt/wt) to form a compound of Formula (II), wherein the wt/wt is with respect to the compound of Formula (I).

In some embodiments, the compound of Formula (II) is prepared by demethylating the compound of Formula (I) with 1-chloroethyl chloroformate and DIPEA in THF to form the compound of Formula (II) comprising the steps of: (a) reacting the compound of Formula (I) with DIPEA (1:0.5 to 1:10 wt/wt) in THF (1:20 wt/wt); (b) adding 1-chloroethyl chloroformate (1:0.5 to 1:10 wt./wt); (c) distilling with methanol one or more times (1:1 to 1:10 wt./wt); (e) reacting with methanol (1:1 to 1:5 wt/wt)/HCl (1:1 to 1:10 wt/wt); and (e) neutralizing with NaOH (1:1 to 1:10 wt/wt); and wherein wt/wt is with respect to the compound of Formula (I).

In another aspect, the present disclosure provides process for making (Z)-endoxifen gluconate salts by reacting (Z)-endoxifen with D-gluconate or L-Gluconate to form (Z)-endoxifen L-gluconate or (Z)-endoxifen D-gluconate.

In still another aspect, the present disclosure provides that (Z)-endoxifen, (E)-endoxifen, compounds of Formula (III), the compound of Formula (II), and salts thereof prepared by any of the processes as described herein are stable. In a particular aspect, the (Z)-endoxifen free base is stable at ambient temperature for at least 9 months.

In certain aspects, the present disclosure provides an industrially scalable process for manufacturing crystalline Form II or III of the compound of Formula (III), comprising (a) reacting to 6N HCL (1:1 to 1:5 wt/wt) in ethyl acetate (1:1 to 1:20 wt/wt) a starting mixture of (E)-endoxifen and (Z)-endoxifen having an E/Z-ratio ranging from 99:1 to 40:60; (b) neutralizing with 8N NaOH (1:1 to 1:20 wt/wt); (c) washing one or more times with ethyl acetate; (d) washing one or more times with a mixture of ethyl acetate and n-heptane; and (e) recovering crystalline Form II or III of the compound of Formula (III); wherein wt/wt is with respect the starting mixture of (E)-endoxifen and (Z)-endoxifen.

In yet another aspect, the present disclosure provides a composition comprising (Z)-endoxifen free base or a salt thereof prepared according to any of the processes described herein. The compositions are formulated for oral, parenteral, topical, and intraductal delivery. The compositions are formulated for oral delivery as tablets, caplets, capsules, or pills. In some embodiments, the compositions are formulated for oral delivery tablet as enteric tablets, enteric caplets, enteric capsules, delayed-release tablets, delayed-release caplets, and delayed-release capsules.

In certain aspects, the present disclosure provides compositions having certain pharmacokinetic profiles. In one aspect, the present disclosure provides that at least 40%, at least 50%, at least 60%, at least 70%, at least 80%, at least 90% of the endoxifen in the compositions is released in intestines. In another aspect, the present disclosure provides that the endoxifen in the compositions has a mean half-life of in a subject ranging from 30 hours to 60 hours after administration. In some embodiments, the mean half-life of endoxifen in a subject ranges from 40 hours to 55 hours after administration. In another aspect, the present disclosure provides that the mean area under the curve extrapolated to time infinity ($AUC_{0-inf}$) of 200 hr*ng/mL to 10000 hr*ng/mL, of 300 hr*ng/mL to 8000 hr*ng/mL, of 400 hr*ng/mL to 6000 hr*ng/mL or of 700 hr*ng/mL to 6000 hr*ng/mL.

In another aspect, the present disclosure provides oral compositions comprising 1 mg to 200 mg per unit dose of (Z)-endoxifen free base or a salt thereof, for administration to a subject in need thereof, wherein daily administration of the oral composition achieves in the subject: (i) a steady state plasma level of endoxifen within 7 to 21 days; or (ii) a steady state plasma level of endoxifen ranging from 25 nM to 300 nM; or (iii) a steady state plasma level of endoxifen greater than 30 nM; or (iv) maximal plasma levels of endoxifen within 2 to 10 hours after administering; or (v) any combination thereof. The present disclosure also provides that the compositions are administered to a subject in need thereof for the treatment and prevention of a hormone-dependent breast disorder, a hormone-dependent reproductive tract disorder, or both in a subject.

In certain aspect, the present disclosure provides methods of treating a subject in need thereof, the method comprising administering to the subject an oral composition as disclosed herein. In some embodiments, the subject has or is at risk of having a hormone-dependent breast disorder, a hormone-dependent reproductive tract disorder, or both. In various embodiments, the hormone-dependent breast disorder or the hormone-dependent reproductive tract disorder is a benign breast disorder, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancer, or vulvar cancer.

In some embodiments, the subject has prostate cancer and wherein the subject further has or is at risk of having gynecomastia.

In certain aspects, the present disclosure provides certain patient populations that would benefit from such methods of treatment. In some embodiments, the patient population is a tamoxifen-refractory or tamoxifen resistant population. In certain embodiments, the subject has tamoxifen-refractory or tamoxifen resistant hormone-dependent breast disorder or hormone-dependent reproductive tract disorder. In other embodiments, the patient population comprises subjects that are or will be treated with an SSRI drug selected from the group consisting of citalopram, escitalopram, fluoxetine, paroxetine, sertraline, and vilazodone.

In an aspect, the present disclosure provides certain doses of (Z)-endoxifen to be administered to subjects in need thereof. In various embodiments, the subjects are administered 0.01 mg to 200 mg of (Z)-endoxifen. In certain embodiments, the subject is administered 1 mg, 2 mg, 4 mg, 6 mg, 10 mg or 20 mg of (Z)-endoxifen daily.

In another aspect, the present disclosure provides methods of treatment of subjects, wherein a steady state plasma level of endoxifen in of the subject is greater than 30 nM upon administration of the compositions. In some embodiments, such a steady state plasma level of endoxifen is achieved within 7 to 21 days of the first administration of the composition. In some embodiments, the time to maximum plasma levels of endoxifen ranges from 2 hours to 10 hours or from 4 hours to 8 hours after administering the composition.

In another aspect, the present disclosure provides methods of treating a subject having or at risk of having a hormone-dependent breast disorder, a hormone-dependent reproductive tract disorder, or both, the method comprising administering an oral composition comprising (Z)-endoxifen or a salt thereof, wherein administration of the composition achieves: (i) a mean half-life of endoxifen in the subject ranging from 30 hours to 60 hours after administration; (ii) a time to maximum plasma levels of endoxifen ranging from 4 hours to 8 hours after administration; and (iii) a steady state plasma level of endoxifen greater than 30 nM. In certain embodiments, the subject is administered 1 mg, 2 mg, 4 mg, 6 mg, 10 mg or 20 mg of (Z)-endoxifen. In other embodiments, the mean area under the curve extrapolated to time infinity ($AUC_{0-inf}$) of 200 hr*ng/mL to 10000 hr*ng/mL, of 300 hr*ng/mL to 8000 hr*ng/mL, of 400 hr*ng/mL to 6000 hr*ng/mL or of 700 hr*ng/mL to 6000 hr*ng/mL. In some embodiments, the composition is formulated as an enteric tablet, an enteric caplet, an enteric capsule, a delayed-release tablet, a delayed-release caplet or a delayed-release capsule. In some embodiments, at least 40%, at least 50%, at least 60%, at least 70%, at least 80%, at least 90% of the endoxifen is released in intestines. In some embodiments, the composition is administered once a day, twice a day, thrice a day, four times a day, every other day, twice a week, weekly, fortnightly, twice a month, monthly, quarterly, once every six months, or annually. In some embodiments, the hormone-dependent breast disorder and the hormone-dependent reproductive tract disorder are selected from the group consisting of benign breast disorders, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancer, and vulvar cancer.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
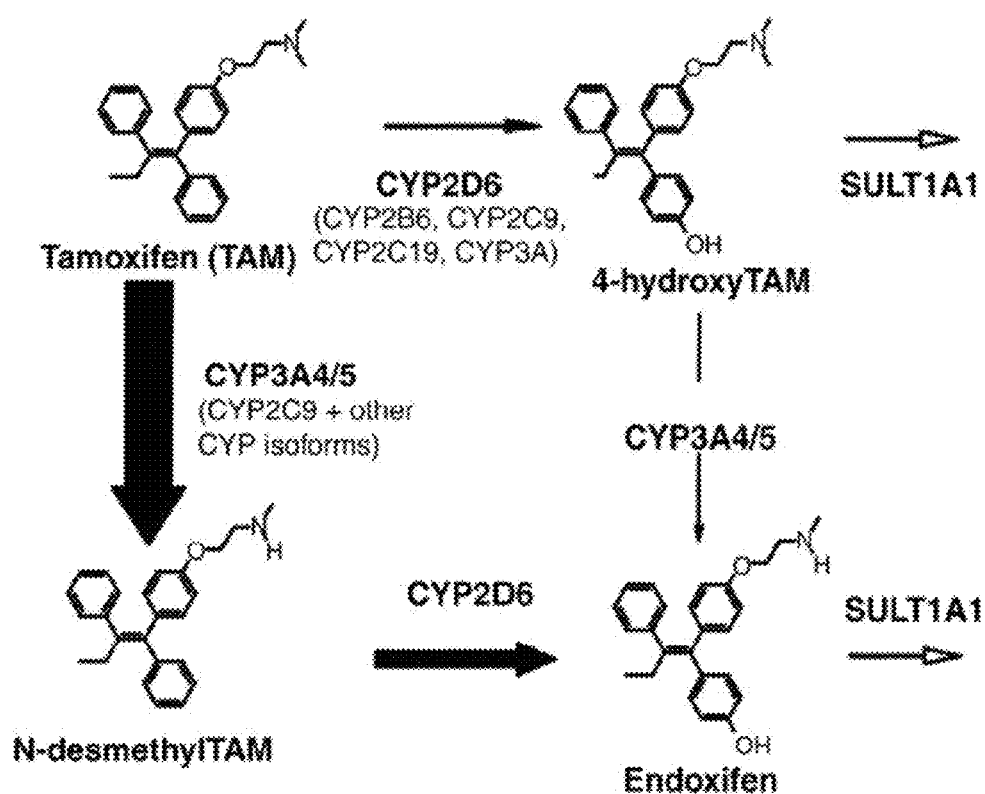
FIG. 1 is a scheme depicting the metabolic route of tamoxifen to endoxifen and other metabolites. The plasma concentrations of 4-hydroxytamoxifen are low relative to those of N-desmethyl tamoxifen, indicating that the primary route for metabolism of the parent drug is via N-demethylation by cytochrome P450 3A4 (CYP3A4) to N-desmethyl tamoxifen, followed by hydroxylation by cytochrome P450 2D6 (CYP2D6) to endoxifen.

Compounds are described using standard nomenclature. Unless otherwise defined, all technical and scientific terms used herein have the same meaning as is commonly understood by one of skill in the art to which this invention belongs.

As used herein, the terms "a," "an," and "the" include plural reference unless the context dictates otherwise.

As used herein, the terms "active pharmaceutical ingredient", "active ingredient", "API," "drug," "active," "actives" or "therapeutic agent" may be used interchangeably to refer to the pharmaceutically active compound(s) in a pharmaceutical composition. This is in contrast to other ingredients in the compositions, such as excipients, which are substantially or completely pharmaceutically inert. A suitable API in accordance with the present disclosure is one where there is or likely may be patient compliance issues for treating a certain disease, condition, or disorder. The therapeutic agent as used herein includes the active compound and its salts, prodrugs, and metabolites. As used herein the term "drug" means a compound intended for use in diagnosis, cure, mitigation, treatment, and/or prevention of disease in man or other animals.

As used herein, "adjuvant therapy" refers to a therapy that follows a primary therapy and that is administered to subjects at risk of relapsing. Adjuvant systemic therapy in case of breast cancer or reproductive tract cancer, for example with tamoxifen, usually begins soon after primary therapy to delay recurrence, prolong survival or cure a subject.

As used herein, the term "tamoxifen" refers to (Z)-2-[4-(1,2-diphenyl-1-butenyl)phenoxy]-N,N-dimethylethanamine. Tamoxifen can also refer to the E-isomer or a combination of the E-isomer and the Z-isomer.

As used herein, the terms "4-hydroxytamoxifen," "afimoxifene," and "4-OHT" used interchangeably refer to 4-1-[4-[2-(dimethylamino)ethoxy]phenyl]-2-phenylbut-1-enyl]phenol, and constitutes an active metabolite of tamoxifen. 4-OHT can refer to the Z-isomer, E-isomer or a combination thereof.

As used herein, the term "endoxifen" refers to 4-hydroxy-N-desmethyl-tamoxifen. It is a secondary active metabolite of tamoxifen.

Embodiments that reference throughout this specification to "a compound", such as compounds of Formula (I), Formula (II), Formula (III) and Formula (IV), include the polymorphic, salt, free base, co-crystal, and solvate forms of the formulas and/or compounds disclosed herein. Thus, the appearances of the phrases "a compound", "compound of Formula (I)", "compound of Formula (II)", "compounds of Formula (III)" and "compound of Formula (IV)" include Form I of the compound of Formula (IV), Forms II-III of the compounds of Formula (III), the free base of the compound of Formula (IV), the free base of the compounds of Formula (III), and/or the gluconate salts as described herein.

The terms "crystalline form", "polymorph" and "Form" may be used interchangeably herein, and are meant to include all crystalline and amorphous forms of the compound, including, for example, polymorphs, pseudopolymorphs, salts, solvates, hydrates, unsolvated polymorphs (including anhydrates), conformational polymorphs, and amorphous forms, as well as mixtures thereof, unless a particular crystalline or amorphous form is referred to.

Compound of the present disclosure include crystalline and amorphous forms of those compounds, including, for example, polymorphs, pseudopolymorphs, salts, solvates, hydrates, unsolvated polymorphs (including anhydrates), conformational polymorphs, and amorphous forms of the compounds, as well as mixtures thereof.

All compounds disclosed herein are further understood to include all possible isotopes of atoms occurring in the compounds. Isotopes include those atoms having the same atomic number but different mass numbers. By way of example, and without limitation, isotopes of hydrogen include tritium and deuterium and isotopes of carbon include $^{11}C$, $^{13}C$ and $^{14}C$.

As used herein and in the claims, the terms "comprising," "containing," and "including" are inclusive, open-ended and do not exclude additional unrecited elements, compositional components or method steps. Accordingly, the terms "comprising" and "including" encompass the more restrictive terms "consisting of" and "consisting essentially of."

As used herein, the term "combination therapy" refers to the use of a composition described herein in combination with one or more additional treatment. Treatment in combination therapy can be any treatment such as any prophylactic agent, therapeutic agent (such as chemotherapy), radiotherapy, surgery and the like. The combination can refer to inclusion of a therapeutic or prophylactic agent in a same composition as a composition disclosed herein (for example, in the same capsule, tablet, ointment, etc.) or in separate compositions (for example, in 2 separate capsules). The separate compositions may be in a different dosage form. The use of the terms "combination therapy" and "in combination with" does not restrict the order in which a composition described herein and prophylactic and/or therapeutic agent and/or treatment are administered to a subject in need thereof. Compositions of the present disclosure can be administered prior to (e.g., 1 minute (min), 5 min, 15 min, 30 min, 45 min, 1 hour (h), 2 h, 4 h, 6 h, 8 h, 10 h, 12 h, 24 h, 36 h, 48 h, 72 h, 96 h, 1 week (wk), 2 wk, 3 wk, 4 wk, 5 wk, 6 wk, 8 wk, 12 wk, 6 months (m), 9 m, or 1 year before), concomitant with, or subsequent to (e.g., 1 minute (min), 5 min, 15 min, 30 min, 45 min, 1 hour (h), 2 h, 4 h, 6 h, 8 h, 10 h, 12 h, 24 h, 36 h, 48 h, 72 h, 96 h, 1 week (wk), 2 wk, 3 wk, 4 wk, 5 wk, 6 wk, 8 wk, 12 wk, 6 months (m), 9 m, or 1 year after) administration of one or more prophylactic and/or therapeutic agent and/or treatment to a subject in thereof. Combination therapy as used herein can also refer to treatment of a subject having a single disease or multiple diseases, for example, prostate cancer in men and gynecomastia.

As used herein, the term "test sample" means sample of blood obtained from a subject. It is to be understood that when blood sample is obtained from a subject, subject's blood is used for determining the subject's endoxifen levels and/or other biomarkers that may be measured or tested. As used herein "plasma endoxifen" is used to refer to endoxifen levels in the subject's test sample, whether the test is conducted on whole blood, plasma or serum.

As used herein, the term "dosage form" means the form in which the compounds or compositions of the present disclosure are delivered to a patient.

As used herein, the term "pharmaceutically acceptable" or "pharmacologically acceptable" means materials, compositions, or vehicles that are compatible with other ingredients of the formulation and that they do not substantially produce adverse reactions, e.g., toxic, allergic, or immunological reactions, when administered to a subject. They may be approved by a regulatory agency, e.g., of the U.S. Federal or state government or listed in the U.S. pharmacopeia or other generally recognized pharmacopeia for use in animals, and more particularly in humans.

As used herein, the term "pharmaceutically acceptable carrier" or "carrier" means a pharmaceutically acceptable material, composition, or vehicle, such as a liquid or solid filler, diluent, excipient, solvent, or encapsulating material, involved in carrying or transporting one or more of the compounds of the present disclosure from one tissue, organ, or portion of the body or across the skin.

As used herein, the term "pharmaceutically acceptable salt" refers to any salt (e.g., obtained by reaction with an acid or a base) of a compound of the present disclosure that is physiologically tolerated in a subject (e.g., a mammal, and/or in vivo, ex-vivo, in vitro cells, tissues, or organs). A "salt" of a compound of the present disclosure may be derived from inorganic or organic acids and bases. Suitable anion salts include, arecoline, besylate, bicarbonate, bitartarate, butylbromide, citrate, camysylate, gluconate, glutamate, glycollylarsanilate, hexylresorcinate, hydrabamine, hydrobromide, hydrochloride, hydroxynapthanoate, isethionate, malate, mandelate, mesylate, methylbromide, methylbromide, methylnitrate, methylsulfate, mucate, napsylate, nitrate, pamaoate (Embonate), pantothenate, phosphate/diphosphate, polygalacuronate, salicylate, stearate, sulfate, tannate, teoclate, fatty acid anions, and triethiodide.

Suitable cations include benzathine, clemizole, chloroprocaine, choline, diethylamine, diethanolamine, ethylenediamine, meglumine, piperazine, procaine, aluminum, barium, bismuth, lithium, magnesium, potassium, and zinc.

For the purposes of this application, the salts of the compounds of the present disclosure are contemplated to be pharmaceutically acceptable for therapeutic uses. However, salts of acids and bases that are non-pharmaceutically acceptable may also be useful, for example, in the preparation or purification of a pharmaceutically acceptable compound.

As used herein, the term "pharmaceutical composition" means a combination of the active agent (e.g., an active pharmaceutical compound or ingredient, API) with a carrier, inert or active (e.g., a phospholipid), making the compositions specially suitable for diagnostic or therapeutic uses in vitro, in vivo, or ex vivo.

As used herein "primary therapy" refers to a first line of treatment upon initial diagnosis of a hormone-dependent breast disorder, a hormone-dependent reproductive tract disorder, or both in a subject. Exemplary primary therapies may involve surgery, a wide range of chemotherapies, and radiotherapy.

As used herein, the terms "subject," "patient," "participant," and "individual," may be used interchangeably herein and refer to a mammal such as a human. Mammals also include pet animals such as dogs, cats, laboratory animals, such as rats, mice, and farm animals such as cows and horses. Unless otherwise specified, a mammal may be of any gender or sex.

As used herein, the term "tamoxifen refractory" refers to a subject that has been dosed daily with tamoxifen for at least 2 days and has a level of plasma endoxifen of less than 30 nM (e.g., less than 20 nM, less than 25 nM, or less than 30 nM). As used herein, the term "tamoxifen resistance" refers to two classes of resistance: (a) de novo resistance, i.e., non-responsiveness to tamoxifen therapy from the beginning of the treatment, or (b) acquired resistance, i.e., non-responsiveness to tamoxifen therapy after initial responsiveness or tamoxifen-dependent growth/stimulated growth while continuing to express estrogen receptors (Minsun Chang. Biomol. Ther. 20(3), 256-267 (2012)). The acquired resistance to tamoxifen may develop as early as 3 m to 1 year to as late as 5 to 10 years. As used herein, the term "reference plasma endoxifen level" refers to a value of 30 nM.

As used herein, the term "unit dosage form" refers to physically discrete units suitable for unitary dosages for subjects, each unit containing a predetermined quantity of active material calculated to produce the desired therapeutic effect, in association with a suitable pharmaceutical excipient.

It is specifically understood that any numerical value cited herein includes all values from the lower value to the upper value, i.e., all possible combination of numerical values between the lowest value and the highest value enumerated are to be considered to be expressly stated in this application and the endpoint of all ranges are included within the range and independently combinable. For example, if a concentration range or beneficial range is stated as 1% to 50%, it is intended that values such as 2% to 40%, 10% to 30%, or 1% to 3% etc., are expressly enumerated in this specification. It is also to be understood that if a concentration or dose is stated as a specific value such as 1 mg or 10 mg, it is intended that it is intended to include 10% variation. As another example, a stated concentration of 20% is intended to include values±10%. Yet another example, if a ratio of 1:10 to 10:1 is stated, then it is intended that ratios such as 1:9 to 9:1, from 1:8 to 8:1, from 1:7 to 7:1, from 1:6 to 6:1, from 1:5 to 5:1, from 1:4 to 4:1, from 1:3 to 3:1, from 1:2 to 2:1, from 1:1 to 2:1 or from 2:5 to 3:5 etc. are specifically intended. There are only some examples of what is specifically intended. Unless specified otherwise, the values of the constituents or components of the compositions are expressed in weight percent of each ingredient in the component.

All methods described herein can be performed in a suitable order unless otherwise indicated or otherwise clearly contradicted by context. The use of any and all examples, or exemplary language (e.g., "such as" and "the like") is intended merely to illustrate the invention and does not pose a limitation on the scope of the invention unless otherwise claimed. No language in the specification should be construed as any indicating any non-claimed element as essential to practice of the invention as used herein.

As used herein, the terms "hormone-dependent breast disorder," "hormone-dependent reproductive tract disorder," "hormone-dependent breast and reproductive tract disorder" each and collectively include, without limitation, any breast or reproductive tract (gynecologic) disorder that is related to or is sensitive to high estrogen or normal estrogen levels that need to be reduced, disorders with estrogen-receptor positive (ER+) and/or progesterone-receptor positive (PR+) disorders, for example, breast disorders, endometriosis, uterine fibroids (also called leiomyomas) etc. Reproductive tract disorders include endometrial, ovarian, cervical, uterus, vaginal, and vulvar cancers. The terms "estrogen-related disorder" and "estrogen-receptor related disorder" may be used interchangeably to refer to the foregoing hormone dependent disorders. The disorders may be presented primarily or secondarily to an underlying disease, for example, prostate cancer or other disorders such as liver diseases. Hormone-dependent breast and reproductive tract disorder include, for example, McCune-Albright syndrome, which is a disorder caused by a mutation in the GNAS gene affecting bones, skin, and several hormone-producing (endocrine) tissues, often resulting in abnormal scar-like (fibrous) tissue in their bones, a condition called polyostotic fibrous dysplasia, hyperthyroidism in individuals carrying such mutations, and in girls often resulting in precocious puberty.

As used herein, "breast disorder" means any aberration or a constellation of aberrations in the breast. Such aberration may be proliferative, non-proliferative, benign or malignant. Breast disorders include benign lesions of the breast (e.g., hyperplasia), increased breast density, gynecomastia, mastalgia, and breast cancer. Benign breast lesions include, but are not limited to, hyperplasia, atypia, ductal hyperplasia, lobular hyperplasia, atypical ductal hyperplasia (ADH), and atypical lobular hyperplasia (ALH). While not cancerous, ADH and ALH may be indicative of a predisposition for breast cancer.

Breast density is a breast disorder identified by visual techniques such as mammography and reflects increased fibroglandular tissue within the breast, i.e., overgrowth of stromal and epithelial cells in the breast. Breast density is classified in 4 classes—Class A, B, C and D—based on the degree of severity of the density. It is an independent risk factor for breast cancer. At least 23 states in the USA require physicians to inform subjects if they have dense breast(s). There is currently no treatment for dense breasts, although subjects are reminded to make healthy lifestyle choices and undergo regular mammograms to monitor changes in breast.

Gynecomastia is a common male breast condition reflecting increased hyperplasia of the breast tissue, including epithelial hyperplasia, with prevalence of asymptomatic gynecomastia of 60% to 90% in neonates, 50% to 60% in adolescents, and up to 70% in men aged 50 to 69 years (Therapeutics and Clinical Risk Management 2011:7, 145-148). Newborn gynecomastia usually resolves itself within 4 weeks of birth and at least half of adolescent males experience gynecomastia with typical onset of 13 to 14 years of age (Tanner stage 3 or 4). Gynecomastia has been proposed to be a risk factor for male breast cancer.

Further, gynecomastia often presents itself secondarily to an underlying disorder such as prostate cancer, cirrhosis and liver disease, male hypogonadism, hyperthyroidism, renal failure and in patients undergoing hemodialysis, Type I diabetes mellitus, etc. Further, medications, such as anti-androgen medications or certain anti-psychotics, themselves have been reported to cause up to 25% of cases of gynecomastia and can be categorized by their hormone-like action. For example, the most common side effects attributed to bicalutamide, a nonsteroidal antiandrogen used for treatment of prostate cancer, are gynecomastia and breast pain.

As used herein, "breast cancer" means any malignant tumor of breast cells. Breast cancer may be at any stage of breast cancer, including stages of a pre-cancer, an early stage cancer, a non-metastatic cancer, a pre-metastatic cancer, a locally advanced cancer, and a metastatic cancer. There are several types of breast cancer. Exemplary breast cancers include, but are not limited to, ductal carcinoma in situ (DCIS), lobular carcinoma in situ (LCIS), invasive (or infiltrating) lobular carcinoma (ILC), invasive (or infiltrating) ductal carcinoma (IDC), microinvasive breast carcinoma (MIC), inflammatory breast cancer, ER-positive (ER+) breast cancer, ER-negative (ER−) breast cancer, HER2+ breast cancer, triple negative breast cancer (TNBC), adenoid cystic (adenocystic) carcinoma, low-grade adenosquamatous carcinoma, medullary carcinoma, mucinous (or colloid) carcinoma, papillary carcinoma, tubular carcinoma, metaplastic carcinoma, or micropapillary carcinoma. A single breast cancer tumor can be a combination of these types or be a mixture of invasive and in situ cancer.

DCIS is the most common non-invasive breast cancer. It involves the cell lining of the breast ducts. In DCIS, the cells have not spread beyond the walls of the duct into the surrounding breast tissue. About 1 in 5 new breast cancer cases will be DCIS. LCIS is a pre-cancerous neoplasia. It may be indicative of a predisposition for invasive cancer. LCIS only accounts for about 15% of the in situ (ductal or lobular) breast cancers.

IDC is the most invasive breast cancer. As the name applies, it is a carcinoma that begins in the breast ducts and then invades the surrounding fatty tissue. About 8 to 10 invasive breast cancers are infiltrating ductal carcinomas. IDC is often treated by surgery to excise the cancerous tissue, and radiation therapy. In addition, chemotherapy combined with immunotherapy (e.g., tamoxifen and tratuzumab) is often used to treat IDC. If the tumor is larger than 4 cm, then a radical mastectomy may be performed.

ILC is a cancer that develops in the lobules of the breast and has invaded the surrounding tissue. About 1 in 10 invasive breast cancer is an ILC. ILC is treated by surgery to excise the cancerous tissue, and radiation therapy. In addition, chemotherapy and immunotherapy combination (e.g., tamoxifen and tratuzumab) is often used as an adjuvant therapy to treat ILC.

Inflammatory breast cancer accounts for about 1% to 3% of all breast cancers. In inflammatory breast cancer, cancer cells block lymph vessels in the skin, resulting in the beast turning red and feeling warm. The affected breast may become larger or firmer, tender, or itchy. Inflammatory breast cancer is treated with chemotherapy, immunotherapy, radiation therapy and in some cases, surgery.

Estrogen Receptor positive (ER+) breast cancer is characterized by the presence of estrogen receptors on the surface of the cancerous cells. Growth of ER+ cancer cells is associated with the availability of estrogen (hormone-dependent or hormone sensitive breast cancer). Approximately, 80% of all breast cancers are ER+ breast cancers. Treatment options for ER+ breast cancer include chemotherapeutic agents that block estrogen (e.g., tamoxifen).

The present disclosure relates to methods of manufacturing stable preparations of (Z)-endoxifen free base, mixtures of (E)-endoxifen and (Z)-endoxifen (E/Z-mix), and salts thereof, and uses thereof. The present disclosure further relates to oral compositions comprising (Z)-endoxifen or salts thereof and methods of treating a subject in need thereof. The present disclosure also provides methods of treating a subject having or at risk of having a hormone-dependent breast disorder, a hormone-dependent reproductive tract (gynecologic) disorder, or both by administering to the subject an oral composition comprising (Z)-endoxifen, E/Z-mix, or a salt thereof.

In an aspect, the present disclosure relates to oral compositions comprising endoxifen or salts thereof. Endoxifen comprised in compositions of the present disclosure may be (Z)-endoxifen, (E)-endoxifen or a combination thereof. In one aspect, the present disclosure relates to compositions comprising stable (Z)-endoxifen free base.

In one aspect, the present disclosure provides industrially scalable methods of making (Z)-endoxifen free base, mixtures of (E)-endoxifen and (Z)-endoxifen (E/Z-mix), and salts thereof. In an aspect, the industrially scalable methods are synthetic methods of making stable (Z)-endoxifen free base, E/Z-mix, and salts thereof. In another aspect, the present disclosure provides methods of making compositions comprising stable (Z)-endoxifen free base, E/Z-mix, and salts thereof.

In certain aspects, the present disclosure provides crystalline forms of (Z)-endoxifen free base and crystalline forms of mixtures of (E)-endoxifen and (Z)-endoxifen, as well as pharmaceutical compositions of endoxifen comprising the crystalline forms described herein.

Synthesis of (Z)-Endoxifen Free Base

Several methods for the synthetic preparation of endoxifen are known in the art. For e.g., methods of synthetic preparations of endoxifen and their prodrugs and salts are described in U.S. Pat. No. 9,333,190 (Ahmad, Jina Pharmaceuticals); WO 2008/070463 (Ahmad, Jina Pharmaceuticals), U.S. Pub. No. 2010/0112041 (Ahmad, Jina Pharmaceuticals), WO 2012/050263 (Ahmad, Jina Pharmaceuticals), WO 2014/141292 (Desai, Intas Pharmaceuticals), WO 2017/070651 (USA/Alchem Lab. Corp.); WO 2009/120999A2 (Kushner), U.S. Pat. No. 8,063,249 (Kushner, Olema Pharmaceuticals), U.S. Pat. Nos. 7,531,578 and 8,119,695 (Forman and Yu), and WO 2012/050263 (Song, CJ Cheiljedang Corp).

Methods of synthetic preparation of endoxifen have also been published in research literature. (Gauthier et al., J. Org. Chem, 61, 3890-3893 (1996), Fauq et al., Bioorg Med Chem Lett. 2010 May 15; 20(10):3036-3038); Stearns et al., J. Natl. Cancer Inst. Vol 95, No. 23, 2003; Johnson et al., Breast Cancer Research and Treatment. 85:151-159, 2004; Ogawa, et al. Chem. Pharm. Bull. 39, 911-916, 1991). However, there remains an unmet need for large scale industrial scalable manufacturing. Stable (Z)-endoxifen free base may be prepared accordance to Schema 1 as further described below and in Examples 1 to 9.

Schema 1. Synthesis of (Z)-endoxifen Free Base

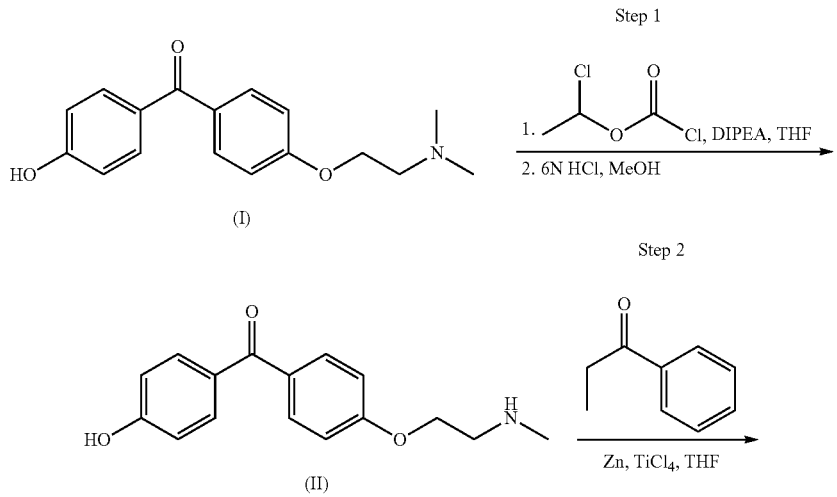

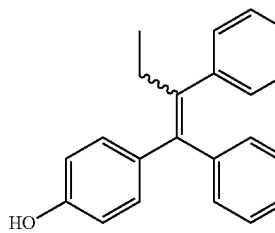

(E/Z)-endoxifen (III)

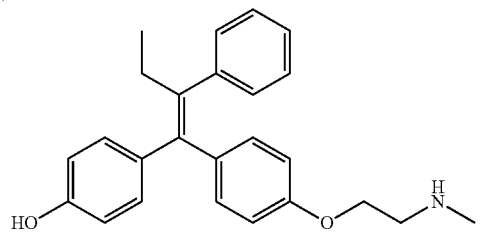

Step 3
1. EtOAc, HCl
2. EtOAc Crystallization
3. IPA hot slurry (Z)-endoxifen (IV)

Demethylation

In one aspect, the present disclosure relates to an industrially scalable process of making substantially purified (Z)-endoxifen free base, E/Z-mix, or salts thereof comprising demethylating the compound of Formula (I), [4-[2-(dimethylamino)ethoxy]phenyl](4-hydroxyphenyl)methanone), (available from AstaTech Pharmaceuticals, Inc., China) to form the compound of Formula (II). Accordingly, in some embodiments, the industrial process comprises preparing the compound of Formula (II) by demethylating [4-[2-(dimethylamino)ethoxy]phenyl](4-hydroxyphenyl) methanone) with a demethylating agent and a proton acceptor in an inert organic solvent to form the compound of Formula (II). The industrially scalable process for making the compound of Formula (II), (Z)-endoxifen free base, E/Z-mix, or salts thereof comprises demethylating the compound of Formula (I) in amounts ranging from 1 mg to 1000 kg per reaction.

In some embodiments, the compound of Formula (I) can be demethylated by reacting the compound of Formula (I) with a demethylating agent. The demethylating agent is any agent suitable for the purpose. Examples of suitable demethylating agents include N-iodosuccinamide (NIS), ethyl chloroformates (such as 1-chloroethyl chloroformate, dichloroethyl chloroformate, trichloroethyl chloroformate, α-Chloroethylchloroformate (ACE-Cl)), vinyl chloroformate (VO-Cl), cynogen bromide (BrCN: von Braun's reaction), diethyl azodicarboxylate, pyridinium chloride, and the like.

In some embodiments, the demethylating agent is a chloroformate selected from the group consisting of 1-chloroethyl chloroformate, dichloroethyl chloroformate, trichloroethyl chloroformate, α-Chloroethylchloroformate (ACE-Cl), and vinyl chloroformate (VO-Cl). In other embodiments, the demethylating agent is an ethyl chloroformate selected from the group consisting of selected from the group consisting of ethyl chloroformates, such as 1-chloroethyl chloroformate, dichloroethyl chloroformate, trichloroethyl chloroformate, and α-Chloroethylchloroformate (ACE-Cl). In at least one embodiment, the demethylating agent is 1-chloroethyl chloroformate.

In some embodiments, a demethylating agent is added to the reaction mixture at a wt/wt ratio of the compound of Formula (I) to demethylating agent ranging from 1:0.5 to 1:10. In other embodiments, the demethylating agent is present at ratios (wt/wt) of the compound of Formula (I) to demethylating agent ranging from 1:2: to 1:5. In at least one embodiment, the demethylating agent is present at a ratio (wt/wt) of the compound of Formula (I) to demethylating agent of 1:2. In at least one embodiment, demethylating agent is present at a ratio (wt/wt) of the compound of Formula (I) to demethylating agent of 1:3.3. In other embodiments, the demethylating agent 1-chloroethyl chloroformate is present at a ratio (wt/wt) of the compound of Formula (I) to demethylating agent ranging from 1:0.5 to 1:10.

The demethylation reaction can be carried out in an inert organic solvent suitable for the demethylation reaction in the presence of a proton acceptor. Such inorganic solvents include dichloromethane, dichloroethane, chloroform, carbon tetrachloride, chlorobenzene, diethyl ether, 1,4-dioxane, tert-butyl methyl ether (TBME), tetrahydrofuran (THF), N,N-dimethylformamide (DMF), N-methylpyrrolidone (NMP), diglyme, nitromethane, 1,2-dimethoxyethane (DME), pyridine, acetone, acetonitrile, benzene, o-xylene, m-xylene, p-xylene, xylenes, hexanes, cyclohexane, heptane, octane, nonane, and decane, or a combination thereof. In an aspect, the industrially scalable process comprises one or more inert organic solvents for demethylation at a (wt/wt) ratio of the compound of Formula (I) to inert organic solvent ranging from 1:1 to 1:50. In some embodiments, the demethylation solvent is THF at a ratio of the compound of Formula (I) to THF (wt/wt) ranging from 1:1 to 1:50. In other embodiments, the THF is present in ratios (wt/wt) of the compound of Formula (I) to THF ranging from 1:1 to 1:20.

Proton acceptors suitable for the purpose of the present disclosure include, but are not limited to carbonates, such as sodium carbonate and potassium carbonate, and bicarbonates, such as sodium bicarbonate and potassium bicarbonate, proton sponge, and ethyldiisopropylamine, (N',N-diisopropyleamine, "DIPEA"). In an aspect, the industrially scalable process comprises a proton acceptor added to the reaction mixture at a wt/wt ratio of the compound of Formula (I) to proton acceptor ranging from 1:0.5 to 1:10. In some embodiments, the proton acceptor is present in a ratio (wt/wt) of the compound of Formula (I) to proton acceptor of 1:1:8.

One of skill in the art will be readily able to determine other solvents and proton acceptors known in the art suitable for demethylation reaction of the present disclosure.

Demethylating agents, solvents for demethylation reaction, and the compound of Formula (I) may be added in any order. Each reagent may be added to a suitable reactor in a single bolus or in multiple boluses and stirred.

In some embodiments, the compound of Formula (I) is charged to a suitable reactor to which inert organic solvent THF and proton acceptor DIPEA are added for demethylation reaction, and cooled to 0° C. to 20° C., followed by addition of one or more demethylating agents. THF is added at a wt/wt ratio of 1:1 to 1:20, and proton acceptor DIPEA is added at a wt/wt ratio of 1:0.5 to 1:10 to the demethylation reaction mixture, where wt/wt is with respect to the compound of Formula (I). In some embodiments, the reaction mixture is cooled to not more than (NMT) 15° C. followed by slow addition of one or more demethylating agents. The reaction may be carried out under inert conditions, such as under nitrogen or argon.

The reaction mixture comprising the compound of Formula (I), one or more demethylating agents (for example, 1-chloroethyl chloroformate) in one or more inert organic solvents can be heated at temperature ranging from 20° C. to 250° C., such as from 40° C. to 80° C., from 50° C. to 230° C., from 50° C. to 120° C., and from 150° C. to 200° C. In some embodiments, the reaction mixture is heated under reflux. In other embodiments, the compound of Formula (I) is reacted with demethylating agent and proton acceptor for not less than (NLT) 5 hours, NLT 8 hours, NLT 12 hours, NLT 24 hours, NLT 36 hours, NLT 48 hour and NLT 72 hours. In at least one embodiment, the reaction is heated under reflux NLT 12 hours. The reaction may be held and stored until further use. In some embodiments, the reaction mixture is held not more than (NMT) 24 hours under reflux conditions while stirring.

The mixture can be subjected to one or more rounds of distillation under reduced pressure. Distillation may be carried out at NMT 100° C., at NMT 95° C., at NMT 90° C., at NMT 85° C., at NMT 80° C., or at NMT 70° C. with solvents suitable for distillation such as ethyl acetate, lower alcohols (non-limiting examples include methanol, ethanol, n-propanol, and isopropanol), benzene, acetone, acetonitrile, toluene, dichloromethane, 1,2-dichloroethane, and chloroform. One of skill in the art will be able to readily determine additional suitable solvents useful for the purpose.

In at least one embodiment, the solvent used for distillation is methanol. As a non-limiting example, methanol may be used for solvent swap for 2 to 5 rounds of distillation under reduced pressure.

Solvents, such as methanol, may be used for distillation at a (wt/wt) ratio of the compound of Formula (I) to solvent ranging from 1:1 to 1:10 per round of distillation.

Then, the mixture can be reacted with a solvent/acid mixture by addition of an acid (wt/wt ratio of the compound of Formula (I) to acid ranging from 1:1 to 1:10) to the solvent while stirring and heating under reflux. The acid can be any suitable acid. HCl is an example of acid suitable for the purpose of the present disclosure. Non-limiting examples of suitable solvent/acid mixtures include methanol/HCl, ethanol/HCl, propanol/HCl, isopropanol/HCl, methanol/sulfuric acid, methanol/phosphoric acid, ethanol/sulfuric acid, ethanol/phosphoric acid, propanol/sulfuric acid, propanol/phosphoric acid, isopropanol/sulfuric acid, isopropanol/phosphoric acid, methanol/acetic acid, ethanol/acetic acid, propanol/acetic acid, isopropanol/acetic acid, methanol/formic acid, ethanol/formic acid, propanol/formic acid, and isopropanol/formic acid. In at least one embodiment, the solvent/acid mixture is methanol/6N HCl. As a non-limiting example, methanol in methanol/HCl mixture may be added at a wt/wt ratio of the compound of Formula (I) to methanol in solvent/acid mixture at 1:3.2 while HCl in the methanol/HCl mixture may be at a wt/wt ratio of the compound of Formula (I) to HCl in the solvent/acid mixture at 1:4. In at least one embodiment, the methanol/6N HCl mixture is added at a wt/wt ratio of the compound of Formula (I) to methanol/6N HCl ranging from 1:1 to 1:10, such as 1:1 to 1:5.

Distillation may be carried out for NLT 5 hours, NLT 8 hours, NLT 10 hours, NLT 12 hours, NLT 14 hours under reduced pressure. Distillation may be carried out at a temperature NMT 70° C., NMT 75° C., NMT 80° C., NMT 85° C., NMT 90° C. and NMT 90° C.

The reaction mixture may be held and stored until further use. In some embodiments, the reaction mixture may be held for NMT 24 hours under reflux conditions while stirring.

The reaction mixture can be neutralized with a neutralizing agent such as sodium hydroxide (NaOH), ammonium hydroxide, aminomethylpropanol and the like, and filtered. The resulting wet cake can be washed with water and an organic solvent such as ethyl acetate (EtOAc) to obtain (4-hydroxyphenyl)(4-(2-(methylamino)ethoxy)phenyl) methanone, the compound of Formula (II).

The neutralizing agent may be at a wt/wt ratio of the compound of Formula (I) to the neutralizing agent ranging from 1:1 to 1:10. In some embodiments, the neutralizing agent is 8N sodium hydroxide at a ratio ranging from 1:1 to 1:10. In other embodiments, the neutralizing agent is 8N sodium hydroxide at a ratio ranging from 1:2 to 1:8.

In another aspect, the industrially scalable process for making (Z)-endoxifen free base, E/Z-mix or salts thereof comprises one or more steps of washing filtered product (the compound of Formula (II)) with purified water (1:1 to 1:5 wt/wt) and organic solvents such as ethyl acetate (EtOAc) (1:0.5 to 1:10 wt/wt) wherein the wt/wt is with respect to the compound of Formula (I). The wet cake is dried under reduced pressure/vacuum. The temperature for can range from 25° C. to 60° C. In some embodiments, the drying is carried out at a temperature NMT 50° C.

McMurry Reaction

In another aspect, the present disclosure relates to an industrially scalable process of making (Z)-endoxifen free base, E/Z-mix, and salts thereof comprising subjecting the compound of Formula (II) to a McMurry reaction to afford an E/Z-mix (i.e., a mixture of (E)-endoxifen and (Z)-endoxifen free bases), compounds of Formula (III).

The McMurry reaction has been used to prepare tamoxifen (European Patent Application No. 168175). The present disclosure relates to an industrially scalable process wherein the compound of Formula (II), (4-hydroxyphenyl)(4-(2-(methylamino)ethoxy)phenyl) methanone, is coupled to propiophenone mediated by a McMurry reaction via titanium salts such as chloride salts of titanium (for example, titanium trichloride and titanium tetrachloride ($TiCl_4$)) and reducing agents in inert organic solvents to form an E/Z mix of compounds of Formula (III).

Salts of titanium that are useful for the present disclosure include titanium halides (such as titanium trichloride ($TiCl_3$), Titanium tetrachloride ($TiCl_4$), titanium iodides, titanium bromides, and titanium fluorides), titanium (IV)

trichloride isopropoxide, and titanium isopropoxide. In some embodiments, the titanium salt is $TiCl_4$. Titanium salts, such as $TiCl_4$, are added at a wt/wt ratio of the compound of Formula (II) to titanium salt ranging from 1:0.1 to 1:12.

Reducing agents include zinc, zirconium, vanadium, niobium, molybdenum, tungsten, aluminum, magnesium, potassium, zinc-copper couple, alkali and alkali earth metals, butylium, lithium, and lithium aluminum hydride. In at least one embodiment, the reducing agent is zinc. The McMurry synthesis is conveniently carried out using a reducing agent such as zinc at a wt/wt ratio of the compound of Formula (II) to reducing agent ranging from 1:0.1 to 1:10. In some embodiments, the ratio of reducing agent is in excess compared to titanium salts.

The McMurry synthesis can be carried out in one or more inert organic solvents. Inert organic solvents useful for the McMurry reaction include dichloromethane, dichloroethane, chloroform, carbon tetrachloride, chlorobenzene, diethyl ether, 1,4-dioxane, tert-butyl methyl ether (TBME), tetrahydrofuran (THF), N,N-dimethylformamide (DMF), N-methylpyrrolidone (NMP), diglyme, nitromethane, 1,2-dimethoxyethane (DME), pyridine, acetone, acetonitrile, benzene, o-xylene, m-xylene, p-xylene, xylenes, hexanes, cyclohexane, heptane, octane, nonane, and decane, or a combination thereof. In some embodiments, the inert organic solvent is at wt/wt ratio of the compound of Formula (II) to solvent ranging from 1:1 to 1:50. In other embodiments, the inert organic solvent is at wt/wt ratios of the compound of Formula (II) to solvent ranging from 1:1 to 1:20. In some embodiments, the inert organic solvent used for the McMurry reaction is THF. THF, in some embodiments, is at wt/wt ratio of the compound of Formula (II) to THF ranging from 1:1 to 1:20.

It is advantageous to combine titanium salts and reducing agent in the inert organic solvents to create a pre-mix. Titanium salts are added to the reducing agent and inert organic solvents at such a rate so as to keep the internal temperature at NMT 75° C., such as NMT 65° C., NMT 55° C., NMT 45° C., NMT 40° C., NMT 35° C., NMT 30° C., NMT 25° C., NMT 20° C., and NMT 15° C. Accordingly, titanium salts and reducing agent in the inert organic solvents are combined to create a pre-mix. In some embodiments, Zn, $TiCl_4$ and THF are combined to create $Zn/TiCl_4/$THF mixture. In at least one embodiment, $TiCl_4$ is added to Zn and THF and mixed keeping the internal temperature NMT 20° C. for NLT 10 min.

Preparation of titanium salt and a reducing agent in an inert organic solvent may further comprise heating titanium salt and reducing agent in an inert organic solvent to a temperature ranging from 20° C. to 250° C., such as from 40° C. to 80° C., from 50° C. to 230° C., from 50° C. to 120° C., and from 150° C. to 200° C. In some embodiments, titanium salt and reducing agent present in an inert organic solvent are heated at NLT 60° C. In some embodiments, preparation of titanium salt and a reducing agent in an inert organic solvent further comprises heating titanium salt and reducing agent in an inert organic solvent under reflux. Titanium salt and reducing agent in inert organic solvent are heated under reflux for NLT 30 min, such as NLT 1 hour, NLT 2 hours, NLT 4 hours, NLT 6 hours and NLT 8 hours, under inert conditions such as under N2 or argon.

It is also advantageous to pre-mix the compound of Formula (II) with inert organic solvent such as THF and propiophenone and then reacting the compound of Formula (II) to pre-mixed reducing agent/titanium salt/solvent mixture such as a $Zn/TiCl_4/THF$ mixture to form a mixture of (E)-endoxifen and (Z)-endoxifen, compounds of Formula (III). Propiophenone can be added at a wt/wt ratio of the compound of Formula (II) to propiophenone ranging from 1:0.01 to 1:5. Inert organic solvent can be at a wt/wt ratio of the compound of Formula (II) to solvent ranging from 1:1 to 1:20. The compound of Formula (II) of step (a) is reacted with titanium salt and a reducing agent in an organic solvent under reflux for NLT 0.5 hours, NLT 1 hour, NLT 2 hours, NLT 4 hours, NLT 6 hours, NLT 8 hours, NLT 12 hours, NLT 24 hours, and NLT 48 hours. In at least one embodiment, the compound of Formula (II) is mixed with THF and propiophenone and reacted to a pre-mixture of Zn, $TiCl_4$, THF and heat under reflux for NLT 2 hours. In another embodiment, the compound of Formula (II) is mixed with THF and propiophenone and reacted to the $Zn/THF/TiCL_4$ mixture as described above and heated under reflux for NLT 8 hours. The reaction mixture may then be allowed to cool to 0° C. to 35° C.

The mixture of (E)-endoxifen and (Z)-endoxifen in the reaction mixture can be then subjected to extractive purification, distillation and crystallization to afford a purified mixture of (E)-endoxifen and (Z)-endoxifen. The mixture of (E)-endoxifen and (Z)-endoxifen in the reaction mixture can be subject to extractive purification by extracting with inert organic solvents, such as THF and MeTHF, or by addition of salts, such as potassium carbonate, ammonium chloride, sodium chloride, sodium hydroxide, to the reaction mixture and extraction with an inert organic solvent, such as THF and MeTHF.

In some embodiments, the reaction mixture is extracted one or more times with ammonium chloride, such as 25% ammonium chloride (1:1 to 1:30 wt/wt); silica (Celite®) bed (1:0.01 to 1:5 wt/wt); and/or solvent, such as THF (1:1 to 1:10 wt/wt). In other embodiments, the reaction mixture is extracted one or more times with potassium carbonate ($K_2CO_3$), such as 40% $K_2CO_3$ (1:1 to 1:10 wt/wt) and MeTHF (1:1 to 1:10 wt/wt). In some embodiments, the E/Z mixture may be further extracted with NaOH, such as 1N NaOH (1:1 to 1:20 wt/wt). In at least one embodiment, NaCl (1:0.1 to 1:0.5 wt/wt) may be added to 1N NaOH for the extraction step.

In some embodiments, the reaction mixture may be further extracted one or more times with THF or MeTHF. In at least one embodiment, the reaction mixture is extracted 3 or more times with MeTHF. The applicants have found MeTHF to be surprisingly suitable for the step of extraction of a mixture of (E)-endoxifen and (Z)-endoxifen, affording higher yields of purified mixtures of (Z)-endoxifen and (E)-endoxifen. In at least one embodiment, the mixture may be still further extracted with 20% sodium chloride (1:1 to 1:10 wt/wt).

The reaction mixture can be next subjected to 2 to 5 rounds of solvent swap and distillation with a suitable solvent, such as ethyl acetate, IPA, and IPA/PPW (1:1 to 1:10 wt/wt with respect to the compound of Formula (III)). Distillation may be carried out under reduced pressure/vacuum at temperatures ranging from 30° C. to 90° C. In some embodiments, the distillation may be performed at temperature NMT 30° C., NMT 35° C., NMT 40° C., NMT 45° C., NMT 50° C., NMT 55° C., NMT 60° C., NMT 65° C., NMT 70° C., NMT 75° C., NMT 80° C. and NMT 90° C., and filtered. The filtered product may be washed with solvents such as EtOAc, IPA, IPA/PPW or n-heptane and then crystallized with crystallization systems such as EtOAc/n-heptane (1:2 v/v) or IPA/n-heptane (1:2.7 v/v) at a wt/wt ratio of a compound of Formula (III) to EtOAc/n-heptane or IPA/n-heptane ranging from 1:1 to 1:20 and dried, for example, at NMT 60° C., to afford a crystalline solid mixture of (E)-endoxifen and (Z)-endoxifen free bases, compounds of Formula (III).

In yet another aspect, the present disclosure relates to an industrially scalable method of manufacturing or reequilibriating an E/Z-mix having an E/Z ratio of approximately 1:1 (45:55 to 55:45). A suitable reactor may be charged with the compounds of Formula (III) dissolved in an inert organic solvent, such as ethyl acetate, prepared in a McMurry reaction as described above. The compounds of Formula (III) can have an E/Z ratio of 99:1 to 60:40. The mixture can be concentrated at temperatures ranging from 40° C. to 85° C. In some embodiments, the mixture is concentrated at temperature NMT 75° C. until the volume reaches 5 vol. The mixture is heated to reflux and then cooled to temperatures ranging from 40° C. to 60° C. In some embodiments, the temperature of the mixture is cooled to 50±5° C. n-heptane, at a ratio of the compounds of Formula (III) to n-heptane ranging from 1:1 to 1:20, may be added slowly to the mixture and the mixture may be then cooled to 0±5° C. The mixture may be stirred at 0±5° C. for NLT 0.5 hours, such as NLT 1 hour, NLT 2 hours, NLT 4 hours, NLT 8 hours, NLT 12 hours or NLT 24 hours. The mixture may be filtered and washed with ethyl acetate/n-Heptane (1:2 v/v) at a wt/wt ratio of the compounds of Formula (III) to ethyl acetate/n-heptane ranging from 1:1 to 1:10. The wet cake may be dried under reduced pressure to afford E/Z-endoxifen mixture having an E/Z-ratio of approximately 1:1. Drying may be carried out at temperatures ranging from 30° C. to 70° C. In at some embodiments, the wet cake is dried under reduced pressure or vacuum at NMT 60° C. to afford E/Z-endoxifen mixture having an E/Z-ratio of approximately 1:1 (45:55 to 55:45).

In still another aspect, the compounds of Formula (III) may be further purified or enriched or reequilibrated to obtain substantially pure (Z)-endoxifen as described below.

Enrichment Purification of (Z)-Endoxifen Free Base

In still another aspect, the present disclosure relates to industrially scalable methods of manufacturing by enrichment and purification (Z)-endoxifen free base. Industrially scalable enrichment and purification of (Z)-endoxifen may be carried out as described herein using the method of Step 3 of exemplary Schema 1, and as further described in Examples 1, 2, 4, and 9. The starting mixture of (E)-endoxifen and (Z)-endoxifen used for fractional crystallization can have any E/Z ratio, for example, E/Z ratio ranging from 99:1 to 1:10. In some embodiments, the E/Z-ratio of the starting (E)/(Z)-endoxifen mixtures ranges from 30:70 to 70:30. In some embodiments, the E/Z-ratio of the starting (E)/(Z)-endoxifen mixtures ranges from 99:1 to 1:99. In some embodiments, the E/Z-ratio of the starting (E)/(Z)-endoxifen mixtures is 51:1, 1:1.8 or 1:5.6.

The E/Z-mix can be the compounds of Formula (III) obtained as described above or it can be commercially sourced (for example, from Sigma-Aldrich). A mixture of (E)-endoxifen and (Z)-endoxifen (E/Z-mix) is subjected to fractional crystallization to obtain a first crystalline solid and a first mother liquor enriched with (Z)-endoxifen free base (Example 1). Fractional crystallization is carried using a first solvent which is capable of triturating endoxifen and its derivatives such that (Z)-endoxifen tends to remain in filtrate. Suitable first solvents are those that differentially solubilize the endoxifen isomers, and include, without limitation, ethyl acetate, isopropanol, isopropanol/PPW, acetonitrile, acetonitrile/PPW, and dichloromethane. In some embodiments, the first solvent is ethyl acetate. The first solvent, for example, ethyl acetate, is added at a wt/wt ratio of the compounds of Formula (III) to first solvent ranging from 1:1 to 1:20. In some embodiments, the the compounds of Formula (III) are dissolved in first solvent, and heated to a temperature ranging from 50° C. to 80° C. and cooled to NMT 35° C.

It has been a surprising discovery that acidification of the mixture enhances the conversion of (E)-endoxifen to (Z)-endoxifen. Accordingly, in some embodiments, the compounds of formula (III) are pretreated with an acid and then neutralized with a base.

As a non-limiting example, a suitable reactor is charged with the compounds of Formula (III) to which first solvent is added and cooled to 0° C.-5° C. Next, an acid such as HCl or TFA may be added slowly. In some embodiments, the acid is added to the E/Z-endoxifen mixture at a wt/wt ratio of the compounds of Formula (III) to acid ranging from 1:1 to 1:5. The reaction mixture may then be heated at temperatures ranging from 50° C. to 70° C. while stirring. In some embodiments, the reaction is carried out under reflux. The reaction may be carried out for NLT 4 hours, such as NLT 6 hours, NLT 12 hours, NLT 24 hours, and NLT 48 hours. The reaction mixture is cooled to 0° C.-5° C. and neutralized with a neutralizing agent.

In some embodiments, the neutralizing agent is added to the reaction mixture at a wt/wt ratio of the compounds of Formula (III) to neutralizing agent ranging from 1:1 to 1:5. Suitable neutralizing agents include sodium hydroxide, potassium hydroxide, ammonium hydroxide, aminomethylpropanol, and the like. In some embodiments, the neutralizing agent is 8N sodium hydroxide. The pH of the reaction mixture is preferably alkaline. In some embodiments, the pH is ≥10, such as ≥11 or ≥12.

In some embodiments, (Z)-endoxifen is extracted into the organic layer and collected, and the aqueous phase is washed one or more times with the first solvent such as ethyl acetate (added at a wt/wt ratio of the compounds of Formula (III) to first solvent ranging from 1:1 to 1:10). The organic layers are pooled, and washed one or more times with brine (20% NaCl; added at a wt/wt ratio of the compounds of Formula (III) to NaCl ranging from 1:1 to 1:10). The organic layer is treated with activated carbon and filtered over silicon dioxide (Celite®) bed (added at a wt/wt ratio of the compounds of Formula (III) to silica ranging from 1.01 to 1:0.1). The product is washed again one or more times with first solvent (added at a wt/wt ratio of the compounds of Formula (III) to first solvent ranging from 1:1 to 1:10), and distilled. Distillation may be carried out at temperatures ranging from 50° C. to 80° C. In some embodiments, the temperature may be NMT 75° C.

The first mother liquor is enriched in (Z)-endoxifen as seen in Example 1 and Tables 2 and 3. In some embodiments, the first mother liquor is enriched by at least 50% as compared to with the E/Z-ratio of the mixture of E-endoxifen and Z-endoxifen. In other embodiments, the first mother liquor is enriched in (Z)-endoxifen by at least 70% as compared to the E/Z-ratio of the mixture of E-endoxifen and Z-endoxifen.

The first mother liquor may be subjected to recrystallization by concentrating the first mother liquor, or swapping out the first solvent from the first mother liquor one or more times to obtain second crystalline solid and a second mother liquor (Table 5). Recrystallization is carried out using a second solvent for swapping. The second solvent is added at a wt/wt ratio of the compounds of Formula (III) to second solvent ranging from 1:1 to 1:10 to create a slurry. Suitable second solvents include IPA, IPA/PPW, acetone, acetone/MTBE, ethanol, EtOAc, EtOAc/n-heptane. In some embodiments, the second solvent is IPA. Surprisingly, IPA has been found to triturate (Z)-endoxifen into solid fraction at levels higher than EtOAc. Accordingly, in some embodiments, when the first solvent is EtOAc, the second solvent is IPA or IPA/PPW. This is useful in directing (Z)-endoxifen first into the filtrate (first mother liquor) from EtOAc, and then into the solid fraction from IPA or IPA/PPW. In at least one embodiment, the second solvent is IPA/PPW (Table 7). In yet another embodiment, the second solvent is acetone/MTBE. The second crystalline solid is (Z)-endoxifen, (Z)-4-(1-(4-(2-(methylamino)ethoxy)phenyl)-2-phenylbut-1-enyl)phenol, the compound of Formula (IV). (Molecular weight 373.49; Molecular formula: $C_{25}H_{27}NO_2$; Melting point 139° C.-143° C. The second crystalline solid is ≥70% (Z)-endoxifen, such as ≥75% (Z)-endoxifen, ≥80% (Z)-endoxifen or ≥90% (Z)-endoxifen. In some embodiments, the second crystalline solid is ≥90% (Z)-endoxifen.

The second crystalline solid may optionally be subjected to recrystallization to obtain a third crystalline solid, (Z)-endoxifen (Table 5). The third crystalline solid may be ≥90% (Z)-endoxifen, such as ≥91% (Z)-endoxifen, ≥92% (Z)-endoxifen, ≥93% (Z)-endoxifen, ≥94% (Z)-endoxifen, ≥95% (Z)-endoxifen, ≥96% (Z)-endoxifen, ≥97% (Z)-endoxifen, ≥98% (Z)-endoxifen, or ≥99% (Z)-endoxifen. In some embodiments, the third crystalline solid is ≥90% (Z)-endoxifen. In some embodiments, the third crystalline solid is ≥95% (Z)-endoxifen. This optional recrystallization is carried out using a third solvent. The third solvent is selected from the group consisting of ethanol, methanol, ethyl acetate, IPA, IPA/PPW, acetone, acetone/MTBE and EtOAc/n-heptane.

In an aspect, the present disclosure relates to pre-heating first solvent, second solvent, and third solvent prior to use (Table 2). In some embodiments, one or more of the first solvent, second solvent, and third solvent can each be independently preheated to a temperature ranging from 40° C. to 80° C. Fractional crystallization and recrystallization steps may also include steps of distilling at 60° C. to 80° C. and/or cooling the resulting solution to a temperature ranging from 0° C. to 35° C.

It is to be understood that in some embodiments, first, second, and third crystalline solids as well as the second mother liquor obtained as described above may be further subjected to fractional crystallization and recrystallization as described above one or more time to obtain purified (Z)-endoxifen. It is also to be understood that first, second, and/or third crystalline solids obtained may be optionally reprocessed using column chromatography techniques to obtain more (Z)-endoxifen.

In certain embodiments, the industrially scalable methods described herein independently comprises additional steps or procedures (e.g., to remove reaction by-products, or to workup, isolate or purify reaction products) as detailed in examples herein. In some embodiments, the (Z)-endoxifen free base has <2%, <1%, and <0.5% impurity. In other embodiments, the compounds of Formula (III) have <2%, <1%, and <0.5% impurity.

A person of skill in the art will recognize several parameters of the foregoing process that may be varied in order to obtain a desirable outcome. These parameters include for example, the methods and means of purification of reaction components and solvents; the order of addition of said reaction components and solvents to the reaction mixture, duration of reaction of said reaction components and solvents; and temperature and rate of stirring, mixing or agitation of the reaction components and solvents during the reactions.

It was found that the process embodied by the methods herein (also including the particular process steps) fulfills one or more of the following criteria: better stability, safer, simpler, higher yielding and more economical when compared with the known processes for manufacturing compounds of Formula (II), (III) and (IV). (Z)-Endoxifen prepared by the processes disclosed below is stable for at least 9 months at 5° C. and 25° C. at 60% relative humidity (25° C./60% RH) and for at least 3 moths at 40° C./75% RH (Example 9). Stability at elevated temperatures is indicative of long term stability. Accordingly, (Z)-endoxifen free base prepared by the processes of the present disclosure are stable for at least 6 months, such as for at least 9 months, at least 12 months, or at least 18 months. Further, the process described herein is considered scalable in multi-kilogram operations, making it suitable for commercial production.

Endoxifen Salts

In still another aspect, the present application provides endoxifen salts and methods of making endoxifen salts. Endoxifen salts known in the art include hydrochloride (Fauq et al., Bioorg Med Chem Lett. 2010 May 15; 20(10): 3036-3038) and citrate salts of endoxifen (U.S. Pat. No. 9333190; U.S. Publication No. 2010/0112041) and are being evaluated for oral administration to subjects.

In certain embodiments, the present disclosure provides anion salts of endoxifen selected from the group consisting of arecoline, besylate, bicarbonate, bitartarate, butylbromide, citrate, camysylate, gluconate, glutamate, glycollylarsanilate, hexylresorcinate, hydrabamine, hydrobromide, hydrochloride, hydroxynapthanoate, isethionate, malate, mandelate, mesylate, methylbromide, methylbromide, methylnitrate, methylsulfate, mucate, napsylate, nitrate, pamaoate (Embonate), pantothenate, phosphate/diphosphate, polygalacuronate, salicylate, stearate, sulfate, tannate, Teoclate, and triethiodide.

In other embodiments, the present disclosure provides cation salts of endoxifen selected from the group consisting of benzathine, clemizole, chloroprocaine, choline, diethylamine, diethanolamine, ethylenediamine, meglumine, piperazine, procaine, aluminum, barium, bismuth, lithium, magnesium, potassium, and zinc.

The endoxifen salts of the present disclosure may be made using any of the compounds of Formulae (I), (II), (III) and (IV), prepared as described above.

Endoxifen Gluconate

In some embodiments, the present disclosure provides a gluconate salt of endoxifen, or a chemical equivalent thereof. Accordingly, in at least one embodiment, the endoxifen comprised in a composition of the present disclosure is an endoxifen gluconate or a chemical equivalent thereof. Unless specified otherwise, it will be understood that when referring to endoxifen gluconate herein, its chemical equivalents will also be encompassed.

For the purposes of the present disclosure, chemical equivalents of endoxifen gluconate include all anionic, cationic, and non-ionic reaction complexes between the endoxifen molecule and the gluconate moiety. Such complexes typically react with the hydroxyl group of the endoxifen molecule. The gluconate moiety includes D-gluconic acid, gluconic acid, glycogenic acid, glycan-Δ-lactone, and the like. In some embodiments, the gluconate moiety is a pharmaceutically acceptable gluconate salt. Such salts include calcium gluconate, sodium gluconate, and salts of alkali metals and alkaline earth metals such as potassium gluconate, magnesium gluconate, lithium gluconate, and the like.

Both stereoisomers of gluconate, the D-form and the L-form, are embraced in the present disclosure. In some embodiments, endoxifen gluconate comprised in the compositions of the present disclosure is selected from the group consisting of (Z)-endoxifen D-gluconate, (Z)-endoxifen L-gluconate, (E)-endoxifen D-gluconate, (E)-endoxifen L-gluconate and combinations thereof. In some embodiments, the pharmaceutical composition comprises (Z)-endoxifen L-gluconate. In certain embodiments, the pharmaceutical composition comprises (Z)-endoxifen D-gluconate. The compositions may be present as racemic mixtures, pure stereoisomers (e.g., enantiomers and diastereoisomers), stereo-enriched mixtures and the like unless otherwise indicated. When a particular stereoisomer is shown or named herein, it will be understood by those skilled in the art that minor amounts of other stereoisomers may be present in the compositions of the present disclosure unless otherwise indicated, provided that the utility of the composition as a whole is not eliminated by the presence of such other isomers. Individual isomers may be obtained by numerous methods that are well known in the art, including chiral chromatography using a suitable chiral stationary phase or support, or by chemically converting them into diastereoisomers, separating the diastereoisomers by conventional means such as chromatography or recrystallization, then regenerating the original stereoisomer.

The present disclosure also includes methods of making endoxifen gluconate or a chemical equivalent thereof, which includes mixing endoxifen with a gluconate moiety to yield endoxifen gluconate. Methods of making gluconate salts of therapeutic agents are known in the art (for example, U.S. Publication No. 2002/0127665).

In some embodiments, an endoxifen D-gluconate (such as (Z)-endoxifen D-gluconate) salt may be obtained by mixing an ethanolic slurry of the endoxifen (such as (Z)-endoxifen prepared by the methods described above) as the free base with an aqueous solution of D-gluconic acid, obtained by hydrolyzing a 20% w/v solution of D-gluconolactone in water by heating at 70° C. for 15 to 30 min. In some embodiments, a minimum volume of ethanol is used and 5 ml of the aqueous D-gluconic acid solution is added per 1 g of endoxifen free base. Stirring is then continued until a clear solution is obtained. The required volume of this solution is then added to one or more of other excipients to produce formulations in which the "active ingredient" is (Z)-endoxifen D-gluconate or (Z)-endoxifen L-gluconate salt. The salt may be purified by any of the methods known in the art and disclosed herein.

Purified (Z)-endoxifen free base or a mixture of (E)/(Z)-endoxifen is both useful for the purpose of preparation of the endoxifen gluconate salt. A solution of (Z)-endoxifen D-gluconate or (Z)-endoxifen L-gluconate may also be purified from a mixture of (E)/(Z)-endoxifen gluconate salt as described herein by fractional crystallization or recrystallization (Examples 1-3) to obtain a solid purified (Z)-endoxifen salt. The solid salt may be stored at −5° C. under $N_2$ until further use.

It will be understood by those skilled in the art that other endoxifen salts can also be used as starting material with gluconate moiety or gluconate salts to yield endoxifen gluconate or chemical equivalents thereof.

Endoxifen gluconate or chemical equivalent thereof may be prepared as described above or with starting reactants that are readily available. For example, crude endoxifen HCl (≥98%) and sodium gluconate are readily available from Sigma-Aldrich, USA.

In some embodiments, endoxifen HCl and sodium gluconate are dissolved in a suitable solvent to yield endoxifen gluconate or a chemical equivalent thereof. In at least one embodiment, the composition comprising endoxifen gluconate also comprises endoxifen HCl. In other embodiments, an (E)/(Z)-endoxifen mixture (compounds of Formula (III)) and sodium gluconate are dissolved in a suitable solvent to afford endoxifen gluconate or a chemical equivalent thereof.

Suitable solvents for making endoxifen gluconate or chemical equivalents thereof include, but are not limited to, organic solvents such as alcohols, acetones, DMSO, polyethylene glycol, fatty acids and fatty alcohols and their derivatives, hydroxyl acids, pyrrolidones, urea, vegetable oils, animal oils such as fish oils, essential oils, and the like or mixtures thereof, and water-miscible solvents such as water miscible alcohols, dimethylsulfoxide, dimethylformamide, water-miscible ether, for example, tetrahydrofuran, water-miscible nitrile, for example acrylonitrile, a water miscible ketone such as acetone or methyl ethyl ketone, an amide such as dimethylacetamide, propylene glycol, glycerin, polyethylene glycol 400, glycofurol, tetraglycol, and the like, or mixtures thereof.

Water-miscible solvents useful for the preparation of endoxifen gluconate are glycerin, ethanol, propanol, isopropanol, propylene glycol, polyethylene glycols, or mixtures thereof. Additional solvents that are useful include diglycol monoethyl ether (transcutol); alkelene glycols, such as dipropylene glycol, propylene glycol, polyethylene glycols such as PEG 300, 400, 3395, 4450 and the like; dimethyl isosorbide; and dehydrated alcohol. In some embodiments, the solvent is a dehydrated alcohol, such as absolute alcohol. In certain embodiments, the amount of solvent is sufficient to dissolve the endoxifen (free base, salts) and gluconate salts. The concentration of the solvent can also be adjusted as needed. The reaction can be carried out at room temperature and at atmosphere of pressure.

The amount of endoxifen free base or endoxifen salt (such as endoxifen HCl and the like) and gluconate salt (such as and sodium gluconate and the like) that can be used to make endoxifen gluconate or chemical equivalent thereof can vary depending on the amount of reactants used. The resulting endoxifen gluconate will have endoxifen:gluconate moiety at 1:1 ratio.

In some embodiments, the amount of endoxifen or endoxifen salt used for making endoxifen gluconate is from 0.01% to 40% (e.g., from 1% to 10%, or from 3% to 5%) by weight of the total composition (wt/wt). In some embodiments, the gluconate salt used for making endoxifen gluconate is from 0.01% to 40% (wt/wt) (e.g., from 1% to 10% (wt/wt), or from 3% to 5% (wt/wt)). One of skill in the art will be guided by skill and knowledge in the field and the present disclosure, including without limitation, amounts of reactants which are effective to achieve the desired yields.

Crystalline Forms

In certain aspects, the present disclosure provides crystalline forms of endoxifen, including crystalline forms of (Z)-endoxifen free base and crystalline forms of mixtures of (E)-endoxifen and (Z)-endoxifen. The present disclosure further provides pharmaceutical compositions of endoxifen comprising the crystalline forms described herein. A crystalline form of endoxifen may provide the advantage of bioavailability and stability, suitable for use as an active ingredient in a pharmaceutical composition. Variations in the crystal structure of a pharmaceutical drug substance or active ingredient may affect the dissolution rate (which may affect bioavailability, etc.), manufacturability (e.g., ease of handling, ability to consistently prepare doses of known strength) and stability (e.g., thermal stability, shelf life, etc.) of a pharmaceutical drug product or active ingredient. Such variations may affect the preparation or formulation of pharmaceutical compositions in different dosage or delivery forms, such as solid oral dosage forms including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline forms of endoxifen may provide advantages such as: improving the manufacturing process of an active agent or the stability or storability of a drug product form of the compound or an active ingredient, and/or having suitable bioavailability and/or stability as an active agent.

The use of certain solvents and fractional crystallization methods has been found to produce different polymorphic forms of endoxifen, including any one or more of polymorphic Forms I, II and II, which may exhibit one or more favorable characteristics described above. The processes for the preparation of the polymorphs described herein, and characterization of these polymorphs are described in greater detail below.

Formula III, Form I

Figure 9:
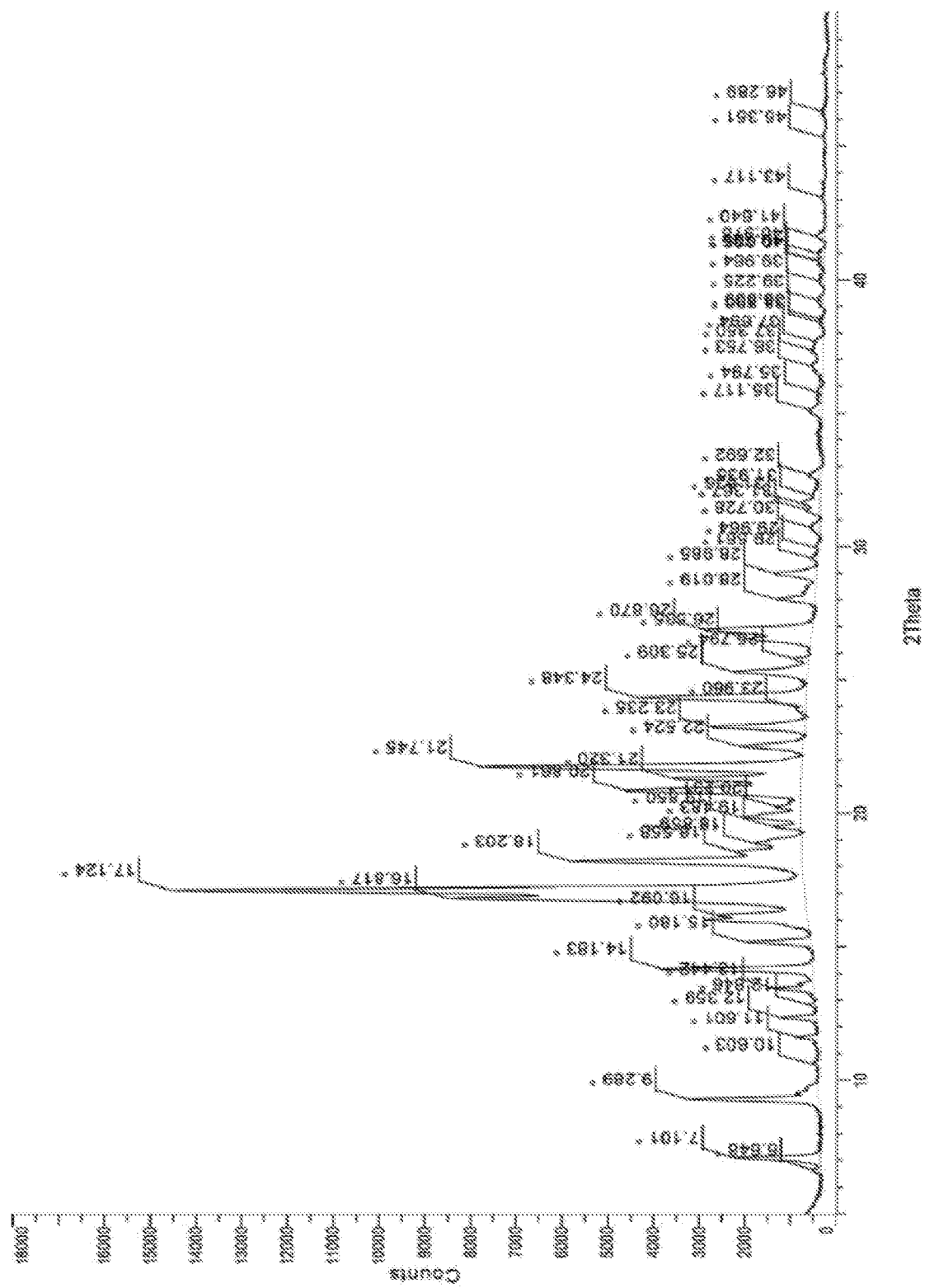
FIG. 9 is an XRPD pattern obtained from a sample of Form I of the compound of Formula (III).
Figure 10:
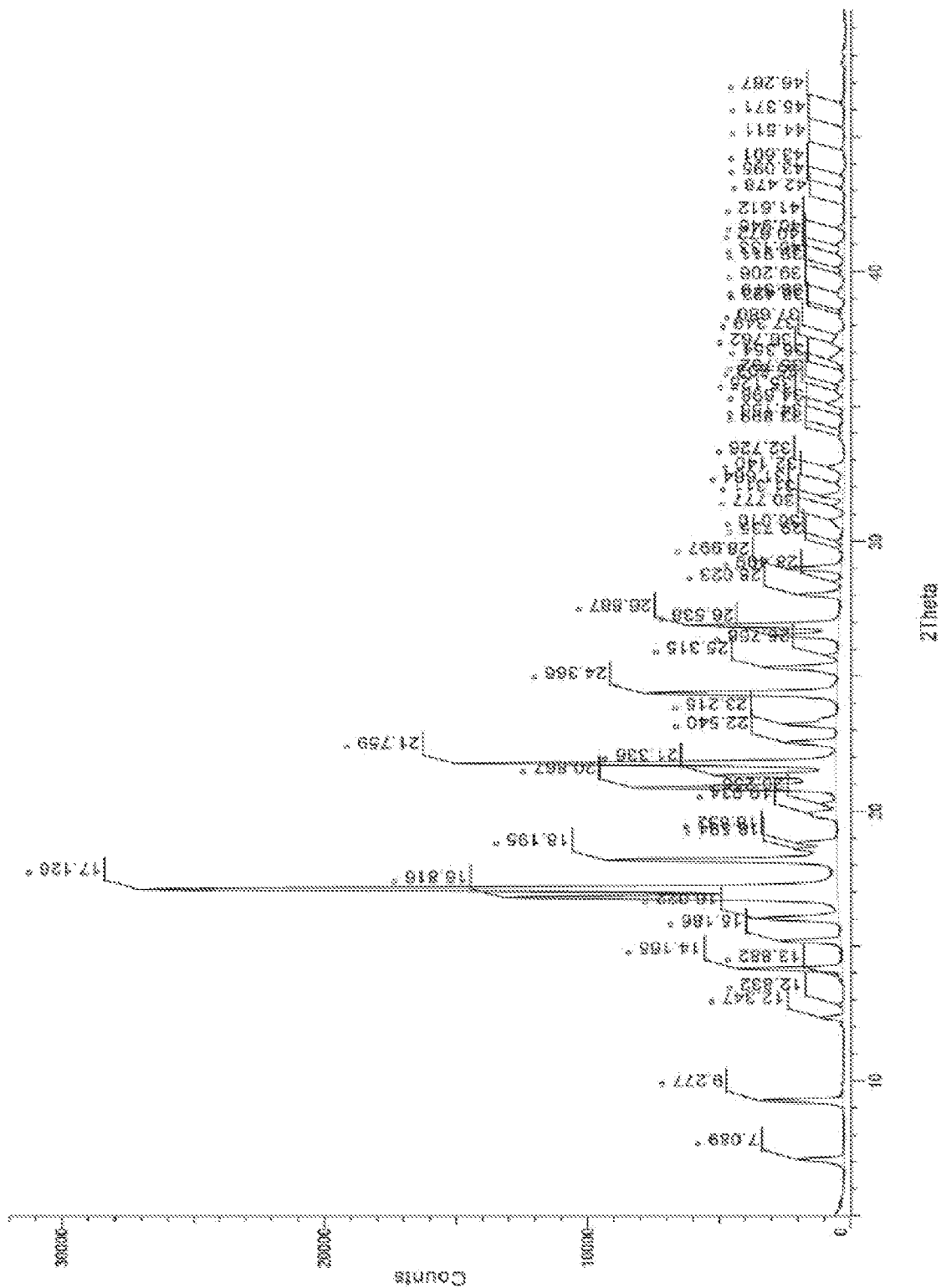
FIG. 10 is an XRPD pattern obtained from a sample of Form I of the compound of Formula (III).

In certain aspects, the present disclosure provides polymorphic Form I of a compound of Formula (III), wherein at least 90% by weight of the compound of Formula (III) in the composition is the (Z)-isomer (i.e., (Z)-endoxifen). In some embodiments, polymorphic Form I exhibits an x-ray powder diffraction (XRPD) pattern substantially as shown in FIG. 9 or FIG. 10. In some embodiments, polymorphic Form I has an XRPD pattern comprising at least two, at least three, at least four, at least five, or at least six of the major peaks as the XRPD pattern substantially as shown in FIG. 9 or FIG. 10.

The term "substantially as shown in" when referring, for example, to an XRPD pattern, includes a pattern that is not necessarily identical to those depicted herein, but that falls within the limits of experimental error or deviations when considered by one of ordinary skill in the art. The relative intensities of XRPD peaks can vary, depending upon the particle size, the sample preparation technique, the sample mounting procedure and the particular instrument employed. Moreover, instrument variation and other factors can affect the two theta (2θ) values. Accordingly, when a specified two theta angle is provided, it is to be understood that the specified two theta angle can vary by the specified value±0.5°, such as ±0.4°, ±0.3°, ±0.2°, or ±0.1°. As used herein, "major peak" refers to an XRPD peak with a relative intensity greater than 30%, such as greater than 35%. Relative intensity is calculated as a ratio of the peak intensity of the peak of interest versus the peak intensity of the largest peak in the XRPD pattern.

In certain embodiments, polymorphic Form I is characterized by an x-ray powder diffraction pattern comprising major peaks at 16.8±0.3°, 17.1±0.3° and 21.8±0.3° two theta. In some embodiments, polymorphic Form I is characterized by an x-ray powder diffraction pattern comprising peaks at 16.0±0.3°, 18.8±0.3° and 26.5±0.3° two theta. In some embodiments, polymorphic Form I is characterized by an x-ray powder diffraction pattern comprising major peaks at 16.8±0.3°, 17.1±0.3° and 21.8±0.3° two theta, and at least one peak selected from 16.0±0.3°, 18.8±0.3° and 26.5±0.3° two theta. In some embodiments, polymorphic Form I is characterized by an x-ray powder diffraction pattern comprising peaks at 12.3±0.3°, 28.0±0.3° and 29.0±0.3° two theta. In some embodiments, polymorphic Form I is characterized by an x-ray powder diffraction pattern comprising major peaks at 16.8±0.3°, 17.1±0.3° and 21.8±0.3° two theta, and at least one peak selected from 12.3±0.3°, 28.0±0.3° and 29.0±0.3° two theta. In some embodiments, polymorphic Form I is characterized by an x-ray powder diffraction pattern comprising major peaks at 16.8±0.3°, 17.1±0.3° and 21.8±0.3° two theta, and at least one peak selected from 12.3±0.3°, 16.0±0.3°, 18.8±0.3°, 26.5±0.3°, 28.0±0.3° and 29.0±0.3° two theta. In some embodiments, polymorphic Form I is characterized by an x-ray powder diffraction pattern comprising major peaks at 16.8±0.3°, 17.1±0.3° and 21.8±0.3° two theta, and peaks at 12.3±0.3°, 16.0±0.3°, 18.8±0.3°, 26.5±0.3°, 28.0±0.3° and 29.0±0.3° two theta.

In certain embodiments, the present disclosure provides a composition comprising polymorphic Form I. Greater than 90%, 95% or 99% by weight of the compound of Formula (III) in the composition may be polymorphic Form I. In some embodiments, the composition comprises 0.01 mg to 200 mg of polymorphic Form I. In some embodiments, the composition comprises about 1 mg, 2 mg, 4 mg, 6 mg, 10 mg or 20 mg of polymorphic Form I.

Formula III, Form II

Figure 11:
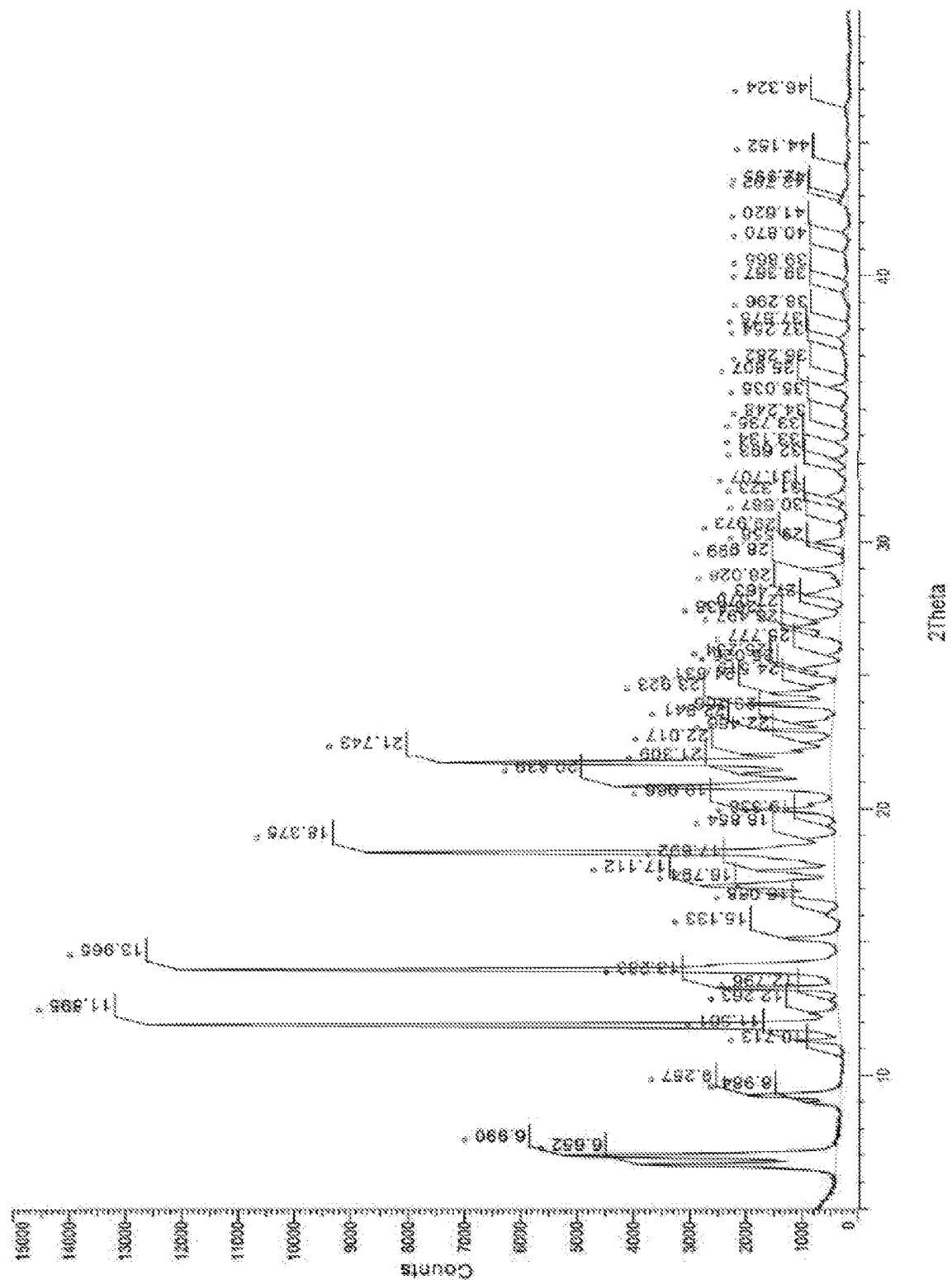
FIG. 11 is an XRPD pattern obtained from a sample of Form II of the compound of Formula (III).
Figure 12:
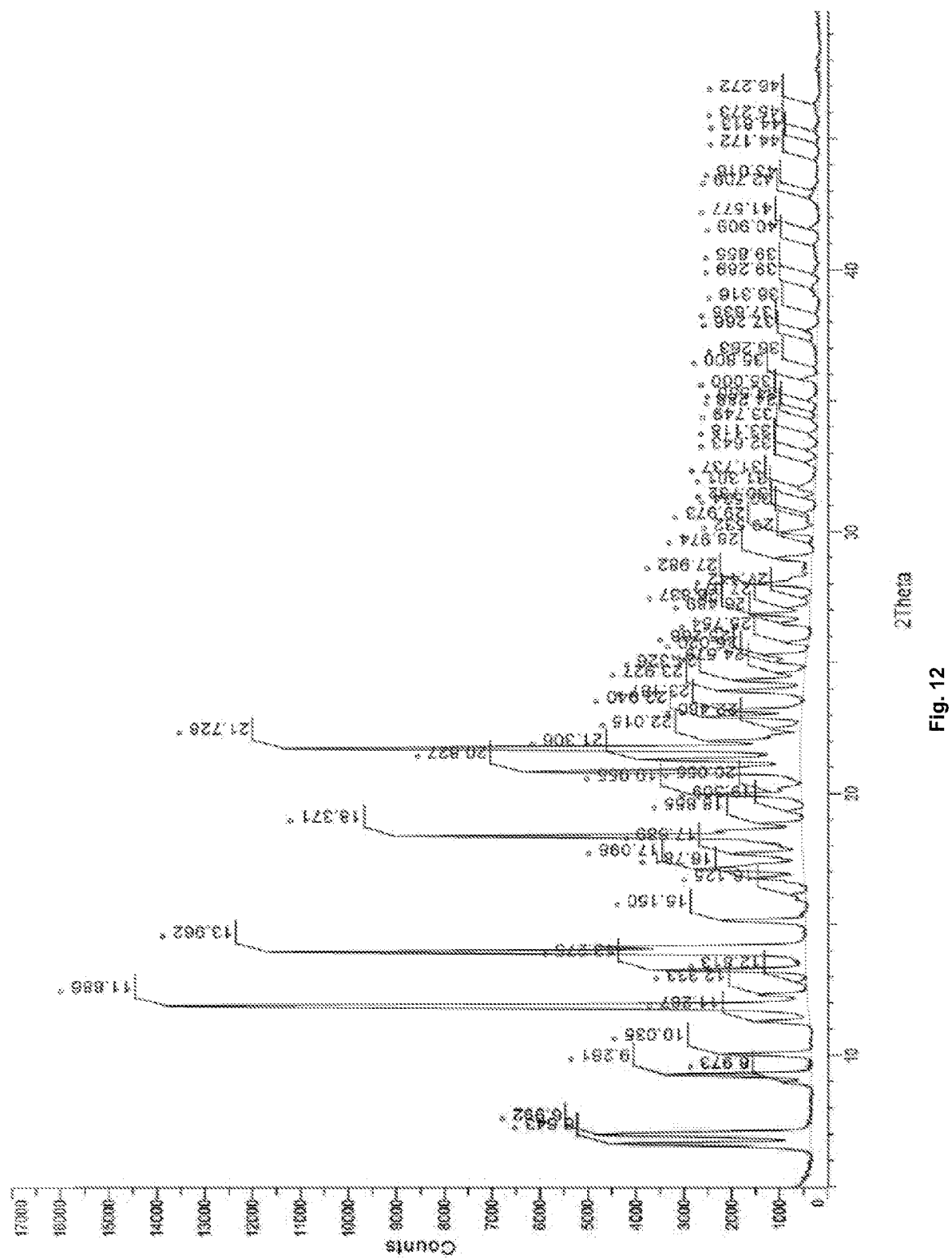
FIG. 12 is an XRPD pattern obtained from a sample of Form II of the compound of Formula (III).

In certain aspects, the present disclosure provides polymorphic Form II of a compound of Formula (III), wherein the composition comprises the (E)-isomer and the (Z)-isomer of the compound of Formula (III) (i.e., (E)-endoxifen and (Z)-endoxifen) in an E/Z ratio between 0.9 and 1.3, such as about 1.1. In some embodiments, polymorphic Form II exhibits an x-ray powder diffraction (XRPD) pattern substantially as shown in FIG. 11 or FIG. 12. In some embodiments, polymorphic Form II has an XRPD pattern comprising at least two, at least three, at least four, at least five, or at least six of the major peaks as the XRPD pattern substantially as shown in FIG. 11 or FIG. 12.

In certain embodiments, polymorphic Form II is characterized by an x-ray powder diffraction pattern comprising major peaks at 7.0±0.3°, 11.9±0.3°, 14.0±0.3° and 18.4±0.3° two theta. In some embodiments, polymorphic Form II is characterized by an x-ray powder diffraction pattern comprising a peak at 22.0±0.3° two theta. In some embodiments, polymorphic Form II is characterized by an x-ray powder diffraction pattern comprising major peaks at 7.0±0.3°, 11.9±0.3°, 14.0±0.3° and 18.4±0.3° two theta and a peak at 22.0±0.3° two theta. In some embodiments, polymorphic Form II is characterized by an x-ray powder diffraction pattern comprising at least one peak selected from 6.6±0.3°, 13.3±0.3° and 20.0±0.3° two theta. In some embodiments, polymorphic Form II is characterized by an x-ray powder diffraction pattern comprising major peaks at 7.0±0.3°, 11.9±0.3°, 14.0±0.3° and 18.4±0.3° two theta, and at least one peak selected from 6.6±0.3°, 13.3±0.3° and 20.0±0.3° two theta. In some embodiments, polymorphic Form II is characterized by an x-ray powder diffraction pattern comprising major peaks at 7.0±0.3°, 11.9±0.3°, 14.0±0.3° and 18.4±0.3° two theta, and at least one peak selected from 6.6±0.3°, 13.3±0.3°, 20.0±0.3° and 22.0±0.3° two theta. In some embodiments, polymorphic Form II is characterized by an x-ray powder diffraction pattern comprising major peaks at 7.0±0.3°, 11.9±0.3°, 14.0±0.3° and 18.4±0.3° two theta, and peaks at 6.6±0.3°, 13.3±0.3°, 20.0±0.3° and 22.0±0.3° two theta.

In certain embodiments, the present disclosure provides a composition comprising polymorphic Form II. Greater than 90%, 95% or 99% by weight of the compound of Formula (III) in the composition may be polymorphic Form II. In some embodiments, the composition comprises 0.01 mg to 200 mg of polymorphic Form II. In some embodiments, the composition comprises about 1 mg, 2 mg, 4 mg, 6 mg, 10 mg or 20 mg of polymorphic Form II.

Formula III, Form III

Figure 13:
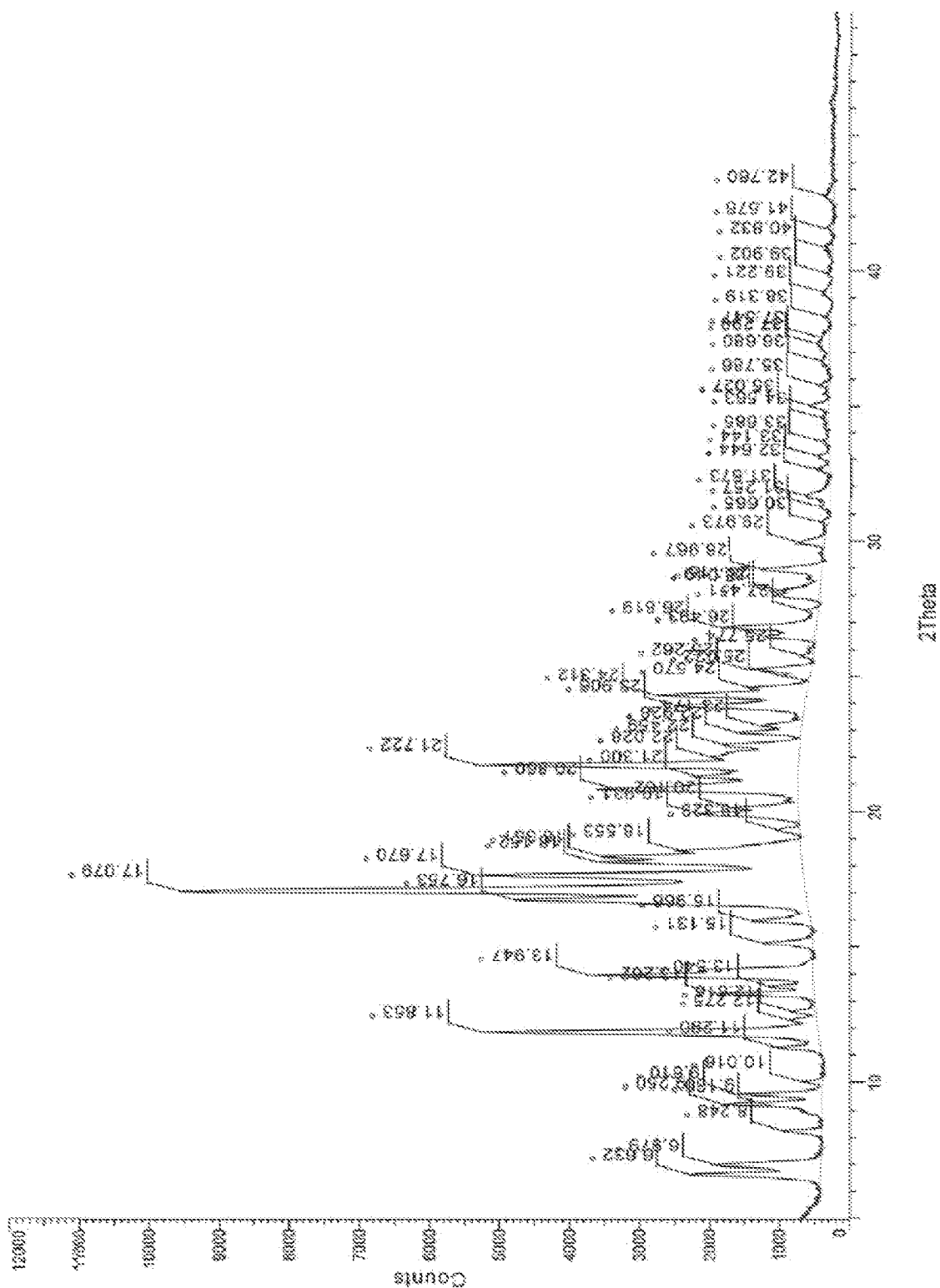
FIG. 13 is an XRPD pattern obtained from a sample of Form III of the compound of Formula (III).

In certain aspects, the present disclosure provides polymorphic Form III of a compound of Formula (III), wherein the composition comprises the (E)-isomer and the (Z)-isomer of the compound of Formula (III) (i.e., (E)-endoxifen and (Z)-endoxifen) in an E/Z ratio between 0.9 and 1.3, such as about 1.1. In some embodiments, polymorphic Form III exhibits an x-ray powder diffraction (XRPD) pattern substantially as shown in FIG. 13. In some embodiments, polymorphic Form III has an XRPD pattern comprising at least two, at least three, at least four, at least five, or at least six of the major peaks as the XRPD pattern substantially as shown in FIG. 13.

In certain embodiments, polymorphic Form III is characterized by an x-ray powder diffraction pattern comprising major peaks at $11.9\pm0.3°$, $13.9\pm0.3°$, $17.1\pm0.3°$ and $17.7\pm0.3°$ two theta. In some embodiments, polymorphic Form III is characterized by an x-ray powder diffraction pattern comprising a peak at $25.3\pm0.3°$ two theta. In some embodiments, polymorphic Form III is characterized by an x-ray powder diffraction pattern comprising major peaks at $11.9\pm0.3°$, $13.9\pm0.3°$, $17.1\pm0.3°$ and $17.7\pm0.3°$ two theta and a peak at $25.3\pm0.3°$ two theta. In some embodiments, polymorphic Form III is characterized by an x-ray powder diffraction pattern comprising at least one peak selected from $18.2\pm0.3°$, $22.5\pm0.3°$ and $26.8\pm0.3°$ two theta. In some embodiments, polymorphic Form III is characterized by an x-ray powder diffraction pattern comprising major peaks at $11.9\pm0.3°$, $13.9\pm0.3°$, $17.1\pm0.3°$ and $17.7\pm0.3°$ two theta, and at least one peak selected from $18.2\pm0.3°$, $22.5\pm0.3°$ and $26.8\pm0.3°$ two theta. In some embodiments, polymorphic Form III is characterized by an x-ray powder diffraction pattern comprising major peaks at $11.9\pm0.3°$, $13.9\pm0.3°$, $17.1\pm0.3°$ and $17.7\pm0.3°$ two theta, and at least one peak selected from $18.2\pm0.3°$, $22.5\pm0.3°$, $25.3\pm0.3°$ and $26.8\pm0.3°$ two theta. In some embodiments, polymorphic Form III is characterized by an x-ray powder diffraction pattern comprising major peaks at $11.9\pm0.3°$, $13.9\pm0.3°$, $17.1\pm0.3°$ and $17.7\pm0.3°$ two theta, and peaks at $18.2\pm0.3°$, $22.5\pm0.3°$, $25.3\pm0.3°$ and $26.8\pm0.3°$ two theta.

In certain embodiments, the present disclosure provides a composition comprising polymorphic Form III. Greater than 90%, 95% or 99% by weight of the compound of Formula (III) in the composition may be polymorphic Form III. In some embodiments, the composition comprises 0.01 mg to 200 mg of polymorphic Form III. In some embodiments, the composition comprises about 1 mg, 2 mg, 4 mg, 6 mg, 10 mg or 20 mg of polymorphic Form III.

Endoxifen Free Base Compositions

In one aspect, the present disclosure provides stable (Z)-endoxifen free base or salts thereof, and compositions comprising (Z)-endoxifen free base or salts thereof. In some embodiments, the pharmaceutical composition comprises endoxifen predominantly as (Z)-endoxifen free base.

In certain embodiments, compositions may comprise endoxifen as at least 0.1%, at least 0.2%, at least 0.3%, at least 0.4%, at least 0.5%, at least 1%, at least 5%, at least 10%, at least 20%, at least 25%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.99%, or 100% of (Z)-endoxifen free base wt/wt of total endoxifen in the composition. In at least one composition, the composition comprises ≥90% of (Z)-endoxifen free base wt/wt of the total endoxifen in the composition. In another embodiment, the composition comprises ≥95% of (Z)-endoxifen free base wt/wt of the total endoxifen in the composition. In yet another embodiment, the compositions comprise ≥96%, ≥97%, ≥98%, ≥99%, or ≥99.5% of (Z)-endoxifen free base wt/wt of the total endoxifen in the composition.

In other embodiments, compositions comprising endoxifen comprise 0.01% to 20%, 0.05% to 15%, or 0.1% to 10% of (Z)-endoxifen wt/wt or w/v of the composition. In at least one embodiment, the compositions comprising endoxifen comprise 0.01% to 20% of (Z)-endoxifen wt/wt or w/v of the composition. In various other embodiments, the compositions comprising endoxifen comprise 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 10%, or 20% of (Z)-endoxifen wt/wt of the composition.

In an aspect, the compositions comprising (Z)-endoxifen further comprise (E)-endoxifen. In some embodiments, the endoxifen in the composition has a ratio of (E)-endoxifen to (Z)-endoxifen (E/Z-ratio) of 1:99; 5:95; 10:90, 15:85; 20:80, 25:75; 30:70; 40:70, 45:55; 50:50; 55:45; 60:40; 65:45; and 70:30. In other embodiments, compositions comprise endoxifen having E/Z-ratio ranging from 10:90 to 70:30. In still other embodiments, compositions comprise endoxifen having E/Z-ratio ranging from 45:55 to 55:45.

Unless specifically referred to by the prefix (Z), (E) or (E/Z), endoxifen used generally without a prefix is used herein to include to any or all endoxifen isoforms.

Endoxifen Salt Compositions

In some embodiments, the present disclosure provides compositions comprising salts of endoxifen. In some embodiments, the present disclosure provides compositions comprising pharmaceutically acceptable salts of endoxifen. Provided herein in certain embodiments are compositions comprising 1%, 5%, 10%, 20%, 25%, 30%, 40%, 50%, 60%, 70%, 80%, 90%, 95%, 96%, 97%, 98%, 99%, 99.5%, 99.99% or 100% of endoxifen salt.

In some embodiments, the salt is selected from the group consisting of arecoline, besylate, bicarbonate, bitartarate, butylbromide, citrate, camysylate, gluconate, glutamate, glycollylarsanilate, hexylresorcinate, hydrabamine, hydrobromide, hydrochloride, hydroxynapthanoate, isethionate, malate, mandelate, mesylate, methylbromide, methylbromide, methylnitrate, methylsulfate, mucate, napsylate, nitrate, pamaoate (Embonate), pantothenate, phosphate/diphosphate, polygalacuronate, salicylate, stearate, sulfate, tannate, Teoclate, triethiodide, benzathine, clemizole, chloroprocaine, choline, diethylamine, diethanolamine, ethylenediamine, meglumine, piperazine, procaine, aluminum, barium, bismuth, lithium, magnesium, potassium, and zinc. In some embodiments, the salt is endoxifen gluconate. Endoxifen gluconate can be selected from the group consisting of (Z)-endoxifen D-gluconate, (E)-endoxifen D-gluconate, (Z)-endoxifen L-gluconate, (E)-endoxifen L-gluconate or a combination thereof.

In some embodiments, a composition comprising endoxifen gluconate is comprised of 10% to 100% of (Z)-endoxifen D-gluconate on a wt/wt basis of total endoxifen gluconate in the composition. In some embodiments, a composition comprising endoxifen gluconate is comprised of 10% to 100% of (Z)-endoxifen L-gluconate on a wt/wt basis of total endoxifen in the composition.

In other embodiments, a composition comprising endoxifen gluconate is comprised of 10%, 20%, 30%, 40%, 50%, 60%, 65%, 70%, 75%, 80%, 85%, 90%, 91%, 92%, 93%, 94%, 95%, 96%, 97%, 98%, 99%, 99.5%, 99.75%, 99.99%, or 100% of (Z)-endoxifen D-gluconate or (Z)-endoxifen L-gluconate with respect to total endoxifen gluconate. In some embodiments, the compositions comprise at least 80%, at least 85%, at least 90%, at least 91%, at least 92%, at least 93%, at least 94%, at least 95%, at least 96%, at least 97%, at least 98%, at least 99%, at least 99.5%, or at least 99.99% of (Z)-endoxifen D-gluconate, (Z)-endoxifen L-gluconate or a combination thereof.

Provided herein in some embodiments are compositions comprising (Z)-endoxifen D-gluconate and (E)-endoxifen D-gluconate. (Z)-endoxifen D-gluconate and (E)-endoxifen D-gluconate may be present in the compositions at ratios ranging from 10:90 to 99:1 wt/wt or v/v respectively. In some embodiments, the ratio of (Z)-endoxifen D-gluconate to (E)-endoxifen D-gluconate is (wt/wt or v/v) 10:90 to 99:1 (e.g., 45:55, 50:50, 60:40, 70:30, 80: 20, 90:10; 91:9; 92:8; 93:7; 94:8; 95:5, 96:4, 97:3, 98:2, 99:1, 99.5:0.5, or 99.99: 0.01) respectively. In certain embodiments, the ratio of (Z)-endoxifen D-gluconate to (E)-endoxifen D-gluconate (wt/wt or v/v) is 90:10; 91:9; 92:8; 93:7; 94:8; 95:5, 96:4, 97:3, 98:2, 99:1, 99.5:0.5, or 99.99:0.01. One of skill in the art will recognize that other combinations of endoxifen gluconate isomers are encompassed in the present disclosure.

In some embodiments, a composition comprising endoxifen gluconate comprises 0.01%, 0.05%, 0.01%, 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19% or 20% endoxifen gluconate (wt/wt) or (w/v) of the composition. In some embodiments, a composition comprising endoxifen gluconate comprises 0.01%, 0.05%, 0.01%, 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19% or 20% (Z)-endoxifen gluconate (wt/wt) or (w/v) of the composition.

The compounds and compositions of the present disclosure can be administered to a subject in need thereof by any route known in the art, including without limitation, oral, parenteral, topical, and intraductal delivery. Accordingly, compositions disclosed herein are formulated to be compatible with the intended route of administration.

In some embodiments, the compositions comprising endoxifen further comprise an excipient. Such an excipient can be compatible with the intended route of administration.

Endoxifen Polymorph Compositions

In one aspect, the present disclosure provides compositions comprising one or more polymorphic forms, such as Form I, Form II, or Form II described herein, of endoxifen. In some embodiments, the pharmaceutical composition comprises endoxifen predominantly as polymorph Form I. In some embodiments, the pharmaceutical composition comprises endoxifen predominantly as polymorph Form II. In some embodiments, the pharmaceutical composition comprises endoxifen predominantly as polymorph Form III.

In certain embodiments, a composition comprises endoxifen as at least 0.1%, at least 0.2%, at least 0.3%, at least 0.4%, at least 0.5%, at least 1%, at least 5%, at least 10%, at least 20%, at least 25%, at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, at least 99.5%, at least 99.99%, or 100% of a single polymorphic Form of endoxifen, such as Form I, Form II, or Form III, wt/wt of total endoxifen in the composition. In at least one composition, the composition comprises ≥90% of a single polymorphic Form of endoxifen, such as Form I, Form II, or Form III, wt/wt of the total endoxifen in the composition. In another embodiment, the composition comprises ≥95% of a single polymorphic Form of endoxifen, such as Form I, Form II, or Form III, wt/wt of the total endoxifen in the composition. In yet another embodiment, the composition comprises ≥96%, ≥97%, ≥98%, ≥99%, or ≥99.5% of a single polymorphic Form of endoxifen, such as Form I, Form II, or Form III, wt/wt of the total endoxifen in the composition. When a particular percentage by weight of endoxifen is a single polymorphic form, the remainder of endoxifen in the composition is some combination of amorphous endoxifen and/or one or more polymorphic forms of endoxifen excluding the single polymorphic form. When the polymorphic endoxifen is defined as one particular form of endoxifen, the remainder is made up of amorphous endoxifen and/or one or more polymorphic forms other than the particular form specified. Examples of single polymorphic forms include Forms I, II and III of endoxifen, as well as descriptions of a single polymorphic form characterized by one or more properties as described herein.

In other embodiments, a composition comprising endoxifen comprises 0.01% to 20%, 0.05% to 15%, or 0.1% to 10% of a single polymorphic Form of endoxifen, such as Form I, Form II, or Form III, wt/wt or w/v of the composition. In at least one embodiment, the composition comprising endoxifen comprises 0.01% to 20% of a single polymorphic Form of endoxifen, such as Form I, Form II, or Form III, wt/wt or w/v of the composition. In various other embodiments, the composition comprising endoxifen comprises 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 10%, or 20% of a single polymorphic Form of endoxifen, such as Form I, Form II, or Form III, wt/wt of the composition. In an aspect, a composition comprising a single polymorphic Form of endoxifen, such as Form I, Form II, or Form III, further comprises a second polymorphic Form of endoxifen.

Oral Formulations

In some embodiments, a pharmaceutical composition of the present disclosure is formulated for oral delivery. Compositions intended for oral use may be prepared in solid or fluid unit dosage forms. In at least some embodiments, the compositions are formulated for oral delivery as tablets, caplets, capsules, pills, powders, troches, elixirs, suspensions, syrups, wafers, chewing gums, dragees, lozenges, and the like.

In some embodiments, the oral dosage forms are solid oral dosage forms such as tablets, caplets, and capsules. In some embodiments, the capsule is a hard capsule or a soft capsule. In other embodiments, the capsule is a gelatin capsule, gelatin-free capsule, a "cap-in-cap" capsule, alginate capsule, hydroxypropylmethyl cellulose (HPMC) capsule, a polyvinyl alcohol (PVA) capsule, a hypromellose capsule, or a starch capsule.

Excipients

In some embodiments, an oral composition comprising (Z)-endoxifen or a salt thereof further comprises one or more excipients. In some embodiments, an oral composition comprising endoxifen or a polymorph thereof further comprises one or more excipients. Accordingly, compositions designed for oral administration can be made with an inert or active excipient or with an edible carrier as disclosed herein.

In various embodiments, the composition provided herein comprises from about 1% to about 99.99%, about 5% to about 95%, about 5% to about 90%, about 10% to about 80%, about 15% to about 70%, about 20% to about 60%, from about 30% to about 95%, from about 50% to about 90%, from about 60% to about 90%, from about 60% to about 80%, or from about 70% to about 80% by weight of one or more excipients. In certain embodiments, the composition provided herein comprises about 99.99%, about 95%, about 90%, about 85%, about 80%, about 75%, about 70%, about 65%, about 60%, about 55%, or about 50% by weight of one or more excipients. In certain embodiments, the composition provided herein comprises about 99.99%, about 99%, about 98%, about 97%, about 96%, about 95%, about 94%, about 93%, about 92%, about 91%, about 90%, about 89%, about 88%, about 87%, about 86%, or about 85% by weight of one or more excipients. In certain embodiments, the composition provided herein comprises about 85%, about 84%, about 83%, about 82%, about 80%, about 79%, about 78%, about 77%, about 76%, about 75%, about 74%, about 73%, about 72%, about 71%, about 70%, about 69%, about 68%, about 67%, about 66%, or about 65% by weight of one or more excipients. In certain embodiments, the composition provided herein comprises about 55%, about 54%, about 53%, about 52%, about 51%, about 50%, about 49%, about 48%, about 47%, about 46%, or about 45% by weight of one or more excipients. In certain embodiments, the composition provided herein comprises about 30%, about 29%, about 28%, about 27%, about 26%, about 25%, about 24%, about 23%, about 22%, about 21%, or about 20% by weight of one or more excipients.

Examples of excipients that can be used in the compositions formulated for oral administration are provided herein and can include, but are not limited to, one or more of bulking agents, binders, fillers, disintegrating agents, lubricants, glidants, control release agents, enteric coatings, film-forming agents, plasticizers, colorants, sweetners, flavoring agents and the like, or any combination thereof.

Binders suitable for use in the pharmaceutical compositions provided herein include, but are not limited to, sucrose, starches such as corn starch, potato starch, or starches such as starch paste, pregelatinized starch, and starch 1500, PEG 6000, methocel, walocel HM, Luvitec, Luvicaparolactam, Avicel, SMCC, UNIPURE, gelatin, natural and synthetic gums such as acacia, sodium alginate, alginic acid, other alginates, tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, polyvinyl pyrrolidone, hydroxypropyl methyl cellulose, (e.g., Nos. 2208, 2906, 2910), microcrystalline cellulose, and mixtures thereof. Suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. In some embodiments, the binder is a mixture of microcrystalline cellulose and sodium carboxymethyl cellulose. Suitable anhydrous or low moisture excipients or additives include AVICEL PH 103 and Starch 1500 LM.

Examples of fillers suitable for use in the pharmaceutical compositions provided herein include, but are not limited to, talc, calcium carbonate (e.g., granules or powder), sugars such as dextrose, sucrose, lactose, a salt such as calcium carbonate, calcium phosphate, sodium carbonate, sodium phosphate, starches, microcrystalline cellulose, powdered cellulose, cellulosic bases such as methyl cellulose, carboxymethyl cellulose dextrates, kaolin, mannitol, silicic acid, sorbitol, starch, pregelatinized starch, and mixtures thereof.

One or more binder or filler in compositions is typically present in from about 10% to about 99% (wt/wt) of the composition or the dosage form. In some embodiments, binders and/or fillers in a composition comprise about 15% to 99%, about 20% to 60%, about 25% to 55%, about 30% to 50%, about 35% to 60%, about 50% to 99% (wt/wt) of the composition.

Disintegrants can be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. In some embodiments, the disintegrant is deep in the oral solid dosage form to delay disintegration. The amount of disintegrant used varies based upon the type of formulation, and is readily discernible to those of ordinary skill in the art.

Typical compositions comprise from 0.5% to 15% (wt/wt) of disintegrant. In some embodiments, compositions comprise from 1% to 5% (wt/wt) of disintegrant in the composition. In another embodiment, the disintegrant is 1% to 25%, 2% to 20%, 5% to 15%, 8% to 12%, or about 10% (wt/wt) of the composition.

Disintegrants that can be used in the pharmaceutical compositions provided herein include, but are not limited to, agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in the pharmaceutical compositions provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, magnesium stearate or potassium stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB 0 SIL (a pyrogenic silicon dioxide product sold by Cabot Co. of Boston, Mass.), Q7-9120 (Dow Corning), and mixtures thereof. If used at all, lubricants are typically used in an amount of less than 1% (wt/wt) of the compositions or dosage forms into which they are incorporated. In yet another embodiment, the lubricant is 0.1% to 3%, such as 0.5% to 1% (wt/wt), of the composition.

Plasticizers may be added to control the softness or pliability of oral dosage forms such as shell of a capsule, caplet or a tablet and thus, may improve the mechanical properties of the pH-sensitive materials of the coatings on the oral dosage forms. Suitable plasticizers, include, without limitation, petroleum oils (for e.g., a paraffinic process oil, a naphthenic process oil, and an aromatic process oil), squalene, squalane, plant oils, (e.g., olive oil, camelia oil, castor oil, tall oil, and a peanut oil), silicon oils, dibasic acid esters, (e.g., dibutyl phthalate, and dioctyl phthalate), liquid rubbers (e.g., polybutene and a liquid isoprene rubber), liquid fatty acid esters (e.g., isopropyl myristate ISM), hexyl laurate, diethyl sebacate, and diisopropyl sebacate, triethyl citrate, triacetin, diethylene glycol, polyethylene glycols, polypropylene glycol, phthalates, sorbitol, glycol salicylate, crotaminton, and glycerin or mixtures thereof. The amount of plasticizer may vary depending upon the chemical composition of the pharmaceutical preparation. In one embodiment, the at least one plasticizer is sorbitol, dimethyl isosorbide, or a glycerol. In another embodiment, the plasticizer is 1% to 10%, such as 3% to 5% (wt/wt), of the composition.

Examples of glidants include, but are not limited to, colloidal silicone dioxide, cellulose, calcium phosphate, di or tri-basic and the like.

As an example of sweetners or sweetening agents include sucrose, saccharin, dextrose, maltose, sugar substitutes, aspartame, xylitol, mannitol, cyclamate, sucralose, maltitol, sorbitol, acesulfame K and the like.

Examples of flavoring agents include peppermint, methyl salicylate, peppermint, spearmint, methyl salicylate, raspberry, red berry, strawberry, pineapple, orange, cherry and the like.

Compositions formulated for oral delivery as disclosed herein, for example, tablets, caplets, and capsules, may be coated with one or more enteric coating agent, control release agent or film forming agent to control or delay disintegration and absorption of the compositions comprising endoxifen or salts thereof in the gastrointestinal tract and thereby provide a sustained action over a longer period of time. Accordingly, in some embodiments, the tablet can be an enteric tablet, the caplet can be an enteric caplet, or the capsule can be an enteric capsule. The enteric tablets, enteric caplets, or enteric capsules of the present disclosure may be prepared by techniques known in the art.

Pharmaceutical preparations disclosed herein may comprise a control release agent. Examples of control release agent suitable for use include, without limitation, pH-dependent polymers, acid-insoluble polymers, methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, shellac, cellulose acetate trimellitate, sodium alginate, zein, waxes, including synthetic waxes, microcrystalline waxes, paraffin wax, carnauba wax, and beeswax; polyethoxylated castor oil derivatives, hydrogenated oils, glyceryl mono-, di-tribenates, glyceryl monostearate, glyceryl distearate, long chain alcohols, such as stearyl alcohol, cetyl alcohol, and polyethylene glycol; and mixtures thereof. In some embodiments, a time delay material such as glyceryl monostearate or glyceryl distearate may be used. In other embodiments, the controlled release reagent is a digestible waxy substance such as hard paraffin wax.

In some embodiments, compositions may comprise one or more of pH-dependent polymers such as acid insoluble polymers. The pH-dependent polymers become increasingly permeable above pH 5.0 but are impermeable at pH below 5.0 whereas acid insoluble polymers become soluble in neutral to weakly alkaline conditions. Such control release polymers target upper small intestines and colon. Non-limiting examples of acid-insoluble polymers include cellulose acetate phthalate, cellulose acetate butyrate, hydroxypropyl methyl cellulose phthalate, algenic acid salts such as sodium or potassium alginate, shellac, pectin, acrylic acid-methylacrylic acid copolymers (commercially available under the tradename EUDRAGIT® L and EUDRAGIT® S from Rohm America Inc., Piscataway, N.J. as a powder or a 30% aqueous dispersion; or under the tradename EAST-ACRYL®, from Eastman Chemical Co., Kingsport, Tenn., as a 30% dispersion). Additional examples include EUDRAGIT® L100-55, EUDRAGIT® L30D-55, EUDRAGIT® L100, EUDRAGIT® L100 12,5, EUDRAGIT® S100, EUDRAGIT® S12,5, EUDRAGIT® FS 30D, EUDRAGIT® E100, EUDRAGIT® E 12,5, and EUDRAGIT® PO. In at least one embodiment, the composition comprises EUDRAGIT® L100-55. EUDRAGIT® RS and RL and EUDRAGIT®NE and NM are also useful polymers for the purpose of this disclosure. In some embodiments, the composition comprises EUDRAGIT® L3OD 55. In another embodiment, the preparation comprises EUDRAGIT® FS 30D. One of skill in the art will recognize that at least some acid insoluble polymers listed herein will also be biodegradable.

For time delay or delayed-release pharmaceutical preparations of oral dosage forms, glyceryl monostearate, glyceryl distearate, and acid-insoluble polymers, for example polymethacrylate pH-sensitive polymer-based coatings can be used, (e.g., as coating material, i.e., enteric coating agents, for enteric coating of capsules, caplets, and tablets). Commercial sources for delayed-release oral dosage forms are available, for example DRCaps made of hypromellose (HPMC) from Capsugel, USA. Such delayed-release oral dosage forms forms are acid-resistant and can resist acidity as seen in stomach for at least 30 min, such as for at least 1 hour, for at least 1.5 hour, or for at least 2 hours. Such delayed release oral dosage forms can release at least 40%, at least 50%, at least 60%, at least 70%, at least 80% or at least 90% of the endoxifen or salts thereof in the intestines (small intestines, large intestine/colon etc).

In an aspect of the present disclosure, the enteric tablets, enteric caplets, and enteric capsules may be uncoated. Hard uncoated capsules with enteric capability using intrinsically enteric capsule technology (for example, EnTrinsic Drug Delivery available from Capsugel) are suitable for the purpose of the present disclosure.

In various embodiments, the enteric tablet is a hard tablet made with free-flowing powder of (Z)-endoxifen or a salt thereof. In various embodiments, the enteric capsule is a capsule made with free-flowing powder of (Z)-endoxifen or a salt thereof. In various embodiments, the enteric tablet is a hard tablet made with free-flowing powder of endoxifen or a polymorph thereof. In various embodiments, the enteric capsule is a capsule made with free-flowing powder of endoxifen or a polymorph thereof.

In some embodiments, the enteric capsule is a non-animal based capsule, such as a hypromellose capsule (for example, commercially available self-gelling Vcaps, VCaps Plus, VCaps enteric, other enteric capsules made using Xcellodose, ENCODE colonic delivery technology, and EnTrinsic™ drug delivery technology from Capsugel). Other technologies known in the art and available commercially (for example, Qualicaps, USA, Nutrascience, USA, etc.) for the formulating enteric forms of oral solid dosage forms can also be utilized. In at least one embodiment, the capsule is an API-in-capsule, meaning that the (Z)-endoxifen free base or salts thereof is filled neat into the capsule. In such API-in-capsule oral dosage forms, the active ingredient, (Z)-endoxifen or salts thereof can be free flowing powders or micronized powders. When the dosage form is a capsule, in at least one embodiment, the capsule can be a seamless capsule or a banded capsule.

Rapid absorption and bioavailability of the anti-cancer therapeutics such as endoxifen that can further reduce the cancer growth rate are highly desirable. In an aspect, the present disclosure provides that the compositions are formulated for certain pharmacokinetic (PK) properties.

In one aspect, rapid achievement of maximal and steady state plasma levels of endoxifen is a particular aspect of the present disclosure. The present disclosure provides compositions that achieve a maximal plasma level of endoxifen ranging within 2 to 30 hours, within 3 to 20 hours, within 2 to 10 hours or within 4 to 8 hours after administration of the compositions. Accordingly, in some embodiments, time to maximal (peak) plasma level of endoxifen ranges from 2 to 10 hours after administration of the composition. In some embodiments, the time to maximal plasma level of endoxifen ranges from 4 to 8 hours after administration of a composition disclosed herein.

Rapid achievement of steady-state plasma levels of endoxifen is also highly desirable, and a composition of the present disclosure may provide a plasma level of endoxifen in a subject administered the composition comprising a polymorphic form of endoxifen, (Z)-endoxifen or a salt thereof that rapidly achieves steady state. Steady state plasma levels can be achieved from day 7 to day 21. In some embodiments, the steady state plasma levels can be achieved by day 7 (FIG. 5) upon daily administration of a composition disclosed herein.

In an aspect, the present disclosure provides that circulating endoxifen released from a composition disclosed herein can be cleared faster than tamoxifen. Terminal elimination half life of tamoxifen is said to be 5-7 days (Jordan C. Steroids. 2007 November; 72(13): 829-842) and peak concentration time of tamoxifen is approximately 5 hours post-dose. Endoxifen released from a composition disclosed herein can have a terminal elimination half-life ranging from 30 to 60 hours, significantly lower than tamoxifen. In some embodiments, the mean half-life ranges from 40 to 53 hours. The mean ratio of $AUC_{24hr}$ (Day 21)/$AUC_{0-inf}$ (Day1) typically ranges from 0.7 to 1.2 for compositions comprising 1 mg to 4 mg (Z)-endoxifen, or a salt thereof. Thus, accumulation of endoxifen released from a compositions disclosed herein does not significantly vary over continued treatment.

In another aspect, a composition described herein achieves absorption of endoxifen that is therapeutically effective.

Area under Curve $AUC_{(0-24hr)}$ ("$AUC_{24hr}$") describes the total exposure of the subject to a drug from time of dosing (0 hr) over a 24 hour period. Compositions comprising (Z)-endoxifen or a salt thereof typically achieve mean ($AUC_{24hr}$) of 150 hr*ng/mL to 600 hr*ng/mL on Day 1 of initial (first) dose of a composition comprising 1 mg to 4 mg of (Z)-endoxifen. Compositions comprising (Z)-endoxifen or a salt thereof typically achieve mean $AUC_{24hr}$ of 400 hr*ng/mL to 2500 hr*ng/mL on Day 21 of initial (first) dose of compositions comprising 1 mg to 4 mg of (Z)-endoxifen.

$AUC_{0-inf}$ ("$AUC_{0-inf}$"), a time-averaged concentration of drug circulating in the body fluid analyzed (normally plasma, blood or serum), describes the total exposure of the subject to a drug. The present disclosure provides that the exposure of a subject to endoxifen ($AUC_{0-inf}$) can be dose proportional. In some embodiments, $AUC_{0-inf}$ ranges from 200 hr*ng/mL to 10000 hr*ng/mL. In other embodiments, the $AUC_{0-inf}$ ranges from 300 hr*ng/mL to 8000 hr*ng/mL. In certain embodiments, the $AUC_{0-inf}$ ranges from 400 hr*ng/mL to 6000 hr*ng/mL over the dosing range of 1 mg to 4 mg of (Z)-endoxifen (for example, see Table 17).

Dissolution of the oral dosage forms disclosed herein is tested by the dissolution tests according to the current methods of USP 711. In some embodiments, the oral dosage forms disclosed herein are protected from the acidic environment of the stomach and do not dissolve for at least 2 hours, at least 3 hours, at least 4 hours, at least 5 hours, 6 hours, at least 7 hours or at least 8 hours. In at least one embodiment, the oral dosage forms do not release endoxifen for at least 6 hours. In another embodiment, the oral dosage forms do not release endoxifen or a salt thereof for at least 2 hours.

In other embodiments, less than 10% of (Z)-endoxifen in a composition comprising endoxifen or a salt thereof disclosed herein is released in the stomach after 2 hours after administration; or wherein less than 40% of (Z)-endoxifen is released in the stomach after 4 hours of administration; or less than 50% of (Z)-endoxifen is released in the stomach after 6 hours of administration, as tested by a method of USP 711.

In another embodiment, a composition disclosed herein releases in the stomach less than 10% of (Z)-endoxifen in 2 hours after administration, less than 40% of (Z)-endoxifen in 4 hours after administration; and less than 50% of (Z)-endoxifen in 6 hours after administration, as tested by a method of USP 711.

In yet another embodiment, the composition is formulated to release in the small intestine, such that at least 10% of endoxifen is released after 4 hours after administration; or at least 30% of endoxifen is released after 6 hours after administration; or at least 40% of endoxifen is released after 7 hours after administration; or at least 50% of endoxifen is released after 8 hours after administration, as tested by a method of USP 711.

In a further embodiment, as determined by a method of USP 711, the composition is formulated to release in the colon at least 50% of endoxifen after 8 hours after administration.

In still further embodiments, the composition is formulated to release in the colon at least 20% of endoxifen after 4 hours after administration; at least 40% of endoxifen after 6 hours after administration; at least 60% of endoxifen after 7 hours after administration; or at least 80% of endoxifen after 8 hours after administration.

An oral dosage form can be of any shape suitable for oral administration, such as spherical (0.05-5 mL), oval (0.05-7 mL), ellipsoidal, pear (0.3-5 mL), cylindrical, cubic, regular and/or irregular shaped. An oral dosage form may be of any size suitable for oral administration, for example, size 0, size 2, and the like.

One of skill in the art will further recognize that compositions disclosed herein may comprise one or more of the excipients known in the art and disclosed herein in any combination appropriate for a desired formulation or preparation. Additional excipients may generally be found in Remington's The Science and Practice of Pharmacy, Meade Publishing Co., United States Pharmacopeia/National Formulary. One of skill in the art will be able to select suitable excipients necessary for the preparation of the formulations and appropriate dosage forms compatible with the route of administration based on his or her skill and knowledge in the art and the disclosures made herein. In all cases, the ultimate dosage form should be sterile and stable under the conditions of manufacture and storage.

For formulations of the solid dosage compositions disclosed herein, as the water activity ($A_w$) is less than 0.75, testing Total Aerobic Plate Count (TAC) and USP indicator organism is typically not necessary. The publication, "Microbial Bioburden on Oral Solid Dosage Form," by Jose E. Martinez, Pharmaceutical Technology, February 2002, pages 58 to 70, is hereby incorporated by reference in its entirety.

Furthermore, since formulations of the compositions disclosed herein also have water activity of less than 0.75, then detailed microbial testing is typically not necessary. TAC is an estimation of the total viable aerobic microbes present in a sample of raw material, in-process material, or finished product. Samples are analyzed in accordance with the most current USP 39 <61>, "Microbiological Examination of Nonsterile Products: Microbial Enumeration Tests."

Acceptable TAC for oral solid dosage forms (OSDFs) are established for the formulation of the inventive compositions in terms of alert and action levels, which could be 1000 cfu g/mL, and 10,000 cfu g/mL, respectively. A TAC that is 20,000 cfu g/mL may be considered unacceptable.

For other formulations, such as liquid or fluid formulations with water activity of less than 0.75, Tests for Specified Microorganisms (*S. aureus, Ps. aeruginosa, Salmonella, C. albicans, Clostridia, E. coli* and Bile Tolerant Gram negative bacteria) in compliance with USP Guidelines Chapter 62 may not need to be performed.

Methods of Use

Compounds of Formulae (I), (II), (III), and (IV), endoxifen salts disclosed herein, polymorphic forms of endoxifen disclosed herein, and compositions comprising them may be used in the manufacture of medicaments for use in the treatment of a subject in need thereof, for example, subjects having or at risk of having a hormone-dependent breast disorder, a hormone-dependent reproductive tract disorder, or both.

The compositions of the present disclosure may be used as a primary therapy, as a part of a neo-adjuvant therapy (to primary therapy), or as part of adjuvant therapy regimen, where the intention is to ameliorate or cure a subject having or at risk of having a hormone-dependent breast disorder, hormone-dependent reproductive tract disorder, or both.

In certain embodiments, the disorder is a hormone-dependent breast disorder. In other embodiments, the disorder is hormone-dependent reproductive tract disorder. In still other embodiments, the subject has both a hormone-dependent breast disorder and a hormone-dependent reproductive tract disorder. In some embodiments, the hormone dependent disorder is a benign breast disorder, hyperplasia, atypia, atypical ductal hyperplasia, atypical lobular hyperplasia, increased breast density, gynecomastia, DCIS, LCIS, breast cancer, endometrial cancer, ovarian cancer, uterine cancer, cervical cancer, vaginal cancer or vulvar cancer.

In some embodiments, the breast disorder is increased breast density. For example, the breast disorder is a class B (formerly Class II), class C (formerly class III) or class D (formerly class IV) breast density.

In some embodiments, the hormone-dependent breast disorder or hormone-dependent reproductive tract disorder is precocious puberty. In other embodiments, the hormone-dependent breast disorder or hormone-dependent reproductive tract disorder is McCune-Albright Syndrome.

In some embodiments, the breast disorder is gynecomastia. In some embodiments, gynecomastia is presented secondarily to an underlying disease. Accordingly in some embodiments, the subject also has underlying disease selected from the group consisting of prostate cancer, cirrhosis and liver disease, male hypogonadism, hyperthyroidism, renal failure and in patients undergoing hemodialysis, or type I diabetes mellitus. In certain embodiments, the subject has prostate cancer as the underlying disease, wherein the subject has or is at risk of having gynecomastia.

In certain embodiments, the breast cancer is DCIS, LCIS, ILC, IDC, MIC, inflammatory breast cancer, ER-positive (ER+) breast cancer, HER2+ breast cancer, adenoid cystic (adenocystic) carcinoma, low-grade adenosquamatous carcinoma, medullary carcinoma, mucinous (or colloid) carcinoma, papillary carcinoma, tubular carcinoma, metaplastic carcinoma, or micropapillary carcinoma. In at least one embodiment, a single breast cancer tumor may be a combination of the foregoing or be a mixture of invasive and in situ cancer.

The present disclosure contemplates the use of the compounds and compositions disclosed herein at various stages in tumor development and progression, including the treatment of advanced and/or aggressive neoplasms, i.e., overt disease in a subject that is not amenable to cure by local modalities of treatment such as surgery or radiotherapy, metastatic disease, or locally advanced disease. Accordingly in some embodiments, the breast cancer is a pre-cancer, an early stage cancer, a non-metastatic cancer, a pre-metastatic cancer, or a locally advanced cancer. In at least one embodiment, the breast disorder is metastatic cancer. In some embodiments, the subject further has prostate cancer.

Current choice for therapeutics for such disorders remains tamoxifen, despite serious adverse effects, poor patient compliance and resistance to the drug due to low plasma endoxifen levels seen subjects. Such subjects may have low endoxifen levels upon dosing with tamoxifen for any number of reasons, such as having CYP gene mutations, for example, in CYP2D6, CYP3A4, or CYP2C9, making them unable to metabolize tamoxifen to its active metabolite, endoxifen, or low or dysfunctional estrogen receptor preventing (or decreasing) sufficient tamoxifen uptake, for other reasons yet to be identified. Reported therapeutic levels of plasma tamoxifen in subjects dosed with 20 mg of oral tamoxifen is ≥30 nM ((Lyon et al. Genet Med. 2012 December; 14(12):990-1000). Notwithstanding the mechanism underlying the low plasma endoxifen in a subject, the compositions of the present disclosure are useful for any condition wherein a subject has low endoxifen or the subject has or is at a risk of having hormone-dependent breast disorder or hormone-dependent reproductive tract disorder. Therefore, the compositions of the present disclosure can be particularly important in the treatment of tamoxifen-resistant, hormone-dependent breast disorders or hormone-dependent reproductive tract disorders.

Provided herein in certain embodiments are patient populations for whom the pharmaceutical compositions are particularly useful. The compositions of the present disclosure are also particularly important in the treatment of tamoxifen-refractory subjects with hormone-dependent breast disorders or hormone-dependent reproductive tract disorders. Accordingly, in some embodiments, the compositions disclosed herein are useful for the treatment of tamoxifen refractory or tamoxifen resistant subjects having or at risk of having hormone-dependent breast disorders, hormone-dependent reproductive tract disorders, or both. In some embodiments, compositions comprising an endoxifen salt, such as endoxifen gluconate, administered to such subject at the doses disclosed herein, will be advantageous.

Further, Donneyong et al. have shown that drug interactions between tamoxifen and selective serotonin reuptake inhibitors (SSRI) drugs like Prozac and Paxil (paroxetine) exist and are detrimental to breast cancer subjects (Donneyong et al. BMJ 2016; 354:i5014). The SSRI drugs reduce or stop liver metabolism of tamoxifen to endoxifen in subjects on SSRI drugs. Thus, provided herein in certain embodiments are patient populations being treated or to be treated with SSRI drugs that would be benefitted by treatment with compositions of the present disclosure.

Compositions disclosed herein administered orally maintain the subject's plasma endoxifen at steady state levels greater than 30 nM, for example, at levels ranging from 30 nM to 80 nM or at levels ranging from 30 nM to 300 nM. In some embodiments, the plasma steady state endoxifen levels are maintained at >40 nM. Maintenance of such a plasma endoxifen at steady state levels greater than 30 nM is advantageous in that the likelihood of recurrence (relapse) of hormone-dependent breast disorders or hormone-dependent reproductive tract disorders, particularly breast cancer, at plasma endoxifen levels lower than 30 nM is reduced. It is particularly advantageous for subjects that are poor-metabolizers of tamoxifen (with plasma endoxifen levels lower than 16 nM), intermediate metabolizers of tamoxifen (with plasma endoxifen levels lower than 27 nM) to be dosed with a composition disclosed herein. It also advantageous for subjects being treated or to be treated with antidepressant drugs such as SSRI drugs such as citalopram (Celexa), escitalopram (Lexapro), fluoxetine (Prozac), paroxetine (Paxil, Pexeva), sertraline (Zoloft), vilazodone (Viibryd) and the like, for example, a subject having or likely to have depression.

Whether a subject is tamoxifen-refractory may be determined by dosing a subject with an initial dosage of tamoxifen and determining the subject's plasma endoxifen steady state level. Plasma endoxifen steady state levels in a subject dosed with tamoxifen serves as a biomarker for the tamoxifen-refractory subjects. The plasma endoxifen levels (acute and/or steady state) may be determined by obtaining from the subject a test sample, which may be blood sample, collected from the subject after dosing the subject with tamoxifen. Plasma or serum may be obtained from blood samples for testing the biomarker endoxifen levels. The initial dosage may comprise administering tamoxifen daily for at least 1 day, 2 days, 3 days, 15 days, 1 week, 2 weeks, 4 weeks, 1 month, 2 months, 3 months, 4 months, 5 months, or 6 months. The subject may also be administered with a first composition comprising tamoxifen daily for at least 1 day, 2 days, 3 days, 15 days, 1 week, 2 weeks, 4 weeks, 1 month, 2 months, 3 months, 4 months, 5 months, 6 months, 1 year, 2 years, 3 years, 4 years, 5 years or 10 years.

A subject's plasma endoxifen steady state level may be determined by measuring endoxifen in a test sample. The subject's plasma endoxifen steady state levels are compared to a reference plasma endoxifen level. For the purposes of the present disclosure, the reference plasma level is 30 nM. If the subject's plasma endoxifen level is determined to be lower than 30 nM, then the subject is defined as tamoxifen-refractory. Such a tamoxifen-refractory subject who has or who may be at risk of having a hormone-dependent breast disorder or hormone-dependent reproductive tract disorder is treated by administering to the subject an oral composition comprising (Z)-endoxifen or a salt thereof disclosed herein, or a polymorphic form of endoxifen disclosed herein. In some embodiments, the composition administered to such a subject comprises (Z)-endoxifen free base. In some embodiments, the composition administered to such a subject comprises a polymorphic form, such as Form I, Form II or Form III, of endoxifen. In other embodiments, the composition administered to such a subject comprises endoxifen gluconate selected from the group consisting of (Z)-endoxifen D-gluconate, (Z)-endoxifen L-gluconate, (E)-endoxifen D-gluconate, (E)-endoxifen L-gluconate, or a combination thereof. In other embodiments, the composition comprising endoxifen is endoxifen HCl or endoxifen citrate. The present disclosure also contemplates that a subject's plasma endoxifen levels are tracked or monitored periodically or as necessary. If required, a subject who has been administered an initial dosage of tamoxifen may have his or her plasma endoxifen steady state levels adjusted by administering a composition comprising endoxifen on an ongoing basis based on the test results.

In some embodiments, the subject's tamoxifen-refractory status may be determined by determining the subject's tamoxifen-metabolites profile which is compared with a reference tamoxifen-metabolite profile as seen in control or normal subjects. Subjects with low plasma endoxifen levels in subject's tamoxifen-metabolite profile as compared to the reference tamoxifen-metabolite profile are administered an oral composition comprising endoxifen or a salt thereof. Such compositions may comprise synthetically prepared endoxifen.

The plasma endoxifen may be measured by any of method known in the art. The levels of plasma endoxifen in test sample may be determined based on subject's genes, DNA, RNA, protein, tamoxifen-metabolite profile or a combination thereof. The tamoxifen-metabolites profile can include at least tamoxifen, 4-OHT, N-desmethyltamoxifen, and/or endoxifen. In some embodiments, the level of plasma endoxifen and/or tamoxifen-metabolite profile in the test sample is measured by High Performance Liquid Chromatography (HPLC), Gas Chromatography Mass Spectrometry (GC-MS), Liquid Chromatography Mass spectrometry (LC-MS), Liquid Chromatography Tandem Mass spectrometry (LC-MS/MS), immunohistochemistry (IHC), polymerase chain reaction (PCR), quantitative PCR (qPCR), and the like. In some embodiments, the tamoxifen-metabolites profile is predicted based on the subject's genetic composition. In some embodiments, the subject's CYP genotype includes, without limitation, analysis of CYP2D6, CYP3A4, CYP2C9 genes. In some embodiments, subject's estrogen receptor levels may be analyzed. In other embodiments, the determination of plasma endoxifen may be done by a third party laboratory.

Accordingly, provided herein are methods of maintaining in a subject in need thereof a plasma endoxifen a level greater than 30 nM by administering to the subject a composition comprising endoxifen or a salt thereof. In some embodiments, the subject's plasma endoxifen level is maintained at a steady state level greater than 30 nM. In some embodiments, the subject's plasma endoxifen levels are maintained at a steady state level ranging from 30 nM to 300 nM (for example, from 30 nM to 200 nM, or from 30 nm to 80 nM). In some embodiments, the subject's plasma endoxifen levels are maintained at a steady state level >40 nM.

In another aspect, the subjects may have their test samples tested for their biomarker profile that may be indicative or monitoring a hormone-dependent breast disorder, a hormone-dependent reproductive tract disorder, or both. Such biomarkers are known in the art and include, by way of non-limiting examples, biomarkers such as CYP2D6, BRCA-1, BRCA-2, ER, PR, Her2, uPA, PAI, Tf, p53, Ki67, cytokeratins, cancer tumor antigens, and other biomarkers measured by Mammaprint, OncotypeDx, PAM50, EndoxPredict, MammoStrat, and other diagnostic and predictive tests. A subject with biomarker profile indicating that the subject has or is at risk of having a hormone-dependent breast disorder, a hormone-dependent reproductive tract disorder, or both can be administered a composition disclosed herein. In one aspect, the present disclosure provides a method of treating a subject having or at risk of having a hormone-dependent breast disorder, a hormone-dependent reproductive tract disorder, or both, comprising determining a subject's tamoxifen-refractory or tamoxifen-resistant status and administering to the subject a composition described herein.

In some aspects, provided herein are methods of treating a tamoxifen-refractory or tamoxifen-resistant subject, the method comprising administration to the subject a composition comprising endoxifen, or a salt or polymorph thereof.

In some embodiments disclosed herein are methods of treating a tamoxifen-refractory subject having or at risk for having a hormone-sensitive breast disorder, a hormone-sensitive reproductive tract disorder, or both, the method comprising administration to the subject an oral composition comprising endoxifen, or a salt thereof, wherein the subject has plasma endoxifen level of less than 30 nM, less than 25 nM, less than 20 nM, less than 15 nM, less than 10 nM, less than 5 nM or less than 1 nM. In certain embodiments, the composition comprising endoxifen salt is endoxifen gluconate, endoxifen HCl, or endoxifen citrate. In other embodiments, an oral solid dosage form comprising at least 90% (Z)-endoxifen or a salt thereof is administered. In other embodiments, an oral solid dosage form comprising at least 90% of polymorph Form I, Form II, or Form III of endoxifen is administered.

Also provided herein are methods of treating a tamoxifen-refractory subject, the method comprising: (a) determining or having determined plasma endoxifen level in a test sample obtained from the subject; (b) comparing or having compared or having determined the level of plasma endoxifen in the test sample with a reference plasma endoxifen level; (c) determining or having determined a reduced level of plasma endoxifen in the test sample as compared to the reference plasma endoxifen level; and (d) administering a composition comprising endoxifen or a salt or polymorph thereof to the subject. The administration of a composition comprising endoxifen or a salt or polymorph thereof maintains the levels of plasma endoxifen in the subject at steady state levels greater than 30 nM. In some embodiments, the levels of plasma endoxifen in the subject are maintained at steady state levels ranging from 30 nM to 80 nM.

Provided herein are methods of treating a subject having or at risk of having a hormonal dependent breast disorder or a hormonal dependent reproductive tract disorder, the method comprising: (a) administering to the subject a first composition comprising tamoxifen; (b) determining or having determined the level of plasma endoxifen in a test sample obtained from the subject; (c) determining or having determined reduced level of plasma endoxifen in test sample as compared to a reference level of plasma endoxifen; and (d) administering an oral composition disclosed herein to the subject. The subject may be administered with the first composition comprising tamoxifen daily for at least 1 day, 2 days, 3 days, 15 days, 1 week, 2 weeks, 4 weeks, 1 month, 2 months, 3 months, 4 months, 5 months, 6 months, 1 year, 2 years, 3 years, 4 years, 5 years or 10 years. In some embodiments, administration of the oral composition comprising endoxifen or a salt or polymorph thereof maintains the subject's plasma endoxifen at levels greater than 30 nM. In other embodiments, administration of the oral composition comprising endoxifen or a salt or polymorph thereof maintains the subject's plasma endoxifen at levels ranging from 30 nM to 300 nM (e.g., from 30 nM to 200 nM, or from 30 nM to 80 nM). In some embodiments, the subject is administered an oral composition comprising (Z)-endoxifen D-gluconate, (Z)-endoxifen L-gluconate, (E)-endoxifen D-gluconate, (E)-endoxifen L-gluconate, or a combination thereof. In other embodiments, the oral composition comprising endoxifen salt is endoxifen HCl or endoxifen citrate. In some embodiments, the subject is administered an oral composition comprising polymorph Form I, Form II or Form III of endoxifen disclosed herein.

Provided herein are methods of treating a subject with a hormone-dependent breast disorder or hormone-dependent reproductive tract disorder, the method comprising: (a) dosing the subject with a first composition comprising tamoxifen; (b) determining or having determined the subject's tamoxifen-metabolites profile in a test sample obtained from the subject; (c) determining a reduced level of subject's plasma endoxifen based on the subject's tamoxifen-metabolites profile to compared to a level of reference plasma endoxifen in a reference tamoxifen-metabolites profile; and (d) administering an oral composition comprising endoxifen or a salt or polymorph thereof to the subject. In certain embodiments, the composition comprising endoxifen is endoxifen gluconate, endoxifen HCl, or endoxifen citrate. In some embodiments, the composition comprises polymorph Form I, Form II, or Form III of endoxifen.

Provided herein are methods for adjusting plasma endoxifen levels in a subject being treated for hormone-dependent breast disorder or hormone-dependent reproductive tract disorder who has one or more CYP2D6 or CYP3A4 mutations or has previously administered with initial dosage of tamoxifen, and who has a plasma endoxifen level less than reference plasma endoxifen level, the method comprising: (a) measuring the subject's plasma endoxifen level after initial dosage of tamoxifen; (b) comparing the subject's plasma endoxifen levels to the reference plasma endoxifen level; (c) administering an oral composition comprising endoxifen or a salt or polymorph thereof to the subject to maintain the subject's plasma endoxifen level at levels greater than 30 nM. In some embodiments, administration of the oral composition comprising endoxifen or a salt or polymorph thereof maintains the subject's plasma endoxifen at levels ranging from 30 nM to 300 nM (e.g., from 30 nM to 200 nM, or from 30 nM to 80 nM). In some embodiments, the subject's plasma endoxifen level is maintained at a steady state level. The subject may be administered with initial dosage of tamoxifen daily for at least 1 day, 2 days, 3 days, 15 days, 1 week, 2 weeks, 4 weeks, 1 month, 2 months, 3 months, 4 months, 5 months, or 6 months.

Provided herein are methods for adjusting the level of plasma endoxifen in a subject being treated for hormone-dependent breast disorder or hormone-dependent reproductive tract disorder who has been previously administered an initial dosage of tamoxifen and who has a level of plasma endoxifen less than 30 nM, the method comprising: (a) measuring the level of plasma tamoxifen-metabolite endoxifen of the subject after the initial dosage of tamoxifen; (b) comparing the plasma level of tamoxifen-metabolite endoxifen to the reference level for normal tamoxifen-metabolite endoxifen level; (c) administering an adjusting dosage of a composition comprising synthetically prepared endoxifen, wherein the dosage of synthetically prepared endoxifen is sufficient to maintain the subject's plasma endoxifen at a level greater than 30 nM. In some embodiments, administration of the second composition comprising a synthetically prepared endoxifen maintains the subject's plasma endoxifen at levels ranging from 30 nM to 300 nM (e.g., from 30 nM to 200 nM, from 30 nM to 80 nM). In some embodiments, the steps (a) to (c) may be repeated until the subject exhibits a desired plasma level of endoxifen.

In an aspect, the present disclosure contemplates a method of treating a subject having or at risk of having a hormone-dependent breast disorder, a hormone-dependent reproductive tract disorder, or both, the method comprising resection of breast tissue of the subject or administering radiotherapy to the subject and administering an oral composition comprising endoxifen or a salt or polymorph thereof disclosed herein. In another aspect, the present disclosure contemplates a method of treating a subject having or at risk of having a hormone-dependent breast disorder, a hormone-dependent reproductive tract disorder, or both, the method comprising administering an oral composition disclosed herein prior to resection of breast tissue of the subject or administering radiotherapy to the subject.

Dosage to be administered to a subject will be usually in a unit dosage form. Examples of ranges for endoxifen in each dosage unit form are from 0.01 mg to 200 mg. Dosage shall generally be an effective amount and equivalent, on a molar basis, of the pharmacologically active (Z)-free form produced by a dosage formulation upon metabolic release of the active free drug to achieve its desired pharmacological and physiological effects. In some embodiments, the compositions comprising endoxifen or an endoxifen salt or polymorph are administered to the subject at a dose of 0.01 mg to 200.0 mg. In other embodiments, the oral compositions comprising endoxifen or an endoxifen salt or polymorph are administered to the subject at a dose of 1 mg to 200.0 mg. In some embodiments, the oral compositions comprising endoxifen or an endoxifen salt or polymorph are administered to the subject at a dose of 0.01 mg, 0.05 mg, 0.1 mg, 0.25 mg, 0.5 mg, 0.75 mg, 1.0 mg, 1.5 mg, 2.0 mg, 4.0 mg, 6 mg, 8 mg, 10 mg, 20 mg, 40 mg, 50 mg, 100 mg or 200 mg per unit dose. In certain embodiments, the oral compositions comprising at least 90% (Z)-endoxifen (wt/wt) of endoxifen are administered at a dose of 1 mg, 2.0 mg, 4.0 mg 6 mg, 8 mg, 10 mg, 20 mg, 40 mg, 50, 100 mg or 200 mg per unit dose. In some embodiments, the compositions comprising endoxifen gluconate are administered at a dose ranging from 0.01 to 20 mg. In some embodiments, a composition comprising (Z)-endoxifen D-gluconate is administered at 0.5 mg, 1 mg, 2 mg 4.0 mg, 6 mg, 8 mg, 10 mg, 20 mg, 40 mg, 50 mg, 100 mg, and 200 mg per unit dose. In some embodiments, a composition comprising 1 mg of (Z)-endoxifen D-gluconate is administered. In other embodiments, a composition comprising 1 mg of (Z)-endoxifen L-gluconate is administered. In yet other embodiments, a composition comprising 2 mg of (Z)-endoxifen D-gluconate and (E)-endoxifen D-gluconate is administered. In certain embodiments, an oral composition comprising at least 90% of a polymorph, such as polymorph Form I, Form II or Form III, of endoxifen (wt/wt) is administered at a dose of 1 mg, 2.0 mg, 4.0 mg 6 mg, 8 mg, 10 mg, 20 mg, 40 mg, 50, 100 mg or 200 mg per unit dose. In some embodiments, a composition comprising a polymorphic form, such as Form I, Form II or Form III, of endoxifen is administered at a dose ranging from 0.01 to 20 mg.

Breast cancer growth rate studies have shown, using mammographic screening of subjects with breast cancer, that the breast cancer growth rate in the 25$^{th}$ percentiles of women ages 50 to 59 indicate an unmet need for fast exposure of the subject to therapeutics (Weeden-Fekjaer et al. Breast Cancer Research 200810:R41). Rapid absorption and bioavailability of the anti-cancer therapeutics such as endoxifen that can further reduce the cancer growth rate is highly desirable.

In one aspect, rapid achievement of maximal and steady state plasma levels of endoxifen is a particular aspect of the present disclosure. The present disclosure provides that administration of compositions disclosed herein to a subject achieves a maximal plasma level of endoxifen ranging within 2 to 30 hours, within 3 to 20 hours, within 2 to 10 hours or within 4 to 8 hours after administration of the compositions. Accordingly, in some embodiments, time to maximal (peak) plasma level of endoxifen ranges from 2 to 10 hours after administration of the compositions. In some embodiments, the time to maximal plasma level of endoxifen ranges from 4 to 8 hours after administration of composition disclosed herein.

Rapid achievement of steady-state plasma levels of endoxifen is also highly desirable. Plasma levels of endoxifen in a subject administered with a composition disclosed herein comprising (Z)-endoxifen or a salt or polymorph thereof rapidly achieves steady state. Steady state plasma levels can be achieved from day 7 to day 21. In some embodiments, the steady state plasma levels can be achieved by day 7 (FIG. 5) following daily administration of a composition disclosed herein.

In an aspect, the present provides that circulating endoxifen released from compositions disclosed herein can be cleared faster than tamoxifen. Terminal elimination half life of tamoxifen is said to be 5-7 days (Jordan C. Steroids. 2007 November; 72(13): 829-842) and peak concentration time of tamoxifen is approximately 5 hours post-dose. Endoxifen released from a composition disclosed herein can have a terminal elimination half-life ranging from 30 to 60 hours, significantly lower than tamoxifen. In some embodiments, the mean half-life ranges from 40 to 53 hours. Mean Ratio of $AUC_{24hr}$ (Day 21)/$AUC_{0-inf}$ (Day1) typically ranges from 0.7 to 1.2 for compositions comprising 1 mg to 4 mg (Z)-endoxifen or a salt or polymorph thereof. Thus, accumulation of endoxifen released from the compositions disclosed herein do not significantly vary over continued treatment.

In another aspect, the present disclosure provides that administration of compositions disclosed herein achieve absorption of endoxifen that is therapeutically effective.

Area under Curve $AUC_{(0-24hr)}$ ("$AUC_{24hr}$") describes the total exposure of the subject to a drug from time of dosing (0 hr) over a 24 hour period. Compositions comprising (Z)-endoxifen or a salt thereof typically achieve mean ($AUC_{24hr}$) of 150 hr*ng/mL to 600 hr*ng/mL on Day 1 of initial (first) dose of compositions comprising 1 mg to 4 mg of (Z)-endoxifen. Compositions comprising (Z)-endoxifen or salts thereof typically achieve mean $AUC_{24hr}$ of 400 hr*ng/mL to 2500 hr*ng/mL on Day 21 of initial (first) dose of compositions comprising 1 mg to 4 mg of (Z)-endoxifen.

$AUC_{(0-inf)}$ ("$AUC_{0-inf}$"), a time-averaged concentration of drug circulating in the body fluid analyzed (normally plasma, blood or serum), describes the total exposure of the subject to a drug. The present provides that the exposure of subjects to endoxifen ($AUC_{0-inf}$) can be dose proportional. In some embodiments, $AUC_{0-inf}$ ranges from 200 hr*ng/mL to 10000 hr*ng/mL. In other embodiments, the $AUC_{0-inf}$ ranges from 300 hr*ng/mL to 8000 hr*ng/mL. In certain embodiments, the $AUC_{0-inf}$ ranges from 400 hr*ng/mL to 6000 hr*ng/mL over the dosing range of 1 mg to 4 mg of (Z)-endoxifen (for example, see Table 17).

A healthcare professional, such as an attending physician, may adjust the dosing regimen based on the pharmacokinetic profile of the composition in the subject.

In one aspect, the compositions of the disclosure can be used alone or in a combination therapy. For example, compositions disclosed herein may be used in combination with one or more therapeutic agents as part of primary therapy, neoadjuvant therapy, or an adjuvant therapy. It is an aspect of the present disclosure that the compositions of the disclosure can be used in combination with other therapies such as surgery and radiation as neo-adjuvant or adjuvant therapy. Combinations of the compositions may act to improve the efficacy of the therapeutic agents, and therefore can be used to improve standard cancer therapies. For example, when a subject has prostate cancer and is on bicalutamide or enzalutamide therapy for the treatment of prostate cancer, the subject is likely to develop gynecomastia a result of the therapy. The compositions disclosed herein can be administered as a combination therapy to the subject having prostate cancer in order to prevent and/or treat gynecomastia. As another example, a subject with ER+/Her2+ positive breast cancer would be on a combination therapy with trastuzumab or other oncology drugs such as anti-neoplastics or immunotherapy, and a composition disclosed herein can be used to treat such a subject with ER+/Her2+ positive breast cancer. Accordingly, in some embodiments, the compositions further comprise bicalutamide, enzalutamide or anticancer drugs such as trastuzumab, antineoplastics such as capecitabine (Xeloda), carboplatin (Paraplatin), cisplatin (Platinol), cyclophosphamide (Neosar), docetaxel (Docefrez, Taxotere), doxorubicin (Adriamycin), pegylated liposomal doxorubicin (Doxil), epirubicin (Ellence), fluorouracil (5-FU, Adrucil), gemcitabine (Gemzar), methotrexate (multiple brand names), paclitaxel (Taxol), protein-bound paclitaxel (Abraxane), vinorelbine (Navelbine), eribulin (Halaven), ixabepilone (Ixempra), and ATP-cassette binding protein inhibitors.

In another aspect, a composition disclosed herein may comprise therapeutic agents that increase bioavailability of endoxifen in a subject. P-glycoprotein (P-gp, ABCB1) is a highly efficient drug efflux pump expressed in brain, liver, and small intestine, but also in cancer cells, that affects pharmacokinetics and confers therapy resistance for many anticancer drugs. Accordingly, in some embodiments, the compositions further comprise inhibitors of ATP-binding cassette (ABC family) transporters, such as inhibitors of breast cancer resistance protein (BCRP protein) and P-gp. Several inhibitors of BCRP protein and P-Gp are known in the art. For example, inhibitors of BCRP protein include cyclosporine, omeprazole, pantoprazole, saquinavir, and tacrolimus.

Non-limiting examples of P-gp inhibitors include first generation inhibitors such as Verapamil, cyclosporin A, reserpine, quinidine, yohimbine, tamoxifen and toremifene, second generation inhibitors such as Dexverapamil, dexniguldipine, valspodar (PSC 833), and Dofequidar fumarate (MS-209), third generation P-gp inhibitors such as Cyclopropyldibenzosuberane zosuquidar (LY335979), laniquidar (R101933), mitotane (NSC-38721), biricodar (VX-710), elacridar (GF120918/GG918), ONT-093, tariquidar (XR9576), and HM30181 and anti-P-gp monoclonal antibodies such as MRK-16).

The present disclosure additionally provides for therapeutic kits containing one or more of the compositions for use in the treatment of a subject having or at risk of having a hormone-dependent breast disorder, a hormone-dependent reproductive tract disorder, or both. The kits of the present disclosure may include an oral composition disclosed herein, a sealed container for housing the composition, and instructions for use of the orally administered composition. In an aspect, the kits of the present disclosure can include a second therapeutic agent. Such a second therapeutic agent may be bicalutamide, enzalutamide or an anticancer drug such as trastuzumab, antineoplasitcs such as capecitabine (Xeloda), carboplatin (Paraplatin), cisplatin (Platinol), cyclophosphamide (Neosar), docetaxel (Docefrez, Taxotere), doxorubicin (Adriamycin), pegylated liposomal doxorubicin (Doxil), epirubicin (Ellence), fluorouracil (5-FU, Adrucil), gemcitabine (Gemzar), methotrexate (multiple brand names), paclitaxel (Taxol), protein-bound paclitaxel (Abraxane), vinorelbine (Navelbine), eribulin (Halaven), ixabepilone (Ixempra), and ATP-binding cassette (ABC transporter) inhibitors such as P-gp inhibitors.

Exemplary Compositions

Exemplary, non-limiting compositions are provided below. As mentioned above, percentages (%) refer to amounts by weight based upon the total weight of the composition (wt/wt). The sum of the different components of the composition adds up to 100% (wt/wt) of the total composition. The at least 90% (≥90%) (Z)-endoxifen free base refers to the percent weight of (Z)-endoxifen isomer as compared to the total weight of endoxifen in any composition.

In an aspect, the present disclosure relates to industrially scalable processes for manufacturing (Z)-endoxifen, compounds of Formula (III), the compound of Formula (II), and salts and polymorphs thereof.

In an aspect, the present disclosure relates to an industrially scalable process for manufacturing (Z)-endoxifen, comprising the steps of: (a) reacting a mixture of (E)-endoxifen and (Z)-endoxifen, compounds of Formula (III), to 6N HCL (1:1 to 1:5 wt/wt) in EtOAc (1:1 to 1:20 wt/wt), (b) neutralizing with 8N NaOH (1:1 to 1:20 wt/wt); (c) washing one or more times with EtOAc (1:1 to 1:10 wt/wt); (d) extracting with 20% NaCl (1:1 to 1:5 wt/wt); (e) reacting with activated carbon (1:0.01 to 1:1); (f) washing one or more times with IPA (1:1 to 1:10 wt/wt) and extracting with MeOH/PPW (1:1 to 1:10 wt/wt); wherein the wt/wt is with respect to the mixture of (E)-endoxifen and (Z)-endoxifen, e.g., compounds of Formula (III).

In an aspect, the present disclosure relates to an industrially scalable process for manufacturing a mixture of (E)-endoxifen and (Z)-endoxifen (compounds of Formula (III)), comprising: (a) reacting the compound of Formula (II) with propiophenone in THF (4.4 wt/wt); (b) preparing a solution of $TiCl_4$ (1.4 wt/wt) and Zn (0.9 wt/wt) in THF (8.9 wt/wt); and (c) reacting the compound of Formula (II) of step (a) with $TiCl_4$ and Zn in THF from step (b) to form a mixture of (E)-endoxifen and (Z)-endoxifen; wherein wt/wt is with respect to the compound of Formula (II).

In an aspect, the present disclosure relates to an industrially scalable process for manufacturing a mixture of (E)-endoxifen and (Z)-endoxifen, compounds of Formula (III), comprising one or more steps of: (a) extraction with 25% ammonium chloride (1:20 wt/wt) and silica (Celite) (1:1 wt/wt); (b) one or more washes with THF (1:1 to 1:5 wt/wt); (c) one or more washes with 20% sodium chloride (1:3 wt/wt); (c) distillation with EtOAc (1:4.5 wt/wt); and (d) crystallization with (1:2 v/v) EtOAc/n-heptane (1:3.8 wt/wt); wherein the wt/wt is with respect to the compound of Formula (II).

In an aspect, the present disclosure relates to an industrially scalable process for manufacturing a mixture of (E)-endoxifen and (Z)-endoxifen, compounds of Formula (III), further comprising one or more steps of: (a) extraction one or more times with 40% $K_2CO_3$ (1:2 wt/wt); (b) extraction with 1N NaOH (1:10 wt/wt) and MeTHF (1:1 to 1:10 wt/wt); (c) two more extractions with MeTHF (1:1 to 1:20 wt/wt); (d) extraction with 20% sodium chloride (1:5 wt/wt); (e) distillation with IPA (1:4.5 wt/wt); and (f) crystallization with (1:2.7 v/v) IPA/n-heptane (1:3.4 wt/wt); wherein the wt/wt is with respect to the compound of Formula (II).

In an aspect, the present disclosure relates to an industrially scalable process for manufacturing the compound of Formula (II), comprising the steps of: (a) reacting the compound of Formula (I) (1 equiv.) with DIPEA (3 wt/wt) in THF (4.9 wt/wt); (b) adding 1-chloroethyl chloroformate (3.3 wt/wt); (c) distilling one to five times with methanol (4.0 wt/wt); (d) distilling with methanol (3.2 wt/wt); (e) reacting with methanol (3.2 wt/wt)/6N HCl (4 wt/wt); and (f) neutralizing with 8N NaOH (5 wt/wt); and wherein wt/wt is with respect to the compound of Formula (I).

In an aspect, the present disclosure relates to (Z)-endoxifen, (E)-endoxifen, compounds of Formula (III), and the compound of Formula (II), and salts thereof, prepared according to processes described herein. In an aspect, the present disclosure relates to (Z)-endoxifen prepared according to a process disclosed herein, wherein the (Z)-endoxifen is stable at ambient temperature for at least 6 months, at least 9 months, at least 12 months, or at least 18 months.

In another aspect, the (Z)-endoxifen free based prepared in accordance with the processes disclosed herein have <1% impurity. In still another aspect, the (E)/(Z)-endoxifen free base prepared in accordance with the processes disclosed herein has <1% impurity.

In an aspect, the present disclosure relates to compositions comprising (Z)-endoxifen free base or a salt thereof prepared according to any of the methods disclosed herein.

In another aspect, the present disclosure relates to compositions comprising (Z)-endoxifen free base or a salt thereof prepared according to any of the methods disclosed herein, wherein the (Z)-endoxifen is at least 90% (Z)-endoxifen free base wt/wt of total endoxifen in the composition.

In still another aspect, the compositions further comprise (E)-endoxifen, wherein the ratio of (E)-endoxifen to (Z)-endoxifen (E/Z-ratio) is 1:99; 5:95; 10:90, 15:85; 20:80, 25:75; 30:70; 40:70, 45:55; 50:50; 55:45; 60:40; 65:45; or 70:30.

In a further aspect, the compositions further comprise (E)-endoxifen, wherein the E/Z-ratio ranges from 45:55 to 55:45 or is approximately 1:1.

In an aspect, the compositions comprise (Z)-endoxifen or a salt or polymorph thereof prepared according to any of the methods disclosed herein, wherein the (Z)-endoxifen is stable at ambient temperature for at least 6 months, at least 9 months, at least 12 months or at least 18 months;

In another aspect, the compositions comprise (Z)-endoxifen or salts thereof prepared according to any of the methods disclosed herein,
a. wherein the compositions have aerobic bacterial plate count of not more than 20,000 g/mL;
b. wherein water content of the compositions is not more than 1.0% as tested by Method Ic of the USP 921;
c. wherein the water activity (Aw) of the compositions is less than 0.9,
d. wherein the residue on ignition is not more than 0.1% as tested by a method of USP 281;
e. wherein a heavy metal is not more than 20 ppm as tested by Method II of USP 231; or
f. wherein methanol is NMT 3000 ppm, tetrahydrofuran is NMT 720 ppm, isopropanol is NMT 5000 ppm, ethyl acetate is NMT 5000 ppm; n-Heptane is NMT 5000 ppm, and ethanol is NMT 5000 ppm as tested by a validated HPLC method In still another aspect, the compositions comprising (Z)-endoxifen or salts thereof prepared according to any of the methods disclosed herein comprise 0.01 mg to 200 mg (Z)-endoxifen or a salt or polymorph thereof per unit dose.

In yet another aspect, the compositions comprising (Z)-endoxifen or salts thereof prepared according to any of the methods disclosed herein comprise 1 mg to 20 mg of (Z)-endoxifen or a salt or polymorph thereof per unit dose.

In a further aspect, the compositions comprising (Z)-endoxifen or salts thereof prepared according to any of the methods disclosed herein comprise 0.01% to 20% (wt/wt) of endoxifen or a salt or polymorph thereof.

In a still further aspect, the present disclosure relates to compositions comprising (Z)-endoxifen or salts thereof prepared according to any of the methods disclosed herein, wherein the composition comprises 0.1% to 10% (wt/wt) of (Z)-endoxifen or a salt or polymorph thereof.

In another aspect, the present disclosure relates to compositions comprising (Z)-endoxifen or salts thereof prepared according to any of the methods disclosed herein further comprising one or more excipient.

In yet another aspect, the present disclosure relates to compositions comprising (Z)-endoxifen or salts thereof prepared according to any of the methods disclosed herein, further comprising one or more excipient, wherein the excipient is a binder, a filler, a disintegrating agent, a lubricant, a glidant, a control release agent, an enteric coating agent, a film forming agent, a plasticizer, a sweetening agent, a flavoring agent, or a combination thereof.

In still another aspect, the present disclosure relates to compositions comprising (Z)-endoxifen or salts thereof prepared according to any of the methods disclosed herein, further comprising one or more excipient, wherein the excipients are about 0.1% to about 99% wt/wt of the composition.

In a further aspect, the present disclosure relates to a composition comprising (Z)-endoxifen or salts thereof prepared according to any of the methods disclosed herein, wherein the composition comprises one or more control release agents selected from the group consisting of acid-insoluble polymers, methyl acrylate-methacrylic acid copolymers, cellulose acetate phthalate (CAP), cellulose acetate succinate, hydroxypropyl methyl cellulose phthalate, hydroxypropyl methyl cellulose acetate succinate (hypromellose acetate succinate), polyvinyl acetate phthalate (PVAP), methyl methacrylate-methacrylic acid copolymers, shellac, cellulose acetate trimellitate, sodium alginate, zein, waxes, including synthetic waxes, microcrystalline waxes, paraffin wax, carnauba wax, and beeswax, polyethoxylated castor oil derivatives, hydrogenated oils, glyceryl mono-, di-tribenates, glyceryl monostearate, glyceryl distearate, long chain alcohols, such as stearyl alcohol, cetyl alcohol, polyethylene glycol, and mixtures thereof.

In one aspect, the present disclosure relates to a composition comprising (Z)-endoxifen or salts thereof prepared according to any of the methods disclosed herein, wherein the composition is formulated for oral, parenteral, topical, and intraductal delivery.

In another aspect, the present disclosure relates to a composition comprising (Z)-endoxifen or salts thereof prepared according to any of the methods disclosed herein, wherein the composition formulated for oral delivery is a tablet, a caplet, a capsule, a pill, a powder, a troche, an elixir, a suspension, a syrup, a wafer, a chewing gum, a dragee, and a lozenge.

In yet another aspect, the present disclosure relates to compositions comprising (Z)-endoxifen or salts thereof prepared according to any of the methods disclosed herein, wherein the compositions formulated for oral delivery are tablets formulated as enteric tablets, caplets formulated as enteric caplets, and capsule formulated as enteric capsules.

In yet another aspect, the present disclosure relates to compositions comprising (Z)-endoxifen or salts thereof prepared according to any of the methods disclosed herein, wherein the compositions formulated for oral delivery are tablets formulated as delayed-release tablets, caplets formulated as delayed-release caplets, or capsules formulated as delayed-release capsules.

In yet another aspect, the present disclosure relates to a composition comprising (Z)-endoxifen or salts thereof prepared according to any of the methods disclosed herein, wherein the composition is formulated for oral delivery, and wherein as tested by a method of USP 711 or 701, the composition releases in stomach:
 a. less than 10% of endoxifen in 2 hours after administration;
 b. less than 20% of endoxifen in 2 hours after administration;
 c. less than 30% of endoxifen in 2 hours after administration;
 d. less than 40% of endoxifen in 4 hours after administration; or
 e. less than 50% of endoxifen in 6 hours after administration.

In still another aspect, the present disclosure relates to a composition comprising (Z)-endoxifen or salts thereof prepared according to any of the methods disclosed herein, wherein the composition is formulated for oral delivery, and wherein as tested by a method of USP 711 or 701, the composition releases in stomach:
 a. less than 10% of (Z) endoxifen in 2 hours after administration;
 b. less than 20% of (Z) endoxifen in 2 hours after administration;
 c. less than 40% of (Z) endoxifen in 4 hours after administration; or
 d. less than 50% of (Z) endoxifen in 6 hours after administration.

In another aspect, the present disclosure relates to a composition comprising (Z)-endoxifen or salts thereof prepared according to any of the methods disclosed herein, wherein the composition is formulated for oral delivery, and wherein as tested by a method of USP 711 or 701, the composition releases at least 40%, at least 50%, at least 60%, at least 70%, at least 80%, or at least 90% endoxifen in the intestines.

In another aspect, the present disclosure relates to a composition comprising (Z)-endoxifen or salts thereof prepared according to any of the methods disclosed herein, wherein the composition is formulated for oral delivery, and wherein as tested by a method of USP 711 or 701, the composition releases in the intestines at least 40%, at least 50%, at least 60%, at least 70%, at least 80%, or at least 90% endoxifen in 2 hours after administration.

In another aspect, the present disclosure relates to a composition comprising (Z)-endoxifen or salts thereof prepared according to any of the methods disclosed herein, wherein the composition is formulated for oral delivery, and wherein as tested by a method of USP 711 or 701, the composition releases in the intestines at least 40%, at least 50%, at least 60%, at least 70%, at least 80%, or at least 90% endoxifen in 3 hours after administration.

In another aspect, the present disclosure relates to a composition comprising (Z)-endoxifen or salts thereof prepared according to any of the methods disclosed herein, wherein the composition is formulated for oral delivery, and wherein as tested by a method of USP 711 or 701, the composition releases in the intestines at least 40%, at least 50%, at least 60%, at least 70%, at least 80%, or at least 90% endoxifen in 4 hours after administration.

In another aspect, the present disclosure relates to a composition comprising (Z)-endoxifen or salts thereof prepared according to any of the methods disclosed herein, wherein the composition is formulated for oral delivery, and wherein as tested by a method of USP 711 or 701, the composition releases in small intestine:
 a. at least 10% of endoxifen after 4 hours after administration;
 b. at least 30% of endoxifen after 6 hours after administration;
 c. at least 40% of endoxifen after 7 hours after administration;
 d. at least 50% of endoxifen after 8 hours after administration;
 e. at least 50% of endoxifen after 2 hours after administration;
 f. at least 60% of endoxifen after 2 hours after administration;
 g. at least 70% of endoxifen after 2 hours after administration;
 h. at least 80% of endoxifen after 2 hours after administration; or
 i. at least 90% of endoxifen after 2 hours after administration.

In another aspect, the present disclosure relates to a composition comprising (Z)-endoxifen or salts thereof prepared according to any of the methods disclosed herein, wherein the composition is formulated for oral delivery, and wherein as tested by a method of USP 711, the composition is formulated to release at least 50% of endoxifen after 8 hours after administration in the colon.

In another aspect, the present disclosure relates to a composition formulated for oral administration comprising: 1 mg to 200 mg of endoxifen per unit dose; and wherein the composition is stable for at least 6 months.

In another aspect, the present disclosure relates to a composition formulated for oral administration comprising: 1 mg to 200 mg of endoxifen per unit dose;
 wherein the endoxifen is at least 90% (Z)-endoxifen free base; and
 wherein:
  the composition has an aerobic bacterial plate count of not more than 20,000 g/ml;
  water content of the (Z)-endoxifen is not more than 1% as determined by Method Ic of the USP 921;
  residue on ignition of the (Z)-endoxifen is not more than 0.10% as tested by a method of USP 281; or
  a heavy metal is not more than 20 ppm as tested by Method II of USP 231.

In another aspect, the present disclosure relates to a composition formulated for oral administration comprising: 1 mg to 200 mg of endoxifen per unit dose,
 wherein the composition is formulated as an enteric tablet, an enteric caplet, and an enteric capsule;
 wherein as determined by a method of USP 711, the composition is formulated to release in small intestine:
  at least 25% of endoxifen after 4 hours after administration;
  at least 30% of endoxifen after 6 hours after administration;
  at least 40% of endoxifen after 7 hours after administration; or
  at least 50% of endoxifen after 8 hours after administration; or
 wherein as determined by a method of USP 711, the composition is formulated to release at least 50% of endoxifen in the colon.

In another aspect, the present disclosure relates to an oral solid dosage form composition comprising: 1 mg to 200 mg of endoxifen per unit dose;
wherein the endoxifen is at least 90% (Z)-endoxifen free base; and
wherein
the composition has an aerobic bacterial plate count of not more than 20,000 g/ml;
water content of the (Z)-endoxifen is not more than 1% as determined by Method Ic of the USP 921;
residue on ignition of the (Z)-endoxifen is not more than 0.10% as tested by a method of USP 281; or
a heavy metal is not more than 20 ppm as tested by Method II of USP 231; and
wherein the composition is formulated as an enteric tablet, an enteric caplet and an enteric capsule; and
wherein the endoxifen is neat; or
wherein the composition further comprises an excipient selected from the group consisting of a binder, a filler, a disintegrating agent, a lubricant, a glidant, a control release agent, an enteric coating agent, a film forming agent, a plasticizer, a colorant, a sweetening agent, and a flavoring agent, or a combination thereof.

In another aspect, the present disclosure relates to an enteric capsule, comprising (Z)-endoxifen free base prepared by a process described herein.

In another aspect, the present disclosure relates to an enteric capsule comprising 1 mg to 200 mg of neat endoxifen per unit dose:
wherein the endoxifen is at least 90% (Z)-endoxifen free base; and
wherein
the composition has an aerobic bacterial plate count of not more than 20,000 g/ml;
water content of the (Z)-endoxifen is not more than 1% as determined by Method Ic of the USP 921;
residue on ignition of the (Z)-endoxifen is not more than 0.10% as tested by a method of USP 281; and
a heavy metal is not more than 20 ppm as tested by Method II of USP 231.

In another aspect, the present disclosure relates to a composition comprising (Z)-endoxifen or a salt or polymorph thereof prepared by any of the processes described herein, wherein the endoxifen salt is selected from the group consisting of arecoline, besylate, bicarbonate, bitartarate, butylbromide, citrate, camysylate, gluconate, glutamate, glycollylarsanilate, hexylresorcinate, hydrabamine, hydrobromide, hydrochloride, hydroxynapthanoate, isethionate, malate, mandelate, mesylate, methylbromide, methylbromide, methylnitrate, methylsulfate, mucate, napsylate, nitrate, pamaoate (Embonate), pantothenate, phosphate/diphosphate, polygalacuronate, salicylate, stearate, sulfate, tannate, Teoclate, triethiodide, benzathine, clemizole, chloroprocaine, choline, diethylamine, diethanolamine, ethylenediamine, meglumine, piperazine, procaine, aluminum, barium, bismuth, lithium, magnesium, potassium, and zinc.

In yet another aspect, the present disclosure relates to a composition comprising (Z)-endoxifen or a salt or polymorph thereof prepared by any of the processes described herein, wherein the endoxifen salt is endoxifen gluconate.

In still another aspect, the present disclosure relates to a composition comprising (Z)-endoxifen or a salt or polymorph thereof prepared by any of the processes described herein, wherein the endoxifen salt is endoxifen gluconate selected from the group consisting of (Z)-endoxifen D-gluconate, (E)-endoxifen D-gluconate, (Z)-endoxifen L-gluconate, and (E)-endoxifen L-gluconate, or a combination thereof.

In still another aspect, the present disclosure relates to a composition comprising (Z)-endoxifen or a salt or polymorph thereof prepared by any of the processes described herein, wherein the endoxifen salt is endoxifen gluconate, and wherein the endoxifen gluconate comprises 1%, 5%, 10%, 20%, 25%, 30%, 40%, 50%, 60%, 70%, 80%, 90%, 95%, 96%, 97%, 98%, 99%, 99.5%, 99.99% or 100% (wt/wt) of (Z)-endoxifen D-gluconate or (Z)-endoxifen L-gluconate.

In still another aspect, the present disclosure relates to a composition comprising (Z)-endoxifen or a salt or polymorph thereof prepared by any of the processes described herein, wherein the endoxifen salt is endoxifen gluconate, and wherein the endoxifen gluconate comprises (Z)-endoxifen D-gluconate and (E)-endoxifen D-gluconate (wt/wt) at Z/E-ratio of 10:90, 20:80, 30:70; 40:60; 50:50, 60:40, 70:30, 80:20, 90:10; 91:9; 92:8; 93:7; 94:8; 95:5, 96:4, 97:3, 98:2, 99:1; 99.5:0.5; or 99.99:0.01.

In still another aspect, the present disclosure relates to a composition comprising (Z)-endoxifen or a salt or polymorph thereof prepared by any of the processes described herein for the treatment and prevention of a hormone-dependent breast disorder, a hormone-dependent reproductive tract disorder, or both.

In still another aspect, the present disclosure relates to a composition comprising (Z)-endoxifen or a salt or polymorph thereof prepared by any of the processes described herein for the treatment and prevention of a hormone-dependent breast disorder, a hormone-dependent reproductive tract disorder, or both, wherein the hormone-dependent breast disorder or the hormone-dependent reproductive tract disorder is a benign breast disorder, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancer, or vulvar cancer.

In still another aspect, the present disclosure relates to a composition comprising (Z)-endoxifen or a salt or polymorph thereof prepared by any of the processes described herein for the treatment and prevention of a hormone-dependent breast disorder, a hormone-dependent reproductive tract disorder, or both, wherein the hormone-dependent breast disorder is breast cancer.

In still another aspect, the present disclosure relates to a composition comprising (Z)-endoxifen or a salt or polymorph thereof prepared by any of the processes described herein for the treatment and prevention of a hormone-dependent breast disorder, a hormone-dependent reproductive tract disorder, or both, wherein the hormone-dependent breast disorder is breast cancer and wherein the breast cancer is a pre-cancer, an early stage cancer, a non-metastatic cancer, a pre-metastatic cancer, a locally advanced cancer, or a metastatic cancer.

In still another aspect, the present disclosure relates to a composition comprising (Z)-endoxifen or a salt or polymorph thereof prepared by any of the processes described herein for the treatment and prevention of a hormone-dependent breast disorder, a hormone-dependent reproductive tract disorder, or both, wherein the hormone-dependent breast disorder or the hormone-dependent reproductive tract disorder is tamoxifen-refractory or tamoxifen resistant.

In still another aspect, the present disclosure relates to a composition comprising (Z)-endoxifen or a salt or polymorph thereof prepared by any of the processes described herein, wherein the composition is administered to a subject in need thereof.

In still another aspect, the present disclosure relates to a composition comprising (Z)-endoxifen or a salt or polymorph thereof prepared by any of the processes described herein, wherein the composition is administered to a subject in need thereof and wherein the subject has or is at risk of having a hormone-dependent breast disorder, a hormone-dependent reproductive tract disorder, or both.

In still another aspect, the present disclosure relates to a composition comprising (Z)-endoxifen or a salt or polymorph thereof prepared by any of the processes described herein, wherein the composition is administered to a subject in need thereof, wherein the subject's hormone-dependent breast disorder or the hormone-dependent reproductive tract disorder is a benign breast disorder, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancer, or vulvar cancer.

In still another aspect, the present disclosure relates to a composition comprising (Z)-endoxifen or a salt or polymorph thereof prepared by any of the processes described herein, wherein the composition is administered to a subject in need thereof, wherein the subject has breast cancer and wherein breast cancer is a pre-cancer, an early stage cancer, a non-metastatic cancer, a pre-metastatic cancer, a locally advanced cancer, or a metastatic cancer.

In still another aspect, the present disclosure relates to a composition comprising (Z)-endoxifen or a salt or polymorph thereof prepared by any of the processes described herein, wherein the composition is administered to a subject in need thereof, wherein the subject has prostate cancer and wherein the subject has or is about to initiate prostate cancer therapy.

In still another aspect, the present disclosure relates to a composition comprising (Z)-endoxifen or a salt or polymorph thereof prepared by any of the processes described herein, wherein the composition is administered to a subject in need thereof, wherein the subject has prostate cancer, and wherein the subject has or is at risk of having gynecomastia.

In still another aspect, the present disclosure relates to a composition comprising (Z)-endoxifen or a salt or polymorph thereof prepared by any of the processes described herein, wherein the composition is administered to a subject that has or is at risk of having a hormone-dependent breast disorder, a hormone-dependent reproductive tract disorder, or both, and wherein the subject's hormone-dependent breast disorder or the hormone-dependent reproductive tract disorder is tamoxifen-refractory or tamoxifen resistant.

In still another aspect, the present disclosure relates to a composition comprising (Z)-endoxifen or a salt or polymorph thereof prepared by any of the processes described herein, wherein the composition is administered to the subject at a unit dose of 0.01 mg, 0.05 mg, 0.1 mg, 0.25 mg, 0.5 mg, 0.75 mg, 1.0 mg, 1.5 mg, 2.0 mg, 4 mg, 5 mg, 10 mg, 20 mg, 25 mg, 50 mg or 200 mg of (Z)-endoxifen.

In still another aspect, the present disclosure relates to a composition comprising (Z)-endoxifen or a salt or polymorph thereof prepared by any of the processes described herein, wherein the composition is administered to the subject at a dose of 0.01 mg, 0.05 mg, 0.1 mg, 0.25 mg, 0.5 mg, 0.75 mg, 1.0 mg, 1.5 mg, 2.0 mg, 4 mg, 5 mg, 10 mg, 20 mg, 25 mg, 50 mg or 200 mg of (Z)-endoxifen.

In still another aspect, the present disclosure relates to a composition comprising (Z)-endoxifen or a salt or polymorph thereof prepared by any of the processes described herein, wherein the composition is administered to the subject once a day, twice a day, thrice a day, four times a day, every other day, twice a week, weekly, fortnightly, twice a month, monthly, quarterly, once every six months, or annually.

In still another aspect, the present disclosure relates to a composition comprising (Z)-endoxifen or a salt or polymorph thereof prepared by any of the processes described herein, wherein administration of the composition orally maintains the subject's plasma endoxifen at a level greater than 30 nM.

In still another aspect, the present disclosure relates to a composition comprising (Z)-endoxifen or a salt or polymorph thereof prepared by any of the processes described herein, wherein the composition is administered to a subject as combination therapy.

In still another aspect, the present disclosure relates to a composition comprising (Z)-endoxifen or a salt or polymorph thereof prepared by any of the processes described herein, wherein the composition is administered as a primary therapy, a neo-adjuvant therapy, or an adjuvant therapy.

In still another aspect, the present disclosure relates to a composition comprising (Z)-endoxifen or a salt or polymorph thereof prepared by any of the processes described herein, wherein the composition is administered to a subject either alone in combination with a second therapeutic agent.

In still another aspect, the present disclosure relates to a composition comprising (Z)-endoxifen or a salt or polymorph thereof prepared by any of the processes described herein, wherein the composition is administered to a subject either alone in combination with a second therapeutic agent, and wherein the second therapeutic agent is bicalutamide, enzalutamide, or an anticancer drug such as trastuzumab, antineoplastic such as capecitabine (Xeloda), carboplatin (Paraplatin), cisplatin (Platinol), cyclophosphamide (Neosar), docetaxel (Docefrez, Taxotere), doxorubicin (Adriamycin), PEGylated liposomal doxorubicin (Doxil), epirubicin (Ellence), fluorouracil (5-FU, Adrucil), gemcitabine (Gemzar), methotrexate (multiple brand names), paclitaxel (Taxol), protein-bound paclitaxel (Abraxane), vinorelbine (Navelbine), eribulin (Halaven), ixabepilone (Ixempra), or inhibitors of ATP-binding cassette transporters.

In still another aspect, the present disclosure relates to a method of treating a subject in need thereof comprising administering a composition prepared according to any one of the processes disclosed herein.

In still another aspect, the present disclosure relates to a method of treating a subject in need thereof comprising administering a composition comprising (Z)-endoxifen or a salt or polymorph thereof prepared according to any one of the processes disclosed herein.

In still another aspect, the present disclosure relates to a method of treating a subject in need thereof comprising administering a composition comprising (Z)-endoxifen or a salt or polymorph thereof prepared according to any one of the processes disclosed herein, wherein the subject has or is at risk of having a hormone-dependent breast disorder, a hormone-dependent reproductive tract disorder, or both.

In still another aspect, the present disclosure relates to a method of treating a subject in need thereof comprising administering a composition comprising (Z)-endoxifen or a salt or polymorph thereof prepared according to any one of the processes disclosed herein, wherein the subject has or is at risk of having a hormone-dependent breast disorder, a hormone-dependent reproductive tract disorder, or both, wherein the hormone-dependent breast disorder or the hormone-dependent reproductive tract disorder is a benign breast disorder, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancer, or vulvar cancer.

In still another aspect, the present disclosure relates to a method of treating a subject in need thereof comprising administering a composition comprising (Z)-endoxifen or a salt or polymorph thereof prepared according to any one of the processes disclosed herein, wherein the subject has breast cancer.

In still another aspect, the present disclosure relates to a method of treating a subject in need thereof comprising administering a composition comprising (Z)-endoxifen or a salt or polymorph thereof prepared according to any one of the processes disclosed herein, wherein the subject has breast cancer, and wherein the breast cancer is a pre-cancer, an early stage cancer, a non-metastatic cancer, a pre-metastatic cancer, a locally advanced cancer, or a metastatic cancer.

In still another aspect, the present disclosure relates to a method of treating a subject in need thereof comprising administering a composition comprising (Z)-endoxifen or a salt or polymorph thereof prepared according to any one of the processes disclosed herein, wherein the subject has prostate cancer and wherein the subject further has or is at risk of having gynecomastia.

In still another aspect, the present disclosure relates to a method of treating a subject in need thereof comprising administering a composition comprising (Z)-endoxifen or a salt or polymorph thereof prepared according to any one of the processes disclosed herein, wherein the subject has tamoxifen-refractory or tamoxifen resistant hormone-dependent breast disorder or hormone-dependent reproductive tract disorder.

In still another aspect, the present disclosure relates to a method of treating a subject in need thereof comprising administering a composition comprising (Z)-endoxifen or a salt or polymorph thereof prepared according to any one of the processes disclosed herein, wherein the composition is administered to the subject at a unit dose of 0.01 mg, 0.05 mg, 0.1 mg, 0.25 mg, 0.5 mg, 0.75 mg, 1.0 mg, 1.5 mg, 2.0 mg, 4 mg, 5 mg, 6 mg, 8 mg, 10 mg, 20 mg, 25 mg, 50 mg, 100 mg or 200 mg.

In still another aspect, the present disclosure relates to a method of treating a subject in need thereof comprising administering a composition comprising (Z)-endoxifen or a salt or polymorph thereof prepared according to any one of the processes disclosed herein, wherein the composition is administered once a day, twice, a day, thrice a day, four times a day, every other day, twice a week, weekly, fortnightly, twice a month, monthly, quarterly, once every six months, or annually.

In still another aspect, the present disclosure relates to a method of treating a subject in need thereof comprising administering a composition comprising (Z)-endoxifen or a salt or polymorph thereof prepared according to any one of the processes disclosed herein, wherein administration of the composition orally maintains the subject's plasma endoxifen at a steady state level greater than 30 nM.

In still another aspect, the present disclosure relates to a method of treating a subject in need thereof comprising administering a composition comprising (Z)-endoxifen or a salt or polymorph thereof prepared according to any one of the processes disclosed herein, wherein administration of the composition orally achieves the subject's plasma endoxifen at a steady state level greater than 30 nM by day 14 after the administration of the first dose (on day 1).

In still another aspect, the present disclosure relates to a method of treating a subject in need thereof comprising administering a composition comprising (Z)-endoxifen or a salt or polymorph thereof, wherein administration of the composition orally achieves the subject's plasma endoxifen at a steady state level greater than 30 nM by day 14 after the administration of the first dose (on day 1).

In still another aspect, the present disclosure relates to a method of treating a subject in need thereof comprising administering a composition comprising (Z)-endoxifen or a salt or polymorph thereof prepared according to any one of the processes disclosed herein, wherein administration of the composition orally achieves a time to maximal plasma levels of endoxifen in the subject from 2 to 10 hours after administration (post-dose).

In still another aspect, the present disclosure relates to a method of treating a subject in need thereof comprising administering a composition comprising (Z)-endoxifen or a salt or polymorph thereof, wherein administration of the composition orally achieves a time to maximal plasma levels of endoxifen in the subject from 2 to 10 hours after administration (post-dose).

In still another aspect, the present disclosure relates to a method of treating a subject in need thereof comprising administering a composition comprising (Z)-endoxifen or a salt or polymorph thereof, wherein the mean terminal elimination half-life of endoxifen in the subject ranges from 30 to 60 hours post dose.

In still another aspect, the present disclosure relates to a method of treating a subject in need thereof comprising administering a composition comprising (Z)-endoxifen or a salt or polymorph thereof, wherein the mean terminal elimination half-life of endoxifen in the subject ranges from 40 to 55 hours post dose.

In another aspect, the present disclosure relates to a method of treating a subject having or at risk of having a hormone-dependent breast disorder, a hormone-dependent reproductive tract disorder, or both, the method comprising administering an oral composition comprising (Z)-endoxifen or a salt or polymorph thereof, wherein administration of the composition achieves:
  a. a mean half-life of endoxifen in the subject ranging from 30 hours to 60 hours after administration;
  b. a time to maximum plasma levels of endoxifen ranging from 2 hours to 10 hours after administration; and
  c. a steady state plasma level of endoxifen greater than 30 nM.

In another aspect, the present disclosure relates to a method of treating a subject having or at risk of having a hormone-dependent breast disorder or a hormone-dependent reproductive tract disorder selected from the group consisting of benign breast disorders, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancer, and vulvar cancer, the method comprising administering an oral composition comprising (Z)-endoxifen or a salt or polymorph thereof, wherein administration of the composition achieves:

a. a mean half-life of endoxifen in the subject ranging from 30 hours to 60 hours after administration;
b. a time to maximum plasma levels of endoxifen ranging from 2 hours to 10 hours after administration; and
c. a steady state plasma level of endoxifen greater than 30 nM.

In another aspect, the present disclosure relates to a method of treating a subject having or at risk of having a hormone-dependent breast disorder or a hormone-dependent reproductive tract disorder selected from the group consisting of benign breast disorders, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancera and vulvar cancer, the method comprising administering an oral composition comprising (Z)-endoxifen or a salt or polymorph thereof formulated as an enteric tablet, an enteric caplet, an enteric capsule, a delayed-release tablet, a delayed-release caplet, or a delayed-release capsule, wherein administration of the composition achieves:
a. a mean half-life of endoxifen in the subject ranging from 30 hours to 60 hours after administration;
b. a time to maximum plasma levels of endoxifen ranging from 2 hours to 10 hours after administration; and
c. a steady state plasma level of endoxifen greater than 30 nM.

In another aspect, the present disclosure relates to a method of treating a subject having or at risk of having a hormone-dependent breast disorder or a hormone-dependent reproductive tract disorder selected from the group consisting of benign breast disorders, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancer, and vulvar cancer, the method comprising administering an oral composition comprising (Z)-endoxifen or a salt or polymorph thereof formulated as an enteric tablet, an enteric caplet, an enteric capsule, a delayed-release tablet, a delayed-release caplet, or a delayed-release capsule, wherein administration of the composition achieves:
a. a mean half-life of endoxifen in the subject ranging from 30 hours to 60 hours after administration;
b. a time to maximum plasma levels of endoxifen ranging from 2 hours to 10 hours after administration; and
c. a steady state plasma level of endoxifen greater than 30 nM; and
wherein at least 50%, at least 60%, at least 70%, at least 80% or at least 90% of the endoxifen is released in the intestines.

In another aspect, the present disclosure relates to a method of treating a subject having or at risk of having a hormone-dependent breast disorder or a hormone-dependent reproductive tract disorder selected from the group consisting of benign breast disorders, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancer, and vulvar cancer, the method comprising administering an oral composition comprising 0.01 mg to 200 mg of (Z)-endoxifen or a salt or polymorph thereof formulated as an enteric tablet, an enteric caplet, an enteric capsule, a delayed-release tablet, a delayed-release caplet, or a delayed-release capsule, wherein administration of the composition achieves:

a. a mean half-life of endoxifen in the subject ranging from 30 hours to 60 hours after administration;
b. a time to maximum plasma levels of endoxifen ranging from 2 hours to 10 hours after administration; and
c. a steady state plasma level of endoxifen greater than 30 nM; and
wherein at least 50%, at least 60%, at least 70%, at least 80% or at least 90% of the endoxifen is released in the intestines.

In another aspect, the present disclosure relates to a method of treating a subject having or at risk of having a hormone-dependent breast disorder or a hormone-dependent reproductive tract disorder selected from the group consisting of benign breast disorders, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancer, and vulvar cancer, the method comprising administering daily an oral composition comprising 0.01 mg to 200 mg of (Z)-endoxifen or a salt or polymorph thereof formulated as an enteric tablet, an enteric caplet, an enteric capsule, a delayed-release tablet, a delayed-release caplet, or a delayed-release capsule, wherein administration of the composition achieves:
a. a mean half-life of endoxifen in the subject ranging from 30 hours to 60 hours after administration;
b. a time to maximum plasma levels of endoxifen ranging from 2 hours to 10 hours after administration; and
c. a steady state plasma level of endoxifen greater than 30 nM.

In another aspect, the present disclosure relates to a method of treating a subject having or at risk of having a hormone-dependent breast disorder or a hormone-dependent reproductive tract disorder selected from the group consisting of benign breast disorders, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancer, and vulvar cancer, the method comprising administering daily an oral composition comprising 0.01 mg to 200 mg of (Z)-endoxifen or a salt or polymorph thereof formulated as an enteric tablet, an enteric caplet, an enteric capsule, a delayed-release tablet, a delayed-release caplet, or a delayed-release capsule, wherein administration of the composition achieves:
a. a mean half-life of endoxifen in the subject ranging from 30 hours to 60 hours after administration;
b. a time to maximum plasma levels of endoxifen ranging from 2 hours to 10 hours after administration; and
c. a steady state plasma level of endoxifen greater than 30 nM; and
wherein at least 50%, at least 60%, at least 70%, at least 80% or at least 90% of the endoxifen is released in the intestines.

In another aspect, the present disclosure relates to a method of treating a subject having or at risk of having a hormone-dependent breast disorder or a hormone-dependent reproductive tract disorder selected from the group consisting of benign breast disorders, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancer, and vulvar cancer, the method comprising administering daily an oral composition comprising 0.01 mg to 200 mg of (Z)-endoxifen or a salt or polymorph thereof formulated as an enteric tablet, an enteric caplet, an enteric capsule, a delayed-release tablet, a delayed-release caplet, or a delayed-release capsule, wherein administration of the composition achieves:
  a. a mean half-life of endoxifen in the subject ranging from 30 hours to 60 hours after administration;
  b. a time to maximum plasma levels of endoxifen ranging from 2 hours to 10 hours after administration; and
  c. a steady state plasma level of endoxifen greater than 30 nM;

wherein the mean area under the curve extrapolated to time infinity ($AUC_{0-inf}$) is 200 hr*ng/mL to 10000 hr*ng/mL, 300 hr*ng/mL to 8000 hr*ng/mL, 400 hr*ng/mL to 6000 hr*ng/mL or 700 hr*ng/mL to 6000 hr*ng/mL; and
  wherein at least 50%, at least 60%, at least 70%, at least 80% or at least 90% of the endoxifen is released in the intestines.

In still another aspect, the present disclosure relates to a method of treating a subject in need thereof comprising administering a composition comprising (Z)-endoxifen or a salt or polymorph thereof prepared according to any one of the processes disclosed herein, wherein the method is a primary therapy, a neo-adjuvant therapy, or an adjuvant therapy.

In still another aspect, the present disclosure relates to a method of treating a subject in need thereof comprising administering a composition comprising (Z)-endoxifen or a salt or polymorph thereof prepared according to any one of the processes disclosed herein, wherein a composition is administered to a subject as combination therapy.

In still another aspect, the present disclosure relates to a method of treating a subject in need thereof comprising administering a composition comprising (Z)-endoxifen or a salt or polymorph thereof prepared according to any one of the processes disclosed herein, wherein a composition is administered to a subject either alone in combination with a second therapeutic agent.

In still another aspect, the present disclosure relates to a method of treating a subject in need thereof comprising administering a composition comprising (Z)-endoxifen or a salt or polymorph thereof prepared according to any one of the processes disclosed herein, wherein a composition is administered to a subject with a second therapeutic agent selected from the group consisting of bicalutamide, enzalutamide, or an anticancer drug such as trastuzumab, antineoplastics such as capecitabine (Xeloda), carboplatin (Paraplatin), cisplatin (Platinol), cyclophosphamide (Neosar), docetaxel (Docefrez, Taxotere), doxorubicin (Adriamycin), PEGylated liposomal doxorubicin (Doxil), epirubicin (Ellence), fluorouracil (5-FU, Adrucil), gemcitabine (Gemzar), methotrexate (multiple brand names), paclitaxel (Taxol), protein-bound paclitaxel (Abraxane), vinorelbine (Navelbine), eribulin (Halaven), ixabepilone (Ixempra), and ATP-cassette binding protein transport inhibitors.

In still another aspect, the present disclosure relates to a use for the treatment and prevention of a hormone-dependent breast disorder, a hormone-dependent reproductive tract disorder, or both, in a subject, the use comprising:
  dosing the subject with a first composition comprising tamoxifen;
  determining the subject's tamoxifen-metabolites profile in a test sample obtained from the subject;
  determining a reduced level of subject's plasma endoxifen based on subject's tamoxifen-metabolites profile as to compared to a level of plasma endoxifen in a reference tamoxifen-metabolites profile; and
  administering to the subject a composition of the present disclosure.

In still another aspect, the present disclosure relates to a use for the treatment and prevention of a hormone-dependent breast disorder, a hormone-dependent reproductive tract disorder, or both, in a subject, the use comprising:
  dosing the subject with a first composition comprising tamoxifen;
  determining the subject's tamoxifen-metabolites profile in a test sample obtained from the subject;
  determining a reduced level of subject's plasma endoxifen based on subject's tamoxifen-metabolites profile as to compared to a level of plasma endoxifen in a reference tamoxifen-metabolites profile; and
  administering to the subject a composition of the present disclosure;
  wherein the composition is administered orally in a dose sufficient to maintain the subject's plasma endoxifen at a steady state level greater than 30 nM;
  wherein the tamoxifen-metabolites profile comprises a panel of at least tamoxifen, 4-hydroxytamoxifen, n-desmethyltamoxifen, or endoxifen;
  wherein the hormone-dependent breast disorder or the hormone-dependent reproductive tract disorder is a benign breast disorder, hyperplasia, atypia, atypical ductal hyperplasia, atypical lobular hyperplasia, increased breast density, gynecomastia, DCIS, LCIS, breast cancer, precocious puberty, McCune-Albright Syndrome, endometrial cancer, ovarian cancer, uterine cancer, cervical cancer, vaginal cancer, or vulvar cancer;
  wherein the hormone-dependent breast disorder is a precancer, an early stage cancer, a non-metastatic cancer, a pre-metastatic cancer, a locally advanced cancer, or metastatic cancer;
  wherein the hormone-dependent breast disorder is a non-metastatic cancer;
  wherein the subject has prostate cancer, and wherein the subject further has or is at risk of having gynecomastia; or
  wherein the hormone-dependent breast disorder or hormone-dependent reproductive tract disorder is tamoxifen-refractory or tamoxifen resistant.

In still another aspect, the present disclosure relates to a kit for treating a subject having or at risk of having a hormone-dependent breast disorder or hormone dependent reproductive tract disorder, in a subject in need thereof comprising: (a) a composition of the present disclosure; and (b) a sealed container for housing the composition; and c) instructions for use of the orally administered composition.

In still another aspect, the present disclosure relates to a kit for treating a subject having or at risk of having a hormone-dependent breast disorder or hormone dependent reproductive tract disorder, in a subject in need thereof comprising: (a) a composition of the present disclosure; and (b) a sealed container for housing the composition; and c) instructions for use of the orally administered composition, wherein the kit comprises a second therapeutic agent selected from the group consisting of bicalutamide, enzalutamide and anticancer drugs such as trastuzumab, antineoplastics such as capecitabine (Xeloda), carboplatin (Paraplatin), cisplatin (Platinol), cyclophosphamide (Neosar), docetaxel (Docefrez, Taxotere), doxorubicin (Adriamycin), PEGylated liposomal doxorubicin (Doxil), epirubicin (Ellence), fluorouracil (5-FU, Adrucil), gemcitabine (Gemzar), methotrexate (multiple brand names), paclitaxel (Taxol), protein-bound paclitaxel (Abraxane), vinorelbine (Navelbine), eribulin (Halaven), ixabepilone (Ixempra), and ATP-cassette binding protein transport inhibitors.

In still another aspect, the present disclosure relates to a method of administering a composition prepared in accordance with any of the processes described herein to a subject in need thereof in accordance with instructions for use comprised in a kit comprising the composition.

EXAMPLES

Abbreviations used herein
ACN/PPW=Acetonitrile/Process Purified Water
$NaHCO_3$=Sodium hydrocarbonate
HCl=hydrochloric acid
THF=Tetrahydrofuran
MeTHF=2-Methyltetrahydrofuran
$CH_2Cl_2$=Dicholoromethane
EtOH=Ethanol
MeOH=Methanol
EtOAc=Ethyl acetate
IPA=Isopropyl alcohol; isopropanol
TFA=Trifluoroacetic acid
TCA=Trichloroacetic acid
PPW=Process Purified Water
IPA/PPW=Isopropyl alcohol/Process Purified Water Example 1: Enrichment and Preparation of (Z)-Endoxifen Free Base A. Fractional Crystallization (Z)-Endoxifen free base (drug substance) can be prepared from a mixture of (E)-endoxifen and (Z)-endoxifen by fractional crystallization described herein. Briefly, commercially available crude endoxifen mixture of (E)-endoxifen and (Z)-endoxifen isoforms (Astatech Ltd. China) were used as starting material to prepare (Z)-endoxifen as free base.

i. An E/Z-endoxifen solution was prepared by suspending 1 g of endoxifen having (E)-endoxifen and (Z)-endoxifen at each of temperatures 50° C. and 23° C. were taken and monitored by HPLC-UV to determine their E/Z-endoxifen ratio. The (Z)-endoxifen enriched filtrates and the E-endoxifen enriched filtrates were added back to their respective mother liquors.

HPLC-UV analyses of the samples was carried out using a Luna phenyl-hexyl column (4.6 mm×150 mm×3 μm of particle size). The column temperature was 40° C. and sample compartment temperature was maintained at ambient temperature. Samples were prepared by dissolving solids and filtrates at 0.2 mg/ml of sample in methanol as sample buffer. Samples were then injected into the column in an injection volume of 20 μl. Likewise, mildly acidic (pH 4.3) ammonium formate buffer/methanol in the mobile phase with gradient elution was used. Mobile phase system consisting of: Mobile Phase A (MPA) buffer was 10 mM $HCOONH_4$ with 0.03% HCOOH buffer in water, and Mobile Phase B (MBP) buffer was 10 mM $HCOONH_4$ in methanol with a gradient program used.

TABLE 1

| Gradient Program | | |
|---|---|---|
| Time (m) | MPA (%) | MPB (%) |
| 0 | 50 | 50 |
| 15 | 30 | 70 |
| 25 | 5 | 95 |
| 30 | 50 | 50 |

The run time was 30 m, the flow rate was 1.0 mL/m, and the delay time was 5 m. Samples were detected by UV detection at 243 nm. Retention times were typically from 12.95 to 13.20 m for (E)-endoxifen and from 14.0 to 14.33 m for (Z)-endoxifen. Relative Retention Time (RRT) for (E)-endoxifen was 0.4 to 0.9 and 1.0 for (Z)-endoxifen.

TABLE 2

| Enrichment of Endoxifen (Z)- and (E)- isomers from hot slurry of E/Z-endoxifen mixture in IPA and EtOAc. | | | | | | |
|---|---|---|---|---|---|---|
| | Sample | | | | | |
| | 1 | 2 | 3 | 4 | 5 | 6 |
| E/Z-endoxifen ratio | 51/1 | 1/1.8 | 1/5.8 | 51/1 | 1/1.8 | 1/5.8 |
| E/Z-endoxifen Solvent | 1 g | 1 g IPA (10 X) | 1 g | 1 g | 1 g EtOAc (10 X) | 1 g |
| 50° C. Solid | 85/1 (97.0%/1.1%) | N/A (dissolved) | 1/4.2 (18.9%/79.6%) | ≥100/1 (97.9%/0.7%) | 1.9/1 (65.4%/34.2%) | 1/24 (3.9%/94.8%) |
| Filtrate | 12/1 (87.0%/7.0%) | N/A (dissolved) | 1/47 (2.1%/97.4%) | 5.4/1 (66.2%/12.3%) | 1/2.4 (29.2%/68.7%) | 1/2.5 (28.0%/70.1%) |
| 23° C. Solid | ≥100/1 (98.2%/0.3%) | 1/2.1 (31.8%/67.2%) | 1/90 (1.1%/98.1%) | ≥100/1 (99.0%/0.4%) | 1.3/1 (55.9%/43.1%) | 1/6.9 (12.6%/86.9%) |
| Filtrate | 3.6/1 (70.1%/19.6%) | 1/1.7 (36.5%/60.6%) | 1/1.3 (43.4%/54.9%) | 1.6/1 (37.7%/23.0%) | 1/6.7 (12.6%/84.3%) | 1/2.6 (26.2%/84.3%) | ratios (E/Z ratio) of 51/1, 1/1.8, and 1/5.8, each in a 10× volume of the solvent, isopropanol (IPA). A second set of solutions was prepared by suspending 1 g each of endoxifen at E/Z ratios of 51/1, 1/1.8, and 1/5.8 in 10× volume of the solvent EtOAc. The solutions were heated to a first temperature of 50° C. creating a hot slurry and stirred overnight at 50° C. The hot slurry samples were filtered using a cellulose filter pore size 0.5 μm. The mixtures were then cooled to a second temperature, room temperature 23° C. while stirring for 12 hours to effect crystallization. The aliquots of cooled samples were filtered using a cellulose filter pore size 0.5 μm. Aliquots of the solid and filtrates at Results (Table 2) show that Z-endoxifen can be enriched using a commercial crude E/Z-endoxifen starting material from a hot slurry of the endoxifen mixtures made with IPA and EtOAc. Z-endoxifen can be purified from E/Z-endoxifen mixtures having E/Z at 1:1 and with higher Z-endoxifen levels in the mixture, for example, 1:8, and 1:5.8. Substantial Z-endoxifen enrichment was achieved in a single step using fractional crystallization method, for example with an E/Z ratio of 1:90 described herein Example 1A. (Z)-endoxifen was seen to be more soluble than (E)-endoxifen in EtOAc. (Z)-endoxifen also tended to remain in the filtrate in greater amounts in EtOAc as compared with IPA. Both solids and filtrates are useful for the preparation of (Z)-endoxifen free base. Serial enrichment of Z-endoxifen by adding filtrates back to the first filtrate (first mother liquor) can also be performed.

Similarly, E-endoxifen can be purified from E/Z-endoxifen mixture having higher E-endoxifen levels in the E/Z mixture.

ii. Similar results were obtained in experiments where an E/Z-endoxifen mixture was suspended in a hot slurry prepared with a mixture of IPA/PPW (1:1 v/v) and extracted and washed with precooled IPA/PPW (1:1) to form crystalline solids and filtrates with enriched (Z)-endoxifen.

B. Recrystallization from Solid Fraction

Serial enrichment of (Z)-endoxifen can be performed by subjecting the endoxifen mixture with E/Z-endoxifen ratio of 51:1, 1:1.8 and 1:5.6, and the solids and mother liquors obtained from the fractional crystallization to one or more rounds of recrystallization.

The (Z)-endoxifen can be enriched in substantially purified form from crude E/Z-endoxifen mixtures, (Z)-enriched crystalline solids and (Z)-enriched mother liquors by recrystallization with solvents such as ethanol, ethyl acetate/n-heptane, Acetone/MTBE, IPA, IPA/PPW, and the like under the conditions as described herein.

Ethanol. Crystalline solids obtained from E/Z-endoxifen hot IPA slurry mixture above were used to obtain further purified Z-endoxifen. After cooling to 23° C., the solid fractions of sample 2 (80 g) and sample 3 (79 g) of Table 2 above were combined and recrystallized using 1000 mL (1 L) EtOH. The ethanol mixture was heated to reflux. The dissolution point was at 75° C. The heated solution was filtered using a cellulose filter (pore size 0.5 μm) to remove foreign impurities such as cotton fibers by polish filtration. The filtrate solution was then stirred initially at 70° C. for 30 minutes. The solution was then cooled to 0° C.-5° C. and stirred continually for 5 h at 0° C.-5° C. The solution was filtered again. The crystals on the filter were washed with 200 mL of EtOH.

Results show that solid crystals of endoxifen had E/Z ratio of ≥1/100 (0.22%/99.48%) and endoxifen in the filtrate had E/Z ratio of 1/5.9 (13.93%/82.48%) when recrystallized with EtOH. HPLC analysis of at least 3 different experiments conducted by this method showed that (Z) endoxifen retention time was 14.00 m, E-endoxifen retention time was 13.14 m. (Z)-endoxifen levels ranged from 97% to 99.48% while (E)-endoxifen levels ranged from 0.22% to 2.14%. Other impurities were <1%.

Ethyl Acetate/n-heptane. Feasibility of recrystallization with EtOAc/n-heptane was studied as described below.

5 g Endoxifen (E/Z ratio 1/5.8) was added to EtOAc/n-heptane (140 mL, 1/1 v/v) and heated to reflux (~82° C.) while stirring overnight to obtain a clear solution. The cloud point of the mixture was 30° C. The mixture was then cooled to room temperature to precipitate the product and filtered. After isolation as described above, endoxifen of the solid product was determined by HPLC to have an E/Z ratio of 1/8.1 (10.9%:88.60%) with a product yield of 66% (3.3 g). (Z)-Endoxifen in the filtrate was enriched with E/Z ratio of 1:3 (23.94%:74.47%). The recrystallization using EtOAc/n-heptane can also provide purified Z-endoxifen in ratios similar to the hot IPA slurry as shown in Table 3.

TABLE 3

Recrystallization of (Z)-endoxifen from E/Z-endoxifen mixture using EtOAc/n-heptane solvent.

| Parameter | | Result |
|---|---|---|
| E/Z endoxifen-E/Z ratio 1/5.8 | | 5 g |
| EtOAc/n-heptane solvent (1:1) | | 140 mL |
| Heat to dissolution | | ~82° C. (reflux) |
| Cloud point | | ~30° C. |
| Cool to RT and filtration | | 23° C., 1 hr |
| E/Z ratio of the product | Solid | 3.3 g, 1/8.1 |
| | | (10.90%/88.60%) |
| | Filtrate | 1/3.0 (23.94%/72.47%) |

Acetone/MTBE. 0.5 g Endoxifen (E/Z ratio 1/1.8) was added to Acetone (10 v; 5 mL) solvent, and antisolvent MTBE (9 mL) was added to the solution and heated to reflux (~82° C.) while stirring overnight to obtain a clear solution. The cloud point of the mixture was ~22° C. The mixture was then cooled to room temperature to precipitate the product and filtered. Endoxifen in the solid product was determined by HPLC to have an E/Z ratio of 39/1 while the filtrate was enriched with (Z)-endoxifen with E/Z ratio of 1:2.6. Acetone/MTBE solvent system is useful to separate E-endoxifen to solid from the (Z)-endoxifen in the filtrate.

C. Recrystallization from Mother Liquor

Purified (Z)-endoxifen can be recovered from mother liquor enriched with (Z)-endoxifen as shown in the following Tables 4 and 5.

i. Starting material of crude E/Z-endoxifen mixture can be dissolved in a first solvent, ethyl acetate, to form a first mother liquor from which (Z)-endoxifen can be recovered by a second step of addition of a second solvent such as n-heptane or ethanol as shown in Table 4.

TABLE 4

Recrystallization of Z-endoxifen

| | | Results Lot Number | |
|---|---|---|---|
| Parameter | | 1 | 2 |
| E/Z-endoxifen (E/Z = 1/1.8) | | 5 g | 10 g |
| EtOAc (First solvent) | | 50 mL | 50 mL |
| Heat to dissolution | | ~68° C. | ~78° C. (reflux) |
| Cloud Point° | | ~33° C. | ~38° C. |
| Cool to RT and filtration | | 23° C., 1 h | 23° C., 1 h |
| E/Z ratio of product | Solid | 0.87 g, 8.5/1 | 1.53 g, 1/1 |
| | | (89.37%/10.49%) | (49.32%/49.80%) |
| | Filtrate | 1/3.8 (20.13%/76.86%) | 1/2.6 (27.29%/70.09%) |

TABLE 4-continued

Recrystallization of Z-endoxifen

| | Results Lot Number | |
|---|---|---|
| Parameter | 1 | 2 |
| Filtrate concentration | To 5 mL, 25 mL | To dryness |
| Heat to dissolution | ~68° C. | ~68 C. |
| Add solvent/anti-solvent (second solvent) | n-heptane, 40 mL, no precipitation observed | EtOH, 50 mL, heat to dissolution |
| Cool to RT and filtration | 23° C., overnight | 23° C. (cloud point ~28 C.) |
| E/Z ratio of product Solid | 3.0 g, 1/4.2 (18.70%/78.95%) | 3.2 g, 1/12 (7.52%/90.24%) |
| Filtrate | 1/3.2 (21.65%/70.35%) | 1/1.5 (39.35%/57.76%) | ii. (Z)-endoxifen was prepared by a process involving: a first step of dissolving crude E/Z-endoxifen mixture in a first solvent, ethyl acetate, enriching (Z)-endoxifen to first mother liquor; a second step of addition of a second solvent, IPA to form crystalline (Z)-endoxifen and a second mother liquor; and a step of addition of a third solvent ethanol to recrystallize and recover (Z)-endoxifen from the second mother liquor.

Briefly, endoxifen (E/Z=1/1.8, 30 g) and (E/Z=1.2/1, 50 g non-GMP) was dissolved in EtOAc 300 mL and 500 mL respectively, heated to dissolution (~70° C.). The mixture was then cooled to 25° C. while stirring overnight for precipitation. The suspension was filtered and E/Z ratio of solid and the filtrate was determined by HPLC.

Next, the filtrates were concentrated to dryness and IPA 230 mL and 900 mL respectively were added to form hot slurries (50° C.) while stirring. The hot slurries were continuously stirred at 50° C. overnight. The slurries were then cooled to 25° C. for 0.5 h and 1 h respectively, and filtered. Z-endoxifen in the solid and the filtrates were determined again.

The solids of each sample (14.8 g and 21.6 g) were further recrystallized from 148 mL and 220 mL EtOH by heating to dissolution at NMT 70° C. and cooling to 25° C. for 0.5 h and 1 h respectively. The samples were further cooled to 0° C.-5° C. for 1 h and filtered. The E/Z ratio of the solid and the filtrates were again determined by HPLC. E/Z ratios of each sample and purity are provided below in Table 5.

TABLE 5

Recovery of (Z)-endoxifen from (Z)-endoxifen enriched mother liquor

| | | Results Lot Number | |
|---|---|---|---|
| Parameter | | 1 | 2 |
| E/Z-endoxifen ratio | | 1/1.8 | 1.2/1 |
| E/Z-endoxifen amount | | 30 g | 50 g |
| EtOAc | | 300 mL | 500 mL |
| Heat to Dissolution | | ~70° C. | ~70° C. |
| Cloud Point | | ~33° C. | ~33° C. |
| Cool to RT | | 25° C., 3 h | 25° C., overnight |
| E/Z ratio of product | Solid | 4.5/1 (80.52%/17.73%) | 13.5/1 (92.44%/6.83%) |
| | Filtrate | 1/5.0 (16.02%/80.71%) | 1/6.8 (12.34%/84.45%) |
| Filtrate concentration | | To remove EtOAc | Swap with IP (400 ml X 2) |
| Add IPA | | 230 mL | 900 mL |
| Final Volume | | | 250 mL |
| Hot Slurry | | 50° C. overnight | 50° C., overnight |
| Cool to RT and filtration | | 25° C., 4 h | 25° C., 4 h |
| E/Z ratio of product | Solid | 1/31.7 (3.0%/95.15%) | 1.31.9 (2.94%/93.74%) |
| | Filtrate | 1/1.6 (36.16%/58.78%) | 1/1.7 (32.17%/55.92%) |
| E/Z-endoxifen for recrystallization | | 14.8 g | 21.6 g |
| EtOH | | 148 mL | 220 mL |
| Heat to Dissolution | | ~70° C. | ~70° C. |
| Cool to RT | | 25° C., 0.5 h | 25 C., 1 h |
| E/Z ratio of Product | Solid | — | 1/76.9 (1.26%/91.91%) |
| | Filtrate | — | 1/20.1 (4.57%/91.91%) |
| Cool to 0° C.-5° C. and filtration | | 0° C.-5° C., 1 h | 0° C.-5° C., 1 h |
| E/Z ratio of product | Solid (?) | 1/51.8 (1.86%/96.31%) | 1/118.7 (0.82%/97.30%) |
| | Filtrate (?) | 1/6.8 (12.72%/86.23%) | 1/8 (10.54%/84.66%) |
| Total Yield | | 31% | 29% |

Results show that purified crystalline (Z)-endoxifen of greater than 90% can be obtained by subjecting an E/Z-endoxifen mixture to fractional crystallization with a first solvent, ethyl acetate, to form crystalline solid and a first mother liquor, subjecting the first mother liquor to crystallization with a second solvent such as hot IPA to form a second crystalline solid and second mother liquor, and then recrystallization of the solids from a third solvent such as ethanol. A yield of (Z)-endoxifen of greater than 95% is also feasible. The ratio of (E)/(Z)-endoxifen can be improved from ~1.2:1 and 1:1.8 to 1:51 to over 1:118. The impurity profile of (Z)-endoxifen was analyzed by an HPLC method as described above and was found to be less than <2%. Retention time of (Z)-endoxifen and (E)-endoxifen were 14.19 m and 13.2 m respectively.

Example 2: Reequilibriation of (E)-Endoxifen-Rich E/Z-Mixture (E)-endoxifen-rich E/Z-endoxifen mixture is also useful for the preparation Z-endoxifen free base (in addition to being useful for the preparation of purified (E)-endoxifen). (E)-endoxifen-rich E/Z-endoxifen mixture is reequilibriated from a E/Z ratio of ≥1.5:1 (for example, E/Z ratio of 51:1) to about ~1:1 mixture. The present disclosure embraces the idea that reequilibration may be performed with a starting E/Z-endoxifen mixture having any E/Z ratio, such as 99:1 to 1:99. Such reequilibration is useful for preparation of stable (E)/(Z)-endoxifen ~1:1 mixture as well as further enrichment and purification of Z-endoxifen free base as described in Example 1 above.

Briefly, (E)-endoxifen is converted to (Z)-endoxifen by dissolving crude E/Z-endoxifen in an inert solvent such as acetonitrile/water (8:1) or dichloromethane in the presence of an acid such as hydrochloric acid, trichloroacetic acid or trifluoroacetic acid. The reaction mixture with ACN/PPW was stirred at 60° C. for 1 hour while the reaction mixture with dichloromethane and TFA was stirred at RT for 1 hour. After work up was performed as described in Table 6, the E/Z ratio of the product was determined to be E/Z-endoxifen (ratio about 1:1) with a purity greater than 90%.

TABLE 6

Reequilibrium of E/Z-endoxifen (E/Z ratio 51/1) to E/Z ratio of about 1:1

| Parameter | Results Sample 1 | Results Sample 2 |
|---|---|---|
| E/Z-endoxifen (E/Z ratio = 51/1) | 0.5 g (off-white powder) | 0.5 g (off-white powder) |
| Solvent | ACN/PPW = 8/1, 5 mL (white slurry) | CH$_2$Cl$_2$, 5 mL (White slurry) |
| Acid | 6N HCl, 5 mL ~60° C., 6 h | TFA, 5 mL ~23° C., 1 h |

TABLE 6-continued

Reequilibrium of E/Z-endoxifen (E/Z ratio 51/1) to E/Z ratio of about 1:1

| Parameter | Results Sample 1 | Results Sample 2 |
|---|---|---|
| Stir | (Pink solution to clear solution) | (orange clear solution) |
| Work up | Quench with saturated solution of NaHCO$_3$, wash the organic layer with brine and organic layer is evaporated to dryness | Quench with saturated solution of NaHCO$_3$, wash the organic layer with brine and organic layer is evaporated to dryness |
| Product | Beige solid | Off-white solid |
| E/Z ratio | ~1/1 (49.28%/47.70%) | ~1.3/1 (54.51%/41.9%) |
| Purity | 96.98% | 96.20% |

Example 3: Purification of (E)-Endoxifen (E)-endoxifen was similarly purified by recrystallization in EtOH (500 mL) by heating the reaction mixture to NMT 70° C. to get a clear solution, cooled to 0° C.-5° C. to precipitate the product. After purification by methods described herein, 38.1 g of (E)-endoxifen was obtained in 76% yield with 97.6% purity.

Example 4: Scale Up

Synthetic and purification methods disclosed herein also are useful in scaling up the preparation of (Z)-endoxifen for making industrial drug product dosage forms, for example, oral, transdermal/topical, nasal, intraductal parenteral dosage forms, for use clinical use in subjects. Feasibility studies of crystallization using 5 g, 100 g, and 110 g of E/Z-endoxifen mixture, compounds of Formula (III) at an E/Z ratio of 1/5.8 were performed by suspending the E/Z-endoxifen mixtures in 10× volume of IPA and heated to 50° C. and stirred for 4 h at 50° C. The samples were filtered using a cellulose filter pore size 0.5 μm and the E/Z ratio was determined in the solids. Following filtration, the samples were cooled to 23° C. and stirred continuously for 4 h at 23° C. The samples were filtered again. Solids and the filtrates were monitored for (E)-endoxifen and (Z)-endoxifen levels by HPLC as described above and the results are provided below in Table 7.

TABLE 7

Scale up Preparation of (Z)-endoxifen

| Parameter | | Results Sample 1 | Results Sample 2 | Results Sample 3 |
|---|---|---|---|---|
| E/Z-endoxifen ratio 1/5.8 | | 5 g | 100 g | 110 g |
| IPA (10 X) | | 50 mL | 1000 mL | 1100 mL |
| 50° C. | Solid | 1/20 (4.71%/94.50%) | 1/22 (4.25%/94.88%) | 1/16 (5.85%/93.24%) |
| | Filtrate | 1/3.1 (26.54%/72.23%) | 1/2.2 (30.62%/67.52%) | 1/2.3 (29.94%/68.04%) |
| Cooling to 23° C. stirring for 4 h | Solid | 1/78 (1.26%/97.69%) | 1/78 (2.14%/97.24%) | 1/74 (1.32%/98.12%) |
| | Filtrate | 1/1.1 (50/0.75%/47.1%) | 1.1/1 (51.47%/45.88%) | 1.2/1 (53.03%/43.81%) |

Results show that Z-endoxifen can be obtained from an E/Z-endoxifen mixture from IPA solvent at concentrations higher than ≥90% as crystalline solid as well as ≥65% (Z)-endoxifen free base in the filtrate. IPA is thus useful as a first solvent, or second solvent or both.

Example 5: Industrially Scalable Preparation of [4-[2-(methylamino)ethoxy]phenyl](4-hydroxyphenyl)methanone)

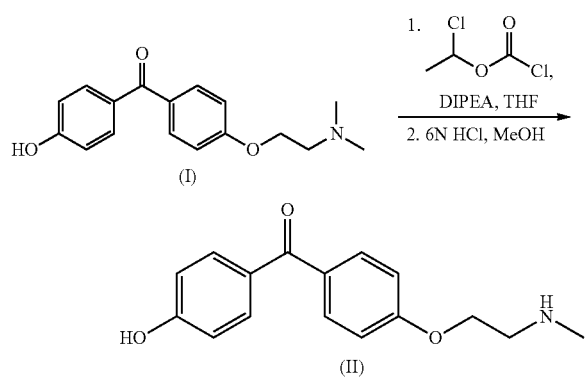

A suitable 10 L reactor was charged with starting material [4-[2-(dimethylamino)ethoxy]phenyl](4-hydroxyphenyl) methanone, the compound of Formula (I) (0.5 kg, 1.0 equiv.), DIPEA (1.5 kg, 6.65 equiv., 3.0 wt./wt.) and tetrahydrofuran (5 L, 10 vol./wt., 8.9 wt./wt.) under N₂ atmosphere. 1-Chloroethyl chloroformate (1.7 kg, 6.65 equiv., 3.3 wt./wt.) was added slowly while maintaining the internal temperature at NMT 20° C. The mixture was heated to reflux and stirred at reflux for NLT 12 hr. The mixture was evaporated under reduced pressure at NMT 75° C. until the volume reached the lowest agitateable volume. Methanol (2.5 L, 5 vol./wt., 4.0 wt./wt.) was added slowly and the mixture was distilled under reduced pressure at NMT 75° C. until the volume reached the lowest agitateable volume. Methanol (2.5 L, 5 vol./wt., 4.0 wt./wt.) was added and the mixture was distilled under reduced pressure at NMT 75° C. until the volume reached the lowest agitateable volume. Methanol (2.5 L, 5 vol./wt., 4.0 wt./wt.) was once again added and the mixture was further distilled under reduced pressure at NMT 75° C. until the volume once again reached the lowest agitateable volume. Methanol (2 L, 4 vol./wt., 3.2 wt./wt.) and 6N HCl (2 L, 4 vol./wt., 4.0 wt./wt.) were added to the mixture and the mixture was heated to reflux. The mixture was stirred at reflux for NLT 12 hr. After reaction completion, the mixture was evaporated under reduced pressure at NMT 75° C. until most of MeOH was removed. The mixture was cooled to 25±5° C. and 8N NaOH (2.5 L, 5 vol./wt., 5.0 wt./wt.) was added slowly until the pH of the mixture was 11-12. The mixture was stirred at 0-5° C. for NLT 2 hr. The mixture was filtered and washed with H₂O (1 L, 2 vol./wt.) and ethyl acetate (1 L, 2 vol./wt., 1.8 wt./wt.). The wet cake was dried at NMT 50° C. under reduced pressure to afford (4-hydroxyphenyl)(4-(2-(methylamino)ethoxy)phenyl)methanone, the compound of Formula (II). Yield: 297 gm, 63%;

Purity: 100% (Expected Yield—60-90%)

Example 6: Industrially Scalable Preparation of [4-[2-(methylamino)ethoxy]phenyl](4-hydroxyphenyl)methanone)

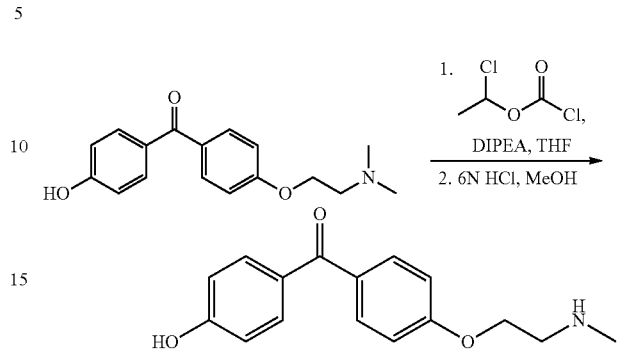

A suitable 2 L reactor was charged with starting material [4-[2-(dimethylamino)ethoxy]phenyl](4-hydroxyphenyl) methanone, the compound of Formula (I) (70 gm, 1.0 equiv.), N-Ethyldiisopropylamine (126 gm, 4.0 equiv., 1.8 wt.) and tetrahydrofuran (700 mL, 10.0 vol., 8.9 wt.) under N₂ atmosphere. The mixture was heated to NLT 60° C. and 1-chloroethyl chloroformate (140 gm, 4.0 equiv., 2.0 wt.) added. The mixture was heated to reflux and stirred for NLT 12 hr. The mixture was concentrated until the volume reached 3 vol. Methanol (350 mL, 5.0 vol., 4.0 wt.) was added slowly and the mixture was concentrated until the volume reached 3 vol. (210 mL). Next, methanol (350 mL, 5.0 vol., 4.0 wt.) was added and the mixture was concentrated until the volume reaches 4 vol. (280 mL). 6N HCl (280 mL, 4.0 vol., 4.0 wt.) was added and the mixture was heated to reflux. The mixture was stirred at reflux for NLT 12 hr. After reaction completion, the mixture was concentrated until the volume reaches ~4 vol. (280 mL). The mixture was cooled to ambient temperature, and 8N NaOH (NLT 350 mL, 5.0 vol., 5.0 wt.) was added slowly until the pH of the mixture is NLT 13. Ethyl acetate (280 mL, 4.0 vol., 3.6 wt.) was added to the mixture for extraction. After phase separation, to the aqueous layer was added 6N HCl (NLT 42 mL, 0.6 vol., 0.6 wt.) until the pH was 8-10. The mixture was cooled to 0±5° C. and stirred for NLT 2 hr. The mixture was filtered and washed with purified water (NLT 140 mL, 2.0 vol., 2.0 wt.) and ethyl acetate (NLT 140 mL, 2 vol., 1.8 wt.). The wet cake was dried at NMT 60° C. under reduced pressure to afford (4-hydroxyphenyl)(4-(2-(methylamino) ethoxy)phenyl)methanone, the compound of Formula (II). Yield: 55.2 gm, 83%; Purity: 100% (Expected Yield—NLT 70%).

Example 7: Industrially Scalable Preparation of E/Z-Endoxifen Mixture in a McMurry Reaction

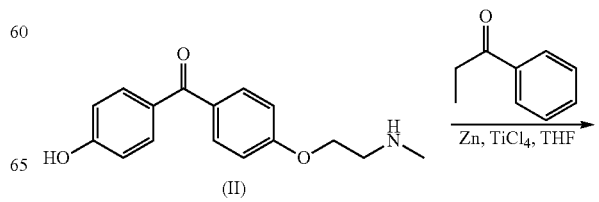

-continued

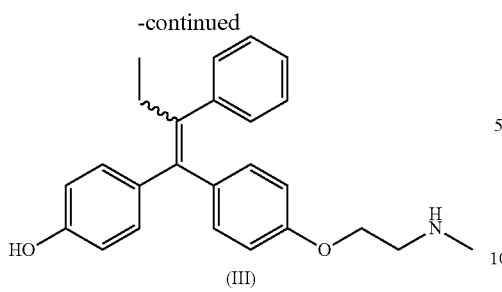

(III)

A suitable 10 L reactor was charged with Zn powder (0.27 kg, 4.0 equiv., 0.9 wt./wt.) and tetrahydrofuran (1.5 L, 5 vol./wt., 4.4 wt./wt.) under N2 atmosphere. TiCl$_4$ (0.42 kg, 2.0 equiv., 1.4 wt./wt.) was added slowly while maintaining the internal temperature at NMT 15° C. The reaction was heated to reflux and stirred at reflux for NLT 2 hr. A suspension of (4-hydroxyphenyl)(4-(2-(methylamino)ethoxy)phenyl)methanone, the compound of Formula (II) obtained from Step 1, (0.297 kg, 1.0 equiv.) and propiophenone (0.21 kg, 1.5 equiv., 0.7 wt./wt.) in tetrahydrofuran (3.0 L, 10 vol./wt., 8.9 wt./wt.) was added and the reflux was continued for NLT 8 hr. The mixture was cooled to 20-30° C. and added into 25% ammonium chloride (5.9 L, 20 vol./wt., 20 wt./wt.)/silica (diatomaceous earth/silicon dioxide; tradename Celite® S) available from Sigma Aldrich (0.3 kg, 1.0 wt./wt.) mixture. The mixture was filtered and washed with tetrahydrofuran (0.9 L, 3 vol./wt., 2.7 wt./wt.).

The mixture was settled for phase separation. The organic layer was collected and the aqueous layer was washed with tetrahydrofuran (0.9 L, 3 vol./wt., 2.7 wt./wt.). The organic layer was again collected and combined with the first organic layer. The combined organic layer was washed with 40% K$_2$CO$_3$ (1.2 L, 4 vol./wt., 5.6 wt./wt.). The organic layer was concentrated at NMT 75° C. under reduced pressure until the volume reached the lowest agitateable volume. Ethyl acetate (1.5 L, 5 vol./wt., 4.5 wt./wt.) was added and the mixture was distilled under reduced pressure at NMT 75° C. until the volume reached the lowest agitateable volume. Ethyl acetate (1.5 L, 5 vol./wt., 4.5 wt./wt.) was added and the mixture was distilled under reduced pressure at NMT 75° C. until the volume reached 5 vol. (1.5 L). The mixture was heated to dissolution and n-heptane (3.0 L, 10 vol./wt., 6.8 wt./wt.) was added. The mixture was cooled to 0±5° C. and stirred at 0±5° C. for NLT 2 hr. The mixture was filtered and the residue was washed with ethyl acetate/n-heptane=1/2 (v/v, 1.5 L, 5 vol./wt., 3.7 wt./wt.). The residue wet cake was dried under reduced pressure at NMT 60° C. to afford a mixture of (Z)-endoxifen and (E)-endoxifen, (E/Z)-4-[1-[4-[2-(Methylamino)ethoxy]phenyl]-2-phenyl-1-buten-1-yl]-phenol, compounds of Formula (III). Yield: 176 g, 42%; Purity: 81.96%. E/Z ratio: 3.1:1 (Expected yield—40-60%).

A suitable 10 L reactor was charged with the above (E/Z)-endoxifen (0.250 kg, 1.0 wt.), isopropanol (1.25 L, 5 vol./wt., 3.9 wt./wt.) and purified water (1.25 L, 5 vol./wt., 5.0 wt./wt.). The mixture was heated to 70±5° C. and stirred at 70±5° C. for NLT 2 hr. The mixture was cooled to 0±5° C. and stirred at 0-5° C. for NLT 2 hr. The mixture was filtered and washed with pre-cooled isopropanol/purified water=1/1 (0.5 L, 2 vol./wt., 3.6 wt./wt.). The residue wet cake was dried at NMT 60° C. to afford a mixture of (Z)-endoxifen and (E)-endoxifen, (E/Z)-4-[1-[4-[2-(Methylamino)ethoxy]phenyl]-2-phenyl-1-buten-1-yl]-phenol, compounds of Formula (III). Yield: 105 g, 41%; Purity: 96.79%. E/Z ratio: 48.6:1 (Expected yield—40-60%).

Example 8: Industrially Scalable Preparation of E/Z-Endoxifen Mixture in a McMurry Reaction

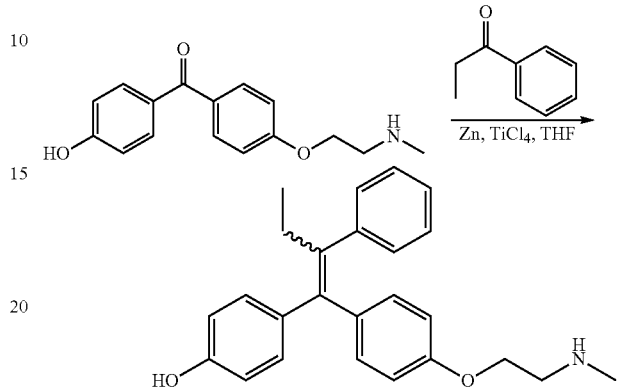

To a suitable reactor was charged zinc powder (10 gm, 4.0 equiv., 1.0 wt.) and tetrahydrofuran (50 mL, 5.0 vol., 4.3 wt.) under N$_2$ atmosphere. Titanium(IV) chloride (14 gm, 2.0 equiv., 1.4 wt.) was added slowly while maintaining the internal temperature at NMT 45° C. The reaction was heated to 65±5° C. and stirred for NLT 2 hr. A suspension of (4-hydroxyphenyl)(4-(2-(methylamino)ethoxy)phenyl)methanone, the compound of Formula (II) obtained from Example 5, (10 gm, 1.0 equiv.) and propiophenone (5 gm, 1.0 equiv., 0.5 wt.) in Tetrahydrofuran (100 mL, 10.0 vol., 8.5 wt.) was added to the above mixture and stirred at 65±5° C. for NLT 8 hr. The mixture is cooled to NMT 30° C. and 40% K$_2$CO$_3$ (20 mL, 2.0 vol., 2.0 wt.) is added. The mixture was stirred for NLT 1 hr. The mixture was filtered and washed with Me-THF (40 mL, 4.0 vol., 3.5 wt.). The filtrate was added to 40% K$_2$CO$_3$ (30 mL, 3.0 vol., 3.0 wt.) and stirred for NLT 30 min. The mixture was filtered and washed with Me-THF (20 mL, 2.0 vol., 1.7 wt.). The filtrate was settled for phase separation and the organic layer is concentrated until the volume reached 3 vol. (30 mL). The mixture was extracted with 1N NaOH (100 mL, 10.0 vol., 10.0 wt.) and the organic layer was discarded. The aqueous layer was added sodium chloride (1 gm, 0.10 wt.) and then extracted 4 times with Me-THF (50 mL, 5.0 vol., 4.3 wt.). The 4 organic layers are combined and concentrated until the volume reached 5 vol. The mixture is extracted with 20% NaCl (50 mL, 5.0 vol., 5.0 wt.). The organic layer was added isopropanol (50 mL, 5.0 vol., 3.9 wt.) and the mixture was concentrated until the volume reached 3 vol. isopropanol (50 mL, 5.0 vol., 4.5 wt.) was added and the mixture is concentrated until the volume reached 3 vol. (30 mL). The mixture was heated to 65±5° C. and n-Heptane (120 mL, 12.0 vol., 8.2 wt.) was added. The mixture was cooled to NMT 5° C. and stirred at NMT 5° C. for NLT 2 hr. The mixture was filtered and washed with n-Heptane (50 mL, 5 vol., 3.4 wt.). The wet cake was dried at NMT 70° C. under reduced pressure to afford a mixture of (Z)-endoxifen and (E)-endoxifen, (E/Z)-4-[1-[4-[2-(Methylamino)ethoxy]phenyl]-2-phenyl-1-buten-1-yl]-phenol, compounds of Formula (III). Yield: 6.7 g, 45%; Purity: 96.79%. E/Z ratio: 48.6:1 (Expected yield—NLT 30%).

Example 9: Industrially Scalable Enrichment of Z-Endoxifen

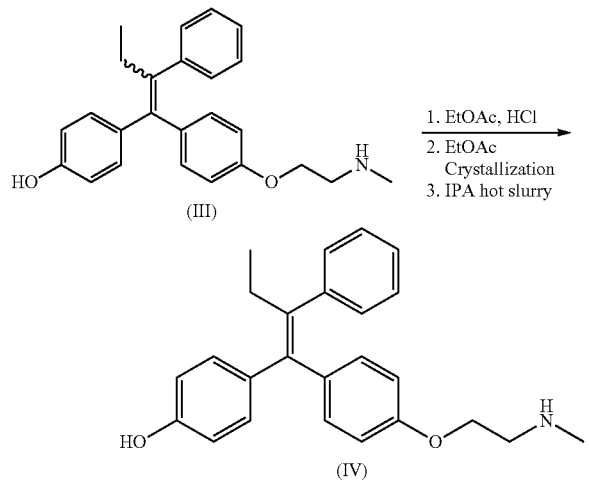

A suitable reactor was charged with the mixture of (Z)-endoxifen and (E)-endoxifen, compounds of Formula III, (0.105 kg, 1.0 wt.) and first solvent, ethyl acetate, (1.1 L, 10 vol./wt., 9.0 wt./wt.). The mixture was cooled to 0-5° C. and 6N HCl (0.3 L, 3 vol./wt., 3.0 wt./wt.) was added slowly to the mixture. The mixture was heated to 60±5° C. and stirred at 60±5° C. for NLT 6 hr. The mixture was cooled to 0±5° C. and 8N NaOH (0.3 L, 3.0 vol./wt., 3.0 wt./wt.) was added slowly until the pH of the mixture was ≥12.

The mixture was settled for phase separation, the organic layer was collected and the aqueous layer was washed with the first solvent, ethyl acetate (0.5 L, 5 vol./wt., 4.5 wt./wt.). The organic layer was collected. The combined organic layers were washed with 20% NaCl (0.3 L, 3 vol./wt., 3.0 wt./wt.). The organic layer was treated with activated carbon (charcoal) (0.005 kg, 0.05 wt.) and stirred at 50±5° C. for NLT 1 hr. The mixture was filtered through a bed of diatomaceous earth/silica (Celite® S) and washed with ethyl acetate (0.5 L, 5 vol./wt., 4.5 wt./wt.). The filtrate was concentrated at NMT 75° C. until the volume reached 10 vol. (1.1 L). The mixture was cooled to 0-5° C. and stirred at 0-5° C. for NLT 2 hr. The mixture was filtered and the filtrate was collected. The filtrate was concentrated at NMT 75° C. until the volume reached the lowest agitateable volume.

A second solvent, isopropanol, (1.1 L, 10 vol./wt., 7.9 wt./wt.) was added and the mixture was concentrated at NMT 75° C. until the volume reached the lowest agitateable volume. Isopropanol (1.1 L, 10 vol./wt., 7.9 wt./wt.) was again added and the mixture was concentrated at NMT 75° C. until the volume reached the lowest agitateable volume. Isopropanol (1.1 L, 10 vol./wt., 7.9 wt./wt.) was added and the mixture was concentrated at NMT 75° C. until the volume reached 5 vol. (0.5 L). The suspension was stirred at 50±5° C. for NLT 6 hr. The mixture was cooled to 20±5° C. and stirred at 20±5° C. for NLT 4 hr. The mixture was filtered and washed with isopropanol (0.2 L, 2 vol./wt., 1.6 wt./wt.). The wet cake was dried at NMT 60° C. to afford purified (Z-endoxifen) solid compound of Formula (IV) as an off-white solid. Yield: 39.5 g, 36%, (E)/(Z) ratio: 1/12.2; Purity (Z): 89.59% by HPLC, Expected Yield (20-40%).

A suitable 1 L reactor was charged with the above Z-endoxifen (39 g) solid compound of Formula (IV) and a third solvent, isopropanol (390 mL, 10 vol./wt.). The suspension was stirred at 50±5° C. for NLT 6 hr. The mixture was cooled to 20±5° C. and stirred at 20±5° C. for NLT 4 hr. The mixture was filtered and washed with isopropanol (78 mL, 2 vol./wt.). The wet cake was dried at NMT 60° C. to afford purified (Z-endoxifen) solid compound of Formula (IV) as an off-white solid. Yield: 25 g, 61%, (E)/(Z) ratio: 1/55.1; Purity (Z): 95.81%, Expected Yield (50-70%).

In this manner, polymorph Form I of endoxifen was prepared. XRPD patterns for two batches of the resultant polymorph are provided in FIGS. 9 and 10. The XRPD peaks from FIGS. 9 and 10 are provided in Table 8.

TABLE 8

| XRPD peaks from FIGS. 9 and 10. | | | |
|---|---|---|---|
| FIG. 9 | | FIG. 10 | |
| Peak Position (°2θ) | Relative Intensity (%) | Peak Position (°2θ) | Relative Intensity (%) |
| 7.1 | 15 | 7.1 | 8 |
| 9.3 | 22 | 9.3 | 13 |
| 12.4 | 8 | 12.3 | 4 |
| 14.2 | 26 | 14.2 | 16 |
| 15.2 | 14 | 15.2 | 10 |
| 16.0 | 20 | 16.0 | 14 |
| 16.8 | 58 | 16.8 | 49 |
| 17.1 | 100 | 17.1 | 100 |
| 18.2 | 40 | 18.2 | 35 |
| 18.6 | 15 | 18.6 | 8 |
| 18.9 | 12 | 18.8 | 8 |
| 19.8 | 14 | 19.9 | 6 |
| 20.9 | 32 | 20.9 | 31 |
| 21.3 | 24 | 21.3 | 19 |
| 21.7 | 53 | 21.8 | 55 |
| 22.5 | 15 | 22.5 | 9 |
| 23.2 | 19 | 23.2 | 9 |
| 24.3 | 30 | 24.4 | 29 |
| 25.3 | 15 | 25.3 | 12 |
| 26.5 | 13 | 26.5 | 11 |
| 26.8 | 20 | 26.9 | 23 |
| 28.0 | 9 | 28.0 | 7 |
| 29.0 | 9 | 29.0 | 9 |

Example 10: Industrially Scalable Enrichment of ~1:1 E/endoxifen/Z-Endoxifen Mixture A suitable reactor was charged with the mixture of (Z)-endoxifen and (E)-endoxifen, compounds of Formula III, (0.420 kg, 1.0 wt.) and ethyl acetate (4.2 L, 10 vol./wt., 9.0 wt./wt.). The mixture was cooled to 0-5° C. and 6N HCl (1.3 L, 3 vol./wt., 3.0 wt./wt.) was added slowly. The mixture was heated to 60±5° C. and stirred at 60±5° C. for NLT 6 hr. The mixture was cooled to 0±5° C. and 8N NaOH (1.3 L, 3.0 vol./wt., 3.0 wt./wt.) was added slowly until the pH of the mixture was ≥12.

The mixture was settled for phase separation, the organic layer was collected and the aqueous layer was washed with ethyl acetate (2.0 L, 5 vol./wt., 4.5 wt./wt.). The organic layer was collected. The combined organic layers were washed with 20% NaCl (1.3 L, 3 vol./wt., 3.0 wt./wt.). The organic layer was treated with activated carbon (charcoal) (0.02 kg, 0.05 wt.) and stirred at 50±5° C. for NLT 1 hr. The mixture was filtered through diatomaceous earth/silica (Celite® S) bed and washed with ethyl acetate (2.0 L, 5 vol./wt., 4.5 wt./wt.). The filtrate was concentrated at NMT 75° C. until the volume reached 5 vol. (2.0 L). The mixture was heated to reflux and then cooled to 50±5° C. n-Heptane was added slowly at 50±5° C. The mixture was cooled to 0±5° C. and stirred at 0±5° C. for NLT 2 hr. The mixture was filtered and washed with EtOAc/n-Heptane=1/2 (v/v). The wet cake was dried under reduced pressure at NMT 60° C. to afford substantially pure ~1:1 E/Z-endoxifen. [Yield: 106 g, 25%; (E)/(Z) ratio: 1.1/1; Purity (E/Z): 97.94%, Expected Yield (20-40%)].

In this manner, polymorph Forms II and III of endoxifen were prepared. Detailed parameters for the preparation of polymorph Forms II and III are provided in Table 9, and XRPD patterns are provided in FIGS. 11-13. The XRPD peaks from FIGS. 11-13 are provided in Table 10

TABLE 9

Parameters for isolation of polymorph Form II and Form III

| Entry | 1 | 2 | 3 |
|---|---|---|---|
| Reactor capacity | 10 L | 10 L | 50 L |
| E/Z-endoxifen input | 0.37 kg | 0.17 kg | 0.83 kg |
| 6N HCL | 1.1 kg (3 vol.) | 0.68 kg (4 vol.) | 3.32 kg (4 vol.) |
| Reaction time | 60° C., 6 hr | 60° C., 6 hr | 60° C., 6 hr |
| E/Z ratio in IPC | 1.1 | 1.1 | 1.1 |
| pH after 8N NaOH neutralization | 14 | 13 | 14 |
| NaCl extraction | 20% NaCl, 1.1 kg | 20% NaCl, 1.0 kg | 5% NaCl, 2.5 kg |
| Org. layer concentrate to 5 vol. | to 1.9 L (5.1 vol.) | to 1 L (5.8 vol.) | to 4 L (4.8 vol.) |
| n-Heptane (10 vol.) addition at 50° C. | 2.5 kg, 40 min | 1.2 kg, 30 min | 5.6 kg, 36 min |
| Agitation at 50° C. | 150 rpm, 40 min | 130 rpm, 1 hr | 150 rpm, 2 hr |
| Cool to 0° C. | 2 hr | 4 hr | 5 hr |
| Agitation at 0° C. | 150 rpm, 2 hr | 140 rpm, 6 hr | 150 rpm, 6 hr |
| Filtration time | 10 min | 10 min | 20 min |
| Drying | 50° C., 4 hr | 68° C., 18 hr | 69° C., 26 hr |
| E/Z ratio of API | 1.1 | 0.92 | 1.1 |
| XRPD pattern | Form II (FIG. 11) | Form III (FIG. 13) | Form II (FIG. 12) |

TABLE 10

XRPD peaks from FIGS. 11, 12 and 13.

| FIG. 11 | | FIG. 12 | | FIG. 13 | |
|---|---|---|---|---|---|
| Peak Position (°2θ) | Relative Intensity (%) | Peak Position (°2θ) | Relative Intensity (%) | Peak Position (°2θ) | Relative Intensity (%) |
| 6.6 | 31 | 6.6 | 33 | 6.6 | 24 |
| 7.0 | 42 | 7.0 | 35 | 7.0 | 21 |
| 9.3 | 16 | 9.3 | 24 | 9.2 | 19 |
| 11.9 | 100 | 11.9 | 100 | 9.6 | 17 |
| 13.3 | 20 | 13.3 | 27 | 11.9 | 55 |
| 14.0 | 96 | 14.0 | 85 | 13.3 | 20 |
| 14.1 | 22 | 14.2 | 34 | 13.9 | 39 |
| 15.1 | 11 | 15.1 | 16 | 16.8 | 50 |
| 16.8 | 13 | 16.8 | 12 | 17.1 | 100 |
| 17.1 | 22 | 17.1 | 20 | 17.7 | 56 |
| 17.7 | 14 | 17.7 | 15 | 18.2 | 38 |
| 18.4 | 69 | 18.4 | 65 | 18.3 | 37 |
| 18.6 | 13 | 18.5 | 17 | 19.9 | 22 |
| 20.0 | 16 | 20.0 | 20 | 20.2 | 18 |
| 20.8 | 35 | 20.8 | 46 | 20.8 | 38 |
| 21.3 | 17 | 21.3 | 29 | 21.3 | 24 |
| 21.7 | 59 | 21.7 | 82 | 21.7 | 56 |
| 22.0 | 16 | 22.0 | 18 | 22.5 | 19 |
| 22.9 | 14 | 22.9 | 19 | 22.9 | 17 |
| 23.2 | 9 | 23.2 | 16 | 23.9 | 26 |
| 23.9 | 17 | 23.9 | 17 | 24.3 | 29 |
| 24.3 | 12 | 24.3 | 14 | 25.3 | 15 |
| | | | | 26.8 | 20 |

Example 11: Stability of Z-Endoxifen Free Base

Commercially, endoxifen is available as an E/Z isomer free base mixture, as well as ≥98% (Z)-endoxifen HCl and (Z)-endoxifen citrate salts. Stability of Z-endoxifen HCl salt in aqueous and solid forms has been previously published (Elkins et al. J Pharm Biomed Anal. 2014 January; 88: 174-179). Elkins et al. provide predicted t90 values for 10% conversion of (Z)-endoxifen HCl to (E)-endoxifen in the solid state of 53 months at 25° C./60% RH and 4.3 months at 40° C./75% RH. Conversion is expected to be more rapid in a solution environment. In an aqueous medium, Elkins et al. provide (Z)-endoxifen HCl t90 values of 149 days at room temperature and 9 days at 45° C. There remains a need for (Z)-endoxifen free base preparations that are sufficiently stable for preparation of pharmaceutical compositions that are suitable for administering to subjects, for example, at ambient temperatures as well as at higher temperature and humidity.

Provided herein in the present disclosure are preparations of endoxifen free base that are substantially pure, at least 90% (Z)-endoxifen free base, and stable for at least 9 months under conditions of ambient and high temperature and humidity. Stability, for the purpose of this disclosure, is defined as the continued presence of at least 90% (Z)-endoxifen in a composition for at least 6 months, and is measurable by (Z)-endoxifen conversion to (E)-endoxifen starting from the date of synthesis.

A. Accelerated 10-day Stability Study of (Z)-Endoxifen Free Base

The stability of (Z)-endoxifen free base Sample 1 of Table 11 was studied when stored at various temperatures in solid form and in ethanol (EtOH) solution. The (E)-endoxifen and (Z)-endoxifen levels were measured on days 2, 7 and 10 following placement of 1 g aliquots of purified (Z)-endoxifen free base in 180 mL HDPE bottles under dry N2, which were then placed in double LDPE bags. The double bagged HDPE bottles containing each sample were individually packed in aluminum foil bags and thermally sealed until they were opened for testing the stability of the samples. The (E)- and (Z)-isomers of endoxifen were monitored by HPLC as disclosed above. The purity of (Z)-endoxifen in solid form remained at about 97% at 40° C., 60° C., and 80° C. up to 10 days. The results of the accelerated 10 days study indicate that (Z)-endoxifen in solid form does not interconvert to (E)-endoxifen at the tested temperatures up to 10 days.

TABLE 11

Accelerated Stability Test of Solid (Z)-endoxifen Free Base

| | No. | | |
|---|---|---|---|
| | 1 | 2 | 3 |
| Z-endoxifen | 1 g | 1 g | 1 g |
| Temperature | 40° C. | 60° C. | 80° C. |
| 2 days E/Z ratio | 1/76 (1.27%/97.45%) | 1/75 (1.30%/97.43%) | 1/76 (1.28%/97.42%) |
| Total Impurity | 1.28% | 1.27% | 1.30% |
| 7 days E/Z ratio | 1/81 (1.2%/97.11%) | 1/83 (1.17%/87.11%) | 1/7 2(1.34%/96.92%) |
| Total Impurity | 1.69% | 1.72% | 1.74% |
| 10 days E/Z ratio | 1/75 (1.29%/97.31%) | 1/82 (1.27%/97.48%) | 1/77 (1.27%/97.33%) |
| Total Impurity | 1.40% | 1.33% | 1.40% |

TABLE 12

Accelerated Stability Study of (Z)-endoxifen Free Base Solution in Ethanol

| | No. | | | |
|---|---|---|---|---|
| | 1 | 2 | 3 | 4 |
| (Z)-endoxifen | 0.1 g | 0.1 g | 0.05 | 0.05 g |
| Solvent | 10 mL 99.5% EtOH | 10 mL 99.5% EtOH | 18 mL 70% EtOH | 18 mL 70% EtOH |
| Concentration | 10 mg/mL | 10 mg/mL | 2.8 mg/mL | 2.8 mg/mL |
| Temperature | 25° C. | 40° C. | 25° C. | 40° C. |
| 2 days E/Z Ratio | 1/71 (1.37%/97.33%) | 1/57 (1.70%/96.98%) | 1/46 (2.09%/96.59%) | 1/21 (4.43%/94.23%) |
| Total Impurity | 13% | 1.32% | 1.33% | 1.34% |
| 7 days E/Z Ratio | 1/50 (1.91%/96.37%) | 1/34 (2.82%/95.45%) | 1/17 (5.62%92.67%) | 1/5.5 (15.23%/83.04%) |
| Total Impurity | 1.72% | 1/73% | 1.71% | 1.73% |
| 10 days E/Z Ratio | 1/37 (2.58%/96.03%) | 1/27 (3.56%/95.10%) | 1/8.4 (10.46%/88.20%) | 1/3.4 (22.59%/76.09%) |
| Total Impurity | 1.39% | 1.34% | 1.34% | 1.32% |

Results show that (Z)-endoxifen free base is surprisingly stable in alcoholic (for example ethanol and isopropanol (data not shown)) solutions even at elevated temperatures (40° C.) at higher concentrations over 10 days. Accelerated stability at higher temperatures are generally considered predictive of long term (at least 18 m) stability at ambient temperatures.

B. Bulk Drug Stability Study (Z)-endoxifen free base of the instant disclosure prepared by methods disclosed herein is surprisingly stable in bulk form. For bulk stability studies, ~1 g aliquots of (Z)-endoxifen free base were placed inside individually in double LDPE bags tied with a nylon cable tie. The LDPE bags were then placed in aluminum foil bags and thermally sealed. The samples for stability were placed in tightly capped, 180 mL HDPE bottles under inert conditions (dry nitrogen) at 5° C. and 25° C./60% RH for 12 months, and at 40° C./75% RH for 3 months. The samples were tested for (E)-endoxifen and (Z)-endoxifen concentrations and impurities, moisture or water content by Karl Fischer titration, aerobic bacterial colony forming units and appearance at time points day 0, 10 days, 1 m and 3 m. Table 13 below provides bulk drug stability data at 9 m on endoxifen free base at varying storage conditions.

TABLE 13

Bulk Drug Stability of (Z)-endoxifen Free Base

| Endoxifen (Free Base) | % Purity Storage (5° C.) | | | | % Purity Storage 25° C./60% RH | | | | % Purity Storage 40° C./75% RH | |
|---|---|---|---|---|---|---|---|---|---|---|
| | 0 m | 3 m | 6 m | 9 m | 0 m | 3 m | 6 m | 9 m | 0 m | 3 m |
| (Z)-endoxifen | 99.5 | 99.6 | 99.5 | 99.5 | 99.5 | 99.6 | 99.5 | 99.5 | 99.5 | 99.5 |
| (E)-endoxifen | 0.19 | 0.17 | 0.18 | 0.19 | 0.19 | 0.17 | 0.18 | 0.19 | 0.19 | 0.17 |

TABLE 13-continued

Bulk Drug Stability of (Z)-endoxifen Free Base

| Endoxifen (Free Base) | % Purity Storage (5° C.) | | | | % Purity Storage 25° C./60% RH | | | | % Purity Storage 40° C./75% RH | |
|---|---|---|---|---|---|---|---|---|---|---|
| | 0 m | 3 m | 6 m | 9 m | 0 m | 3 m | 6 m | 9 m | 0 m | 3 m |
| Water content (Karl Fischer) | 0.06 | 0.05 | 0.05 | 0.05 | 0.06 | 0.05 | 0.06 | 0.07 | 0.06 | 0.07 |
| Max Indiv. Impurity | 0.11 | 0.10 | 0.11 | 0.11 | 0.11 | 0.11 | 0.11 | 0.11 | 0.11 | 0.11 |
| (Z)-endoxifen USP <921≥ Plate Count (cfu g/mL) | 13990 | | | | 14030 | | | | 13776 | |

Results show that solid Z-endoxifen free base is stable for at least 9 months at 5° C. and 25° C./60% RH. Accelerated stability at high temperatures is considered to be predictive of long term (at least 18 m) stability at ambient temperatures. (Z)-to-(E) endoxifen interconversion is minimal at the storage conditions studied, water content was not more than 1% and aerobic bacterial plate count TAC (cfu) is less than 20,000 cfu g/mL. Maximum individual impurities were determined at each time point and ranged from 0.10% to 0.11%.

Example 12: Characteristics of Purified Solid Z-Endoxifen Free Base (Z)-endoxifen free base, produced by methods disclosed herein, was a white to off-white powder. The water content of such a powder was not more than 1% as determined using Method 1c (Karl Fischer titration) of USP 921. The residual solvents were measured. Methanol was not more than (NMT) 3000 ppm, tetrahydrofuran NMT 720 ppm, isopropanol, ethyl acetate, n-heptane, and ethanol were each NMT 5000 ppm.

Residue on ignition of (Z)-endoxifen was not more than 0.1% as determined by Method II of USP 281. Residue on ignition of (Z)-endoxifen ranged from 0.02% to 0.099%. In some embodiments, the residue upon ignition is not more than 0.02%, 0.03%, 0.04%, 0.05%, 0.06%, 0.07%, 0.08%, 0.09%, and 0.1%. In another aspect, the heavy metals were NMT 20 ppm as tested by Method II of USP 231.

Elemental levels in solid (Z)-endoxifen free base is tested using test methods of USP 232 and USP 40.

Thus, the processes described herein and endoxifen prepared using these processes are suitable for manufacture of clinical and commercial grade (Z)-endoxifen.

Figure 2:
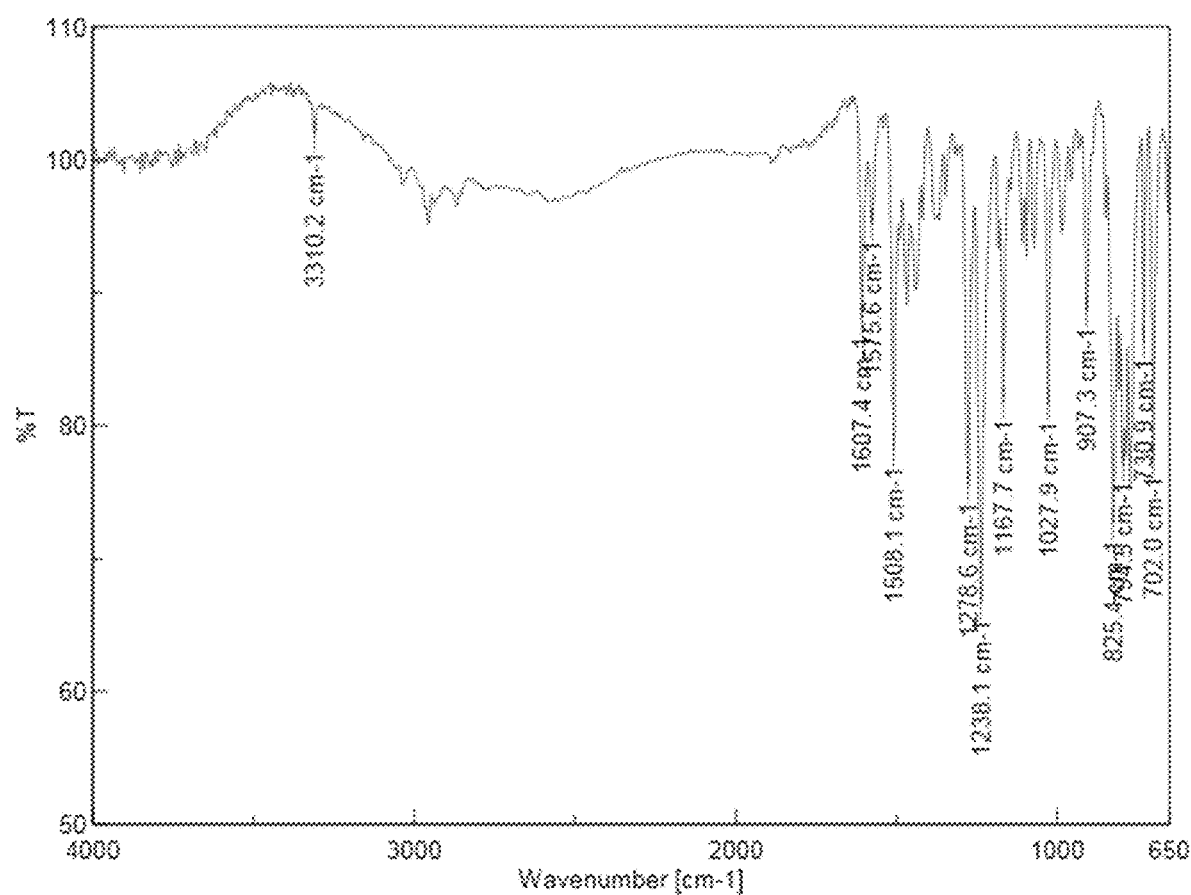
FIG. 2 is a representative infrared spectrum of (Z)-endoxifen free base prepared using methods disclosed herein.

FTIR Spectrum of Z-Endoxifen (Z)-endoxifen was analyzed using Fourier Transform Infra-Red Spectroscopy (Instrument type: FT/IR4600Type A; Jasco: S/N ratio 25,000:1, Max resolution 0.7 cm$^{-1}$) with standard light source and a TGS detector. Infrared spectra were recorded on a FTIR spectrometer (Model FT/IR 4600 Type A; manufacturer Jasco), equipped with triglycine sulfate (TGS) detector and KBr beam splitter, using AgBr windows. About 10 mg of (Z)-Endoxifen free base was placed onto the ATR crystal, pressure was applied with the tip, and the sample spectrum was collected. Spectra were collected with a scan speed to 2 mm/sec using hydrated films. Interferograms were accumulated over the spectral range 4000-650 cm$^{-1}$ with a nominal resolution of 0.4 cm$^{-1}$ and 32 scans. FIG. 2 shows a representative IR Spectrum of (Z)-endoxifen free base.

FIG. 2 shows that purified (Z)-endoxifen has peaks at 702.0, 730.9, 794.5, 825.4, 907.3, 1027.9, 1167.7, 1238.1, 1278.6, 1508.1, 1575.6, 1607.4, 3310.2 wavelengths cm$^{-1}$+/−0.4 cm$^{-1}$. A previously published FT/IR spectrum of free endoxifen showed peaks are at 706, 831, 1053, 1171, 1240, 1465, 1507 and 1604 wavelength cm$^{-1}$ (Agudelo et al. PLoS ONE 8(3): e60250. doi:10.1371/journal.pone.0060250).

TABLE 14

Spectral Assignments for IR spectrum of (Z)-endoxifen free base

| Assignment | Frequency | Strength |
|---|---|---|
| N—H stretching | 3200-3500 | weak |
| O—H stretching | | |
| C=C stretching | 1500 1680 | Medium |
| CH2 & CH3 bending | 1200-1500 | Medium |
| C—N stretching | 1000-1200 | Medium |
| C—O stretching | | |
| =C—H bending | 690-1000 | Medium |
| =CH$_2$ bending | | |

Example 13: Oral Compositions of Z-Endoxifen

API-in-Capsule. ≥90% Z-endoxifen free base was prepared as disclosed above. Dry white-to-off-white powder is formulated as stable free-flowing powder and filled neat into a capsule as a Drug-in-Capsule (DIC, also called API-in-capsule, AIC) oral solid dosage form. 1 mg, 2 mg, and 4 mg of endoxifen which was at least 90% (Z)-endoxifen was filled neat in a VCaps® Plus enteric capsule using Xcellodose technology (Capsugel). AIC were of size 0, Swedish orange in color.

The VCaps® Plus enteric capsules (Capsugel) are made with gluten free, non-animal self-gelling product hypromellose (methyl and hydroxypropyl mixed ether of cellulose), with low-moisture content that is suitable for moisture-sensitive ingredients such as (Z)-endoxifen. The capsules are coated with an enteric coating designed to achieve intestinal targeting (upper GI and colon), by the method of Cole et al. (Cole et al., Int. Journal of Pharmaceutics Vol. 231 83-95, 2002). Eudragit FS D30 is used as enteric coating for colonic targeted release and Eudragit L30 D55 is used as enteric coating for upper gastrointestinal targeted release.

(Z)-endoxifen free base in the AIC is released in predominantly in the intestines (upper GI and colon) and is protected from the acidic environment in the stomach for at least 6 hours. Enteric coating of the capsule prevents the release of (Z)-endoxifen in the stomach for at least 6 hours as tested by a method of USP 711.

Enteric AIC disclosed herein is stable for at least 6 months.

Standards and testing for microbial contamination of the oral solid dosage forms of the instant disclosure. For formulations of the solid dosage compositions disclosed herein, as the water content is NMT 1% and water activity (Aw) is less than 0.75, testing TAC and USP indicator organism is not necessary. The publication, "Microbial Bioburden on Oral Solid Dosage Form," by Jose E. Martinez, Pharmaceutical Technology, February 2002, pages 58 to 70, is hereby incorporated by reference in its entirety.

Furthermore, since formulations of the compositions disclosed herein also have water activity of less than 0.75, then no detailed microbial testing of that need be done. Total Aerobic Plate Count (TAC) is an estimation of the total viable aerobic bacteria present in a sample of raw material, in-process material, or finished product. Samples are analyzed in accordance with the most current USP Guidelines Chapter 61 (Microbial Limits Tests).

Acceptable TAC for oral solid dosage forms (OSDFs) are established for the formulation of the inventive compositions in terms of alert and action levels, which could be 1000 cfu g/ml, and 10,000 cfu g/mL respectively. A TAC that is 20,000 cfu g/mL is considered unacceptable.

Example 14: Preparation of (Z)-Endoxifen Salt (Z)-Endoxifen D-gluconate salt is prepared by mixing an ethanolic slurry of (Z)-endoxifen as the free base with an aqueous solution of D-gluconic acid, followed by hydrolyzing a 20% w/v solution of D-gluconolactone in water and heating at 70° C. for 15 to 30 min. Minimum volume of ethanol is used and 5 ml of the aqueous D-gluconic acid solution is adder per 1 g of endoxifen free base. Stirring is then continued until a clear solution is obtained. (Z)-Endoxifen D-gluconate is crystallized using the methods disclosed above in Examples 1 to 4 to provide (Z)-endoxifen D-gluconate salt.

1 mg, 2 mg, 5 mg, 10 mg, 20 mg and 40 mg AIC enteric capsules will be prepared as described above. Similarly, 1 mg to 50 mg tablets will be prepared using (Z)-endoxifen D-gluconate salt with enteric coatings EUDRAGIT® FS D30 and EUDRAGIT® L30D 55 to target small intestine and colon.

TABLE 15

Exemplary Tablet

| Ingredient | wt/wt of composition |
| --- | --- |
| (Z)-endoxifen D-gluconate | 0.1% to 20% |
| croscarmellose sodium | 0.5% to 15% |
| microcrystalline cellulose | 15% to 90% |
| mannitol | 5% to 30% |
| Enteric coating EUDRAGIT ® L30D 55 | 0.01% to 3% |

Example 15: Placebo Controlled, Dose Escalation Safety and Pharmacokinetic Study of Oral (Z)-Endoxifen An objective of the study was to assess the safety and tolerability of oral (Z)-Endoxifen when administered as a topical application to the breast or orally as a capsule to healthy female volunteers. A secondary objective was to assess the pharmacokinetics of multiple doses of oral (Z)-Endoxifen in the subjects.

Generally, healthy female volunteers aged ≥18 years and ≤65 years were enrolled. 24 participants were enrolled in 3 cohorts and will be administered study drug orally. Three dose levels of orally administered (Z)-Endoxifen were investigated in 3 cohorts. In each cohort participants were randomized to receive an oral (Z)-Endoxifen or placebo in a blinded fashion. Enteric-resistant capsules used in the study were designed as delayed release capsules to resist rupture for at least 30 minutes, but typically, for about 2 hours, under gastric conditions and then open fully in intestinal fluid (DRCaps; Capsugel, a Lonza Company, USA). Enteric-resistant (Swedish Orange size Zero (0); Capsugel, USA) DRCaps capsules manually filled with 1, 2 or 4 mg of (Z)-endoxifen neat in compliance with GMP requirements were used. Placebo capsules contained microcrystalline cellulose an inert common capsule and tablet excipient.

Each cohort enrolled 8 participants, with 6 participants receiving (Z)-Endoxifen 1 mg capsules orally at 1 mg (Cohort 1), 2 mg (Cohort 2) or 4 mg (Cohort 3) doses and 2 participants receiving matching placebo capsules. In Cohort 1 (Dose Level=1 mg) two participants (sentinels) were dosed 24 hours prior to the remaining participants. One sentinel was dosed with (Z)-Endoxifen and the other with placebo. The remaining six participants in Cohort 1 were dosed as no safety concerns were identified in the sentinel participants. The non-sentinel participants in Cohort 1 were admitted to the clinical research facility at least one day later than the sentinels. There were no sentinels in Cohorts 2 and 3.

Participant engagement in this study was for a period of 56 days. These included a 28 day screening period, and a 7 day post treatment period for Pharmacokinetic (PK) sampling. There were two confinement periods, one at the beginning and one at the end of the dosing periods. Participants were confined to the clinical facility on Days −1 through to Day 2 and Days 21 and 22. If participants were to experience any clinically significant adverse events during the study, they would have been required to remain in the clinical facility for further observation at the discretion of the Principal Investigator (PI).

Healthy female volunteers were screened within 28 days prior to commencement of dosing. Participants were admitted to the clinical facility on Day −1 for up to 3 days. The first dose of (Z)-Endoxifen or placebo capsules was administered on Day 1. Following completion of all safety assessments and sampling for PK analyses, participants were discharged from the clinical facility on Day 2. The first dose on Day 1 was followed by a 6-day treatment free period (Days 2-7). Each participant returned to the clinical facility for PK blood draws and safety assessments during the treatment free period on study Days 4 and 6. On Day 8 participants commenced daily administration of (Z)-Endoxifen capsules or placebo capsules for 14 consecutive days (Days 8-21). Participants were supplied with study drug capsules and asked to self administer daily. Participants visited the clinical facility on Days 11, 14 and 17, prior to dose administration, for PK blood draws and safety assessments. On the morning of Day 21 each participant returned to the clinical facility prior to dose administration and were confined to the facility until Day 22 to allow for the collection of PK blood draws and safety assessments. The Day 21 dose was the last administration of study drug. Participants were discharged from the clinical facility on Day 22 and returned for PK blood draws and safety assessments on study Days 24, 26, and 28.

Study assessments included taking the subjects medical history, including evaluation of any on-study adverse events and concomitant medication use; height and weight; physical examination; periodic vital signs (body temperature, heart rate, respiratory rate, blood pressure); periodic 12-lead ECGs. Laboratory tests included hematology, coagulation, urinalysis, serum chemistry and biomarker analysis (e.g., CYP2D6, BRCA1/2, Ki67, tamoxifen metabolites, etc.). Specific assessments to evaluate treatment safety included the following: the frequency and type of adverse events, clinical laboratory testing, 12-lead ECGs and vital signs. A modified FACT-ES® scoring questionnaire was used to assess symptomatology.

Blood draws for PK analysis were collected pre-dose (within 10 min) and 0.5, 1, 2, 3, 4, 6, 8, 10, 12 and 24 hours following study drug administration on Days 1 and 21. PK samples for all other study days were collected within 10 min prior to dose administration. PK samples were obtained during the treatment free period on Days 4 and 6. Additional, PK samples were collected during the daily dosing period on Days 8, 11, 14 and 17 (within 10 min pre-dose). PK samples following completion of treatment will be collected on Days 24, 26 and 28. AUC(inf) was measured on Day 1 blood draw samples. Steady state plasma levels were determined starting from Day 8 onwards (which served as Day 0) for this determination.

Safety and Tolerability

Safety endpoints were summarized by dose cohort, with placebos pooled across cohorts. Treatment-emergent AEs were coded using the latest version of MedDRA by System Organ Class (SOC) and Preferred Term, classified from verbatim terms. The incidence and frequency of AEs, and SAEs, were summarized by cohort according to SOC and Preferred Terms, and by severity and relationship. The duration of AEs was determined and included in listings, along with the action taken and outcome. Vital signs, ECG and safety laboratory parameters were summarized at each scheduled time point using descriptive statistics. Post-dose assessments were compared with baseline measurements. The incidence of laboratory abnormalities was summarized. Physical examination findings were presented in listings.

Treatment-emergent AEs deemed to be related to study drug (probably or possibly) were reported in 15 of 18 subjects (83%, 41 AEs) who received (Z)-Endoxifen and in 4 of 6 subjects (67%, 20 AEs) who received placebo. Most treatment-related AEs were mild in severity, with treatment related AEs of moderate severity reported in 5 of 18 subjects (28%, 6 AEs) who received (Z)-Endoxifen and in 2 of 6 subjects (33%, 2 AEs) who received placebo.

All AEs were classified as mild (75 of 84 AEs) or moderate (9 of 84 AEs) in severity, with no AEs classified as severe. Common adverse events of tension headache, headache, abdominal pain, nausea, dysmenorrhea and fatigue were reported both in subjects who received oral (Z)-Endoxifen and subjects who received placebo. Upper respiratory infection, hot flush, abdominal distension, dry mouth, and menstruation delayed were reported only in subjects who received (Z)-Endoxifen.

There were no clear differences in safety as assessed by clinical laboratory tests, vital signs, ECG assessments, FACT-ES responses in subjects who had received either topical or oral (Z)-Endoxifen compared with those who received placebo, and no dose-related trends in these safety assessments in those subjects who received (Z)-Endoxifen.

Pharmacokinetics

Mean and individual (Z)-Endoxifen serum concentration-time curves were tabulated for each dose cohort, and presented graphically with concentration displayed on a linear and logarithmic scale. Pharmacokinetic parameters were determined for each participant and summarized by cohort using descriptive statistics (arithmetic means, standard deviations, coefficients of variation, sample size, minimum, maximum and median). In addition, geometric means was calculated for AUC and Cmax. Analyses using linear models was performed to assess dose proportionality (both after a single dose and multiple dose), time dependence and accumulation (oral multiple dose), and attainment of steady state (multiple dose).

Parameters determined for the first and last dose (Days 1 and 21) included time to maximum concentration (Tmax), maximum concentration (Cmax), area under the concentration-time curve from time 0 to 24 hours following drug administration ($AUC_{0-24h}$), terminal elimination rate constant (kel), terminal half-life ($t_{1/2}$), terminal clearance (CL/F) and volume of distribution (Vd/F). Area under the concentration-time curve from time 0 to infinity ($AUC_{0-inf}$) was also determined for the first dose, on Day 1.

The pharmacokinetic parameters were determined using non-compartmental method(s). Descriptive statistics of pharmacokinetic parameters included mean, standard deviation (SD), and coefficient of variation (CV), minimum (min) and maximum (max). Dose related trends in pharmacokinetic parameters were assessed.

Mean and individual endoxifen serum concentration-time curves were tabulated for each dose cohort. Pharmacokinetic parameters, were determined for each participant and summarized by cohort using descriptive statistics (arithmetic means, SD, CV, sample size [N], min, max and median). In addition, geometric means were calculated for AUC and Cmax. Analyses using linear models were performed to assess dose proportionality (both after a single dose (oral) and multiple dose (topical and oral)). Statistical analysis was performed on the pharmacokinetic parameters using SAS v9.3 and Phoenix WinNonLin version 7.0 or higher.

Abbreviations used:

CV Coefficient of Variance

Tmax time to maximum concentration

Cmax maximum concentration, $AUC_{0-24h}$ ("AUC24 hr") area under the concentration-time curve from time 0 to 24 hours following drug administration kel terminal elimination rate constant, and volume of t1/2 terminal half-life CL/F terminal clearance Vd/F distribution.

$AUC_{0-inf}$ ("$AUC_{0-inf}$") Area under the concentration-time curve from time 0 to infinity was also determined for the first dose, on Day 1.

A summary of serum pharmacokinetic parameters with terminal half-life of (Z)-endoxifen, terminal elimination half-life, Tmax, Cmax, and AUC are provided below in Table 16.

TABLE 16

Model Serum Pharmacokinetic Parameters

| Day | (Z)-Endoxifen Dose/Day (mg) | Median (Range) $T_{max}$ (hr) | Arithmetic Mean (CV %) | | |
|---|---|---|---|---|---|
| | | | $C_{max}$ (ng/mL) | $AUC_{24\,hr}$ (hr*ng/mL) | $t_{1/2}$ (hr) |
| Day 1 | 1 mg (n = 5) | 6.0 (2.0-8.08) | 9.6 (18.9%) | 158 (20.3%) | 41.1 (15.8%) |
| | 2 mg (n = 6) | 4.17 (3.0-6.0) | 17.7 (23.4%) | 305 (17.9%) | 49.0 (26.0%) |
| | 4 mg (n = 6) | 5.08 (3.0-6.0) | 32.5 (52.3%) | 587 (53.3%) | 41.6 (22.9%) |
| Day 21 | 1 mg (n = 5) | 8.0 (4.0-6.05) | 24.6 (35.0%) | 458 (36.3%) | 52.6 (20.8%) |
| | 2 mg (n = 6) | 4.0 (2.0-6.05) | 50.0 (23.7%) | 911 (19.7%) | 43.4 (17.1%) |
| | 4 mg (n = 6) | 5.0 (2.0-10.0) | 115.0 (49.0%) | 2041 (50.4%) | 45.1 (15.2%) |

For once daily oral administration of the delayed-release (acid-resistant) (Z)-endoxifen capsules, there was dose-proportionality (linear dose response) in Cmax and $AUC_{24hr}$ of endoxifen across the three dose levels used in the study.

Figure 4:
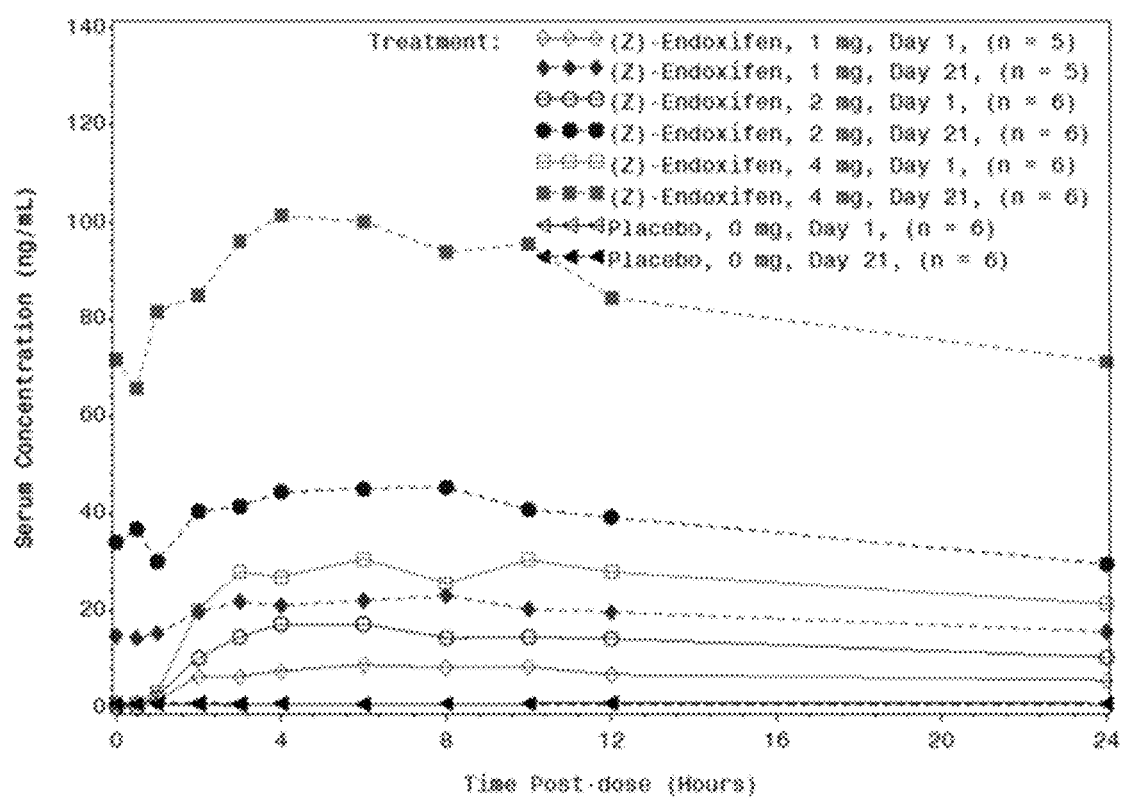
FIG. 4 shows the time to maximum serum levels of endoxifen following treatment with placebo or 1 mg, 2 mg or 4 mg endoxifen capsules at day 1 and day 21. The time post-dose (hours) is plotted on the X-axis and mean serum concentration (ng/mL) is plotted on the Y-axis.
Figure 5:
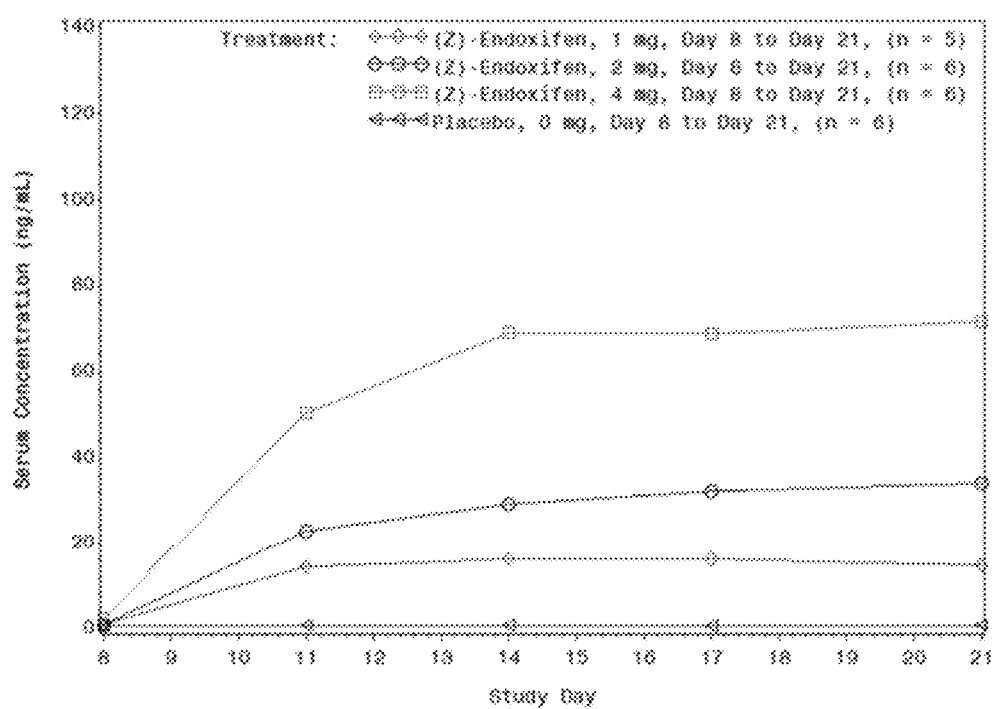
FIG. 5 shows the time to achieve steady state serum levels of endoxifen following treatment with placebo or 1 mg, 2 mg or 4 mg endoxifen capsules from day 0 (day 0 refers to day 8 on the X-axis) to day 21. The X-axis is time in days (Day 8 to Day 21) and the Y-axis is mean serum concentration in ng/mL. Blood was drawn on each day from day 0 to the end of the clinical trial period. Subjects were dosed on day 1 and plasma endoxifen levels were measured as shown in Table 17. Subjects were subsequently dosed daily starting on day 8 (labeled day 8 in FIG. 5) until the end of study period.
Figure 6:
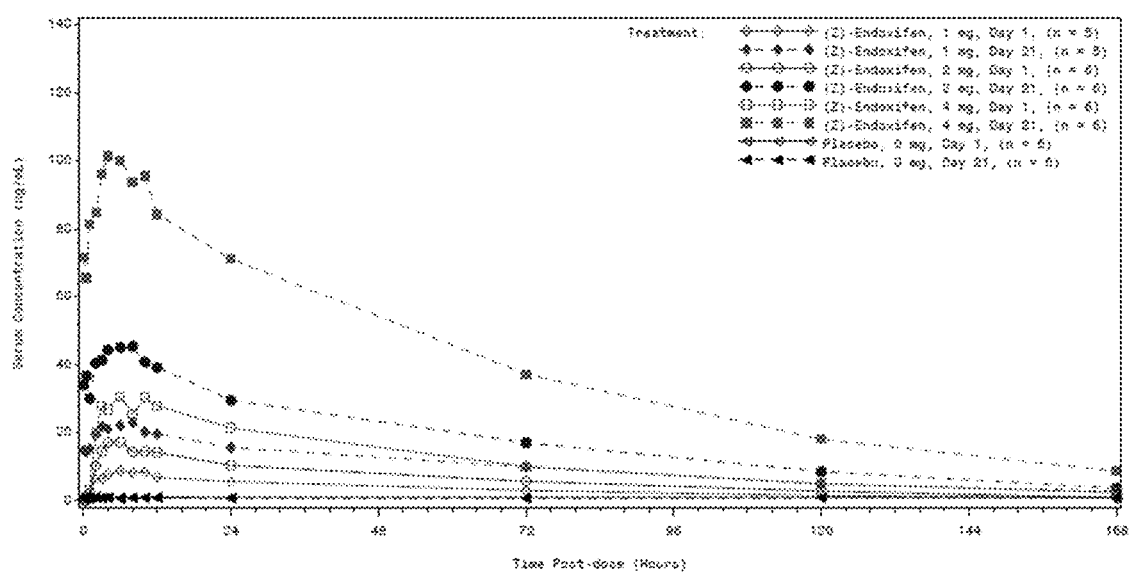
FIG. 6 shows mean serum concentrations (ng/mL) over time following treatment with placebo or 1 mg, 2 mg or 4 mg endoxifen capsules at day 1 and day 21 (Linear).
Figure 7:
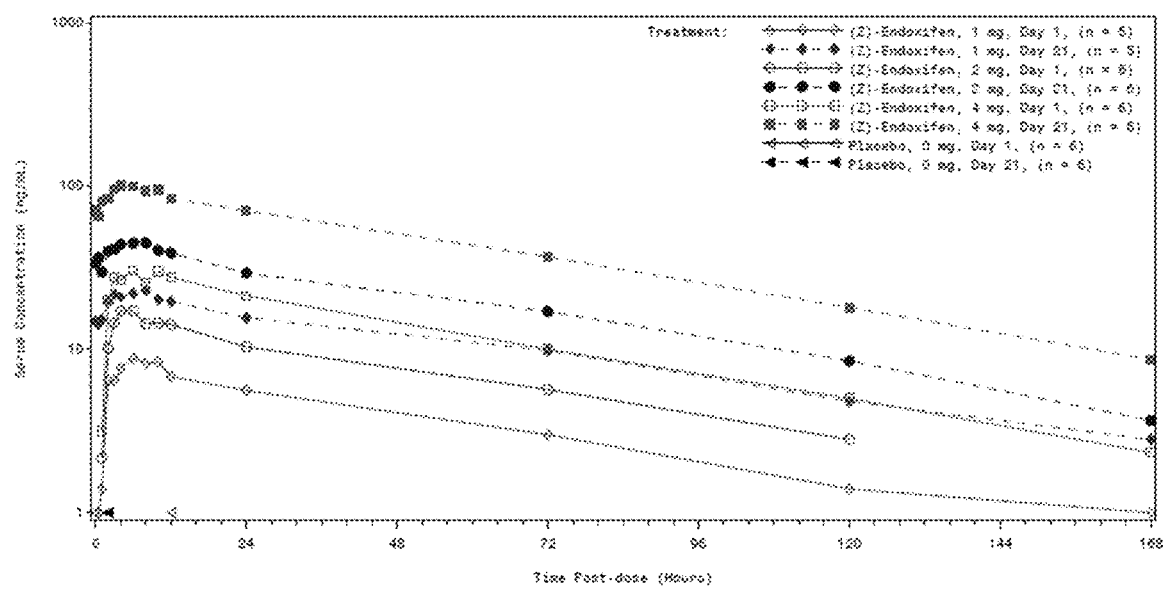
FIG. 7 shows mean serum concentrations (ng/mL) over time following treatment with placebo or 1 mg, 2 mg or 4 mg endoxifen capsules at day 1 and day 21 (Semi-log).
Figure 8:
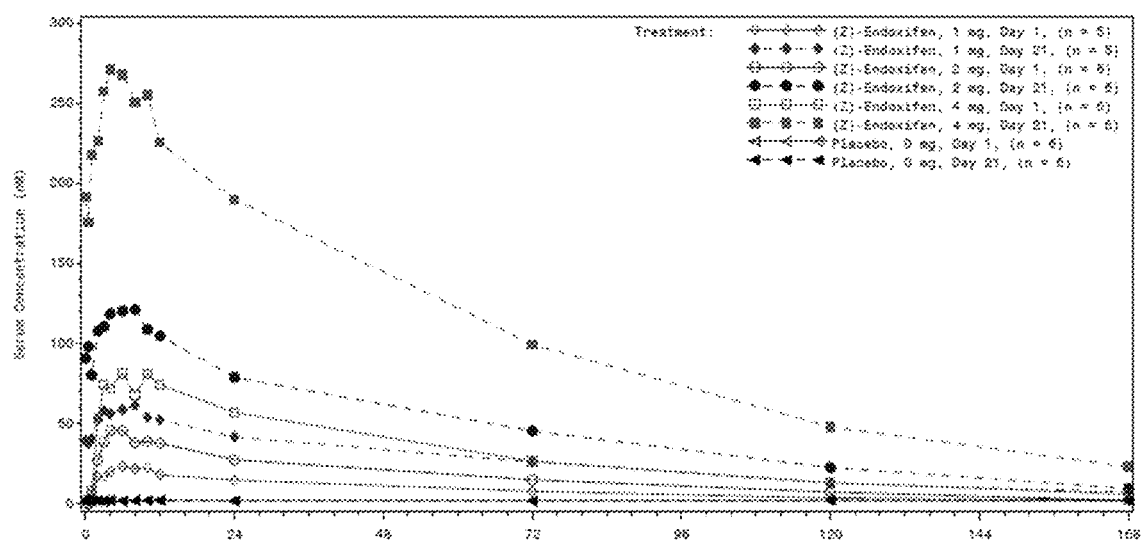
FIG. 8 shows mean serum concentrations (nM) over time following treatment with placebo or 1 mg, 2 mg or 4 mg endoxifen capsules at day 1 and day 21 (Linear).

Cmax increased from 9.6 ng/mL to 32.5 ng/mL for the 1 mg to 4 mg doses on day 1 and from 24.6 ng/mL to 115.0 ng/mL on Day 21. Median Tmax by dose level on Days 1 and 21 ranged from 4 to 8 hours. The apparent terminal half life ($t_{1/2}$) by dose level ranged between 42 and 53 hours, and steady state appeared to be attained after approximately 7 days (FIG. 5—dosing at Day 8 and Css at Day 14). Time to reach maximum blood levels ranged from 4 to 8 hours (FIG. 4).

TABLE 17

Model $AUC_{(0-inf)}$: 1 mg. 2 mg, and 4 mg (Z)-endoxifen
$AUC_{(0-inf)}$ hr* ng/mL

| Dose: 1 mg | Dose: 2 mg | Dose: 4 mg |
|---|---|---|
| 441 | 755 | 736 |
| 534 | 954 | 1883 |
| 739 | 1242 | 2116 |
| 527 | 1489 | 4624 |
| 593 | 1009 | 1098 |
| | 1188 | 1642 |

TABLE 18A

Model Serum Concentrations (nM) Over Time by Treatment, Dose: 1 mg (Z)-Endoxifen

| Statistic | Pre-dose | hr 0.5 | hr 1 | hr 2 | hr 3 | hr 4 | hr 5 | hr 8 | hr 10 | hr 12 | hr 24 | Day 4 Hr 72 | Day 6 Hr 120 | Day 8 Pre-dose | Day 11 Pre-Dose | Day 14 Pre-dose | Day 17 Pre-Dose |
|---|---|---|---|---|---|---|---|---|---|---|---|---|---|---|---|---|---|
| | | | | | Day 1 | | | | | | | | | | | | |
| Mean | 2.68 | 2.68 | 3.75 | 17.1 | 17.1 | 20.3 | 23.6 | 22.0 | 22.5 | 18.2 | 15.0 | 8.03 | 3.75 | 2.68 | 38.5 | 43.4 | 43.4 |
| Std Dev | 0.0 | 1.89 | 2.39 | 2.4 | 1.5 | 3.6 | 4.4 | 6.9 | 6.7 | 5.8 | 3.1 | 1.89 | 1.47 | 0.00 | 8.6 | 22.8 | 19.1 |
| CV (%) | 0 | 71 | 64 | 14 | 9 | 18 | 19 | 32 | 30 | 32 | 20 | 24 | 39 | 0 | 22 | 53 | 44 |
| Median | 2.68 | 2.68 | 2.68 | 18.7 | 16.1 | 18.7 | 24.1 | 21.4 | 21.4 | 21.4 | 16.1 | 8.03 | 2.68 | 2.68 | 42.8 | 40.2 | 45.5 |
| Min | 2.68 | 0.00 | 2.68 | 13.4 | 16.1 | 18.7 | 16.1 | 13.4 | 13.4 | 8.03 | 10.7 | 5.35 | 2.68 | 2.68 | 26.8 | 13.4 | 13.4 |
| Max | 2.68 | 5.35 | 8.03 | 18.7 | 18.7 | 26.8 | 26.8 | 32.1 | 32.1 | 21.4 | 18.7 | 10.7 | 5.35 | 2.68 | 45.5 | 75.0 | 64.2 |
| GeoMean | 2.68 | 3.18 | 3.33 | 17.0 | 17.1 | 20.1 | 23.2 | 21.1 | 21.6 | 17.1 | 14.7 | 7.84 | 3.53 | 2.68 | 37.7 | 37.6 | 38.5 |

TABLE 18B

Model Pharmacokinetic Parameters by Treatment; Dose 2 mg (Z)-Endoxifen (n = 6).

| Mean | 0.17 | 0.00 | 2.17 | 10.2 | 14.5 | 17.2 | 17.2 | 14.3 | 14.5 | 14.2 | 10.3 | 5.67 | 2.80 | 0.83 | 22.8 | 29.2 | 32.2 |
|---|---|---|---|---|---|---|---|---|---|---|---|---|---|---|---|---|---|
| Std Dev | 0.41 | 0.00 | 1.47 | 3.8 | 2.3 | 4.8 | 3.7 | 3.8 | 3.4 | 2.0 | 2.3 | 1.53 | 1.10 | 0.43 | 3.3 | 4.7 | 7.7 |
| CV (%) | 245% | 0% | 58% | 37% | 16% | 28% | 23% | 26% | 23% | 34% | 22% | 29% | 39% | 49% | 15% | 16% | 24% |
| Median | 0.00 | 0.00 | 2.50 | 10.0 | 14.5 | 17.5 | 17.0 | 14.5 | 14.5 | 14.0 | 10.5 | 5.50 | 3.00 | 1.00 | 22.5 | 28.5 | 29.5 |
| Minimum | 0.00 | 0.00 | 0.00 | 5.00 | 11.0 | 11.0 | 13.0 | 8.00 | 10.0 | 12.0 | 8.0 | 4.00 | 1.00 | 6.00 | 19.0 | 23.0 | 27.0 |
| Maximum | 1.00 | 0.00 | 4.00 | 16.0 | 17.0 | 22.9 | 22.0 | 19.0 | 19.0 | 18.0 | 10.0 | 8.00 | 4.00 | 1.00 | 28.0 | 37.0 | 47.0 |
| GeoMean | 1.00 | | 2.35 | 8.55 | 14.3 | 16.6 | 16.8 | 13.8 | 14.2 | 14.1 | 10.1 | 5.47 | 2.55 | 1.00 | 22.5 | 28.9 | 31.5 |

TABLE 18C

Model Pharmacokinetic Parameters by Treatment; Dose 4 mg (Z)-Endoxifen (n = 6)

| N | 6 | 6 | 6 | 6 | 6 | 6 | 6 | 6 | 6 | 6 | 6 | 6 | 6 | 6 | 6 | 6 | 6 |
|---|---|---|---|---|---|---|---|---|---|---|---|---|---|---|---|---|---|
| Mean | 0.83 | 0.83 | 3.17 | 20.0 | 27.8 | 26.8 | 30.5 | 25.5 | 30.3 | 27.8 | 21.3 | 10.0 | 5.50 | 2.33 | 50.4 | 69.0 | 88.8 |
| Std Dev | 0.41 | 0.41 | 1.72 | 5.0 | 13.7 | 12.1 | 18.0 | 11.0 | 17.8 | 14.9 | 13.2 | 6.8 | 4.54 | 1.97 | 25.3 | 45.8 | 43.0 |
| CV (%) | 49% | 49% | 54% | 40% | 49% | 45% | 59% | 43% | 59% | 53% | 52% | 68% | 93% | 84% | 50% | 86% | 62% |
| Median | 1.00 | 1.00 | 4.00 | 19.0 | 24.5 | 24.0 | 25.5 | 25.0 | 28.0 | 25.5 | 19.5 | 8.00 | 4.00 | 3.50 | 45.0 | 64.0 | 73.0 |
| Minimum | 0.00 | 0.00 | 1.00 | 11.9 | 14.0 | 14.0 | 14.0 | 13.0 | 18.0 | 11.0 | 8.00 | 4.00 | 3.00 | 1.00 | 33.0 | 3.00 | 1.00 |
| Maximum | 1.00 | 1.00 | 5.00 | 35.0 | 52.0 | 49.0 | 62.0 | 42.0 | 62.0 | 52.0 | 43.0 | 23.0 | 10.0 | 6.00 | 77.0 | 145 | 115 |
| GeoMean | 1.00 | 1.00 | 2.52 | 38.9 | 25.3 | 24.8 | 26.7 | 23.5 | 35.4 | 24.6 | 18.0 | 8.54 | 3.82 | 1.92 | 45.2 | 44.9 | 37.5 |

TABLE 19A

Day 1 Model Pharmacokinetic Parameters by Treatment; Dose 1 mg (Z)-Endoxifen. N = 5

| Statistic | Cmax (ng/mL) | Tmax (hr) | AUClast (hr*ng/mL) | Kel (l/hr) | Thalf (hr) | $AUC_{0\text{-}inf}$ (hr*ng/mL) | AUC24 hr (hr*ng/mL) | CL/F (L/hr) | Vz/F (L) |
|---|---|---|---|---|---|---|---|---|---|
| Mean | 9.6 | 5.62 | 471 | 0.015 | 46.1 | 567 | 158 | 1.82 | 119.9 |
| Std Dev | 1.8 | 2.21 | 76 | 0.002 | 7.3 | 110 | 32 | 0.33 | 27.4 |
| CV (%) | 18.9 | 39.4 | 16.2 | 16.2 | 15.8 | 19.10 | 20.8 | 18.4 | 22.9 |
| Median | 10.0 | 6.0 | 472 | 0.015 | 47.2 | 534 | 171 | 1.87 | 107.6 |
| Min | 7.0 | 2.0 | 367 | 0.013 | 37.5 | 441 | 102 | 1.35 | 102.7 |
| Max | 12.0 | 8.08 | 582 | 0.018 | 54.4 | 739 | 183 | 2.27 | 168.4 |
| GeoMean | 9.5 | 5.11 | 466 | 0.015 | 45.6 | 559 | 155 | 1.79 | 117.8 |
| GeoCV % | 19.9 | 58.2 | 16.5 | 16.2 | 16.2 | 19.1 | 24.0 | 19.1 | 20.6 |

TABLE 19B

Day1 Model Pharmacokinetic Parameters by Treatment; Dose 2 mg

| | | | | | | | | | |
|---|---|---|---|---|---|---|---|---|---|
| N | 6 | 6 | 6 | 5 | 6 | 6 | 6 | 6 | 6 |
| Mean | 17.7 | 4.28 | 889 | 0.015 | 49.0 | 1105 | 385 | 1.89 | 130.5 |
| Std. Dev | 4.1 | 0.96 | 225 | 0.003 | 12.7 | 256 | 55 | 0.46 | 34.9 |
| CV (%) | 23.4 | 22.5 | 25.3 | 23.3 | 26.0 | 23.3 | 17.9 | 24.1 | 25.7 |
| Median | 17.5 | 4.17 | 955 | 0.015 | 44.0 | 1099 | 303 | 1.83 | 118.0 |
| Minimum | 13.0 | 3.00 | 537 | 0.010 | 37.8 | 755 | 248 | 1.34 | 98.2 |
| Maximum | 22.2 | 6.00 | 1137 | 0.018 | 59.1 | 1499 | 393 | 2.55 | 194.5 |
| GeoMean | 17.3 | 4.19 | 862 | 0.015 | 47.7 | 1081 | 301 | 1.85 | 127.3 |
| GeoCV % | 24.1 | 22.2 | 28.7 | 25.3 | 25.3 | 24.0 | 18.0 | 24.0 | 24.7 |

TABLE 19C

Day 1 Model Pharmacokinetic Parameters by Treatment; Dose 4 mg

| | | | | | | | | | |
|---|---|---|---|---|---|---|---|---|---|
| N | 6 | 6 | 6 | 6 | 6 | 6 | 6 | 6 | 6 |
| Mean | 32.5 | 5.56 | 1654 | 0.017 | 41.6 | 2017 | 587 | 2.73 | 154.5 |
| Std. Dev | 17.0 | 2.47 | 1047 | 0.004 | 9.5 | 1375 | 313 | 1.60 | 79.9 |
| CV (%) | 52.3 | 44.5 | 63.3 | 21.8 | 22.9 | 58.2 | 53.3 | 58.5 | 51.7 |
| Median | 29.5 | 5.08 | 1423 | 0.017 | 39.9 | 1763 | 539 | 2.28 | 130.7 |
| Minimum | 14.0 | 3.00 | 691 | 0.012 | 31.6 | 736 | 258 | 0.87 | 69.9 |
| Maximum | 62.0 | 10.00 | 2574 | 0.022 | 56.0 | 4524 | 1116 | 5.43 | 259.4 |
| GeoMean | 29.1 | 5.15 | 1424 | 0.017 | 40.7 | 1704 | 521 | 2.35 | 137.8 |
| GeoCV % | 55.7 | 43.6 | 64.4 | 22.8 | 22.8 | 59.1 | 57.8 | 59.1 | 56.5 |

TABLE 19D

Day 21 Model Pharmacokinetic Parameters by Treatment; Dose 1 mg (Z)-Endoxifen. N = 5

| | | | | | | | | |
|---|---|---|---|---|---|---|---|---|
| N | 5 | 5 | 5 | 5 | 5 | 5 | 5 | 5 |
| Mean | 24.6 | 6.98 | 458 | 19.1 | 0.014 | 52.6 | 2.49 | 181.3 |
| Std. Dev | 8.6 | 1.87 | 166 | 6.9 | 0.003 | 10.9 | 1.06 | 64.1 |
| CV (%) | 35.0 | 27.1 | 38.3 | 36.3 | 20.4 | 20.8 | 42.6 | 35.4 |
| Median | 29.0 | 8.00 | 527 | 22.0 | 0.014 | 49.3 | 1.90 | 170.1 |
| Minimum | 14.0 | 4.00 | 248 | 10.3 | 0.011 | 40.6 | 1.57 | 116.7 |
| Maximum | 34.0 | 8.42 | 635 | 26.5 | 0.017 | 65.8 | 4.03 | 286.8 |
| GeoMean | 23.3 | 6.64 | 431 | 17.9 | 0.013 | 51.7 | 2.32 | 173.3 |
| GeoCV % | 40.1 | 32.1 | 42.2 | 42.2 | 20.9 | 20.9 | 42.2 | 33.9 |

TABLE 19E

Day 21 Model Pharmacokinetic Parameters by Treatment; Dose 2 mg (Z)-Endoxifen.

| | | | | | | | | |
|---|---|---|---|---|---|---|---|---|
| N | 6 | 6 | 6 | 6 | 6 | 6 | 6 | 6 |
| Mean | 50.0 | 4.01 | 911 | 38.0 | 0.016 | 43.4 | 2.27 | 139.1 |
| Std Dev | 11.9 | 1.80 | 179 | 7.5 | 0.003 | 7.4 | 0.44 | 22.7 |
| CV (%) | 23.7 | 44.9 | 19.7 | 19.7 | 18.9 | 17.1 | 19.4 | 16.3 |
| Median | 51.0 | 4.00 | 910 | 37.9 | 0.015 | 45.7 | 2.21 | 131.5 |
| Minimum | 35.0 | 2.00 | 716 | 29.8 | 0.014 | 33.0 | 1.70 | 119.6 |
| Maximum | 65.0 | 6.05 | 1177 | 49.1 | 0.021 | 50.8 | 2.79 | 179.4 |
| GeoMean | 48.8 | 3.64 | 897 | 37.4 | 0.016 | 42.8 | 2.23 | 197.7 |
| GeoCV % | 24.9 | 53.1 | 19.8 | 19.8 | 18.2 | 18.2 | 19.8 | 15.5 |

TABLE 19F

Day 21 Model Pharmacokinetic Parameters by Treatment; Dose 4 mg (Z)-Endoxifen.

| | | | | | | | | |
|---|---|---|---|---|---|---|---|---|
| N | 6 | 6 | 6 | 6 | 6 | 6 | 6 | 6 |
| Mean | 115.0 | 5.33 | 2041 | 85.1 | 0.016 | 45.1 | 2.83 | 189.0 |
| Std Dev | 56.3 | 2.73 | 1029 | 42.9 | 0.003 | 6.8 | 2.15 | 156.0 |
| CV (%) | 49.0 | 51.2 | 50.4 | 50.4 | 16.6 | 15.2 | 76.0 | 82.5 |
| Median | 131.0 | 5.00 | 2469 | 102.9 | 0.015 | 45.3 | 1.63 | 106.1 |
| Minimum | 42.0 | 2.00 | 616 | 25.7 | 0.013 | 34.0 | 1.32 | 73.0 |

TABLE 19F-continued

Day 21 Model Pharmacokinetic Parameters by Treatment; Dose 4 mg (Z)-Endoxifen.

| Maximum | 178.0 | 10.00 | 3024 | 126.4 | 0.020 | 54.3 | 6.49 | 461.5 |
|---|---|---|---|---|---|---|---|---|
| GeoMean | 100.5 | 4.75 | 1744 | 72.7 | 0.016 | 44.6 | 2.29 | 147.7 |
| GeoCV % | 67.4 | 58.5 | 76.1 | 76.1 | 15.9 | 15.9 | 76.1 | 84.6 |

TABLE 20

Mean Ratios of Pharmacokinetic Parameters (Day21)/(Day1)

| (Z)-Endoxifen Dose | $C_{max}$(Day 21)/ $C_{max}$(Day 1) | $AUC_{24\ hr}$(Day 21)/ $AUC_{24\ hr}$(Day 1) | $AUC_{24\ hr}$(Day 21)/ $AUC_{0\text{-}inf}$(Day 1) |
|---|---|---|---|
| 1 mg (n = 5) | 2.74 (SD 1.29) | 3.09 (SD 1.49) | 0.81 (SD 0.20) |
| 2 mg (n = 6) | 2.92 (SD 0.88) | 3.04 (SD 0.79) | 0.85 (SD 0.20) |
| 4 mg (n = 6) | 3.56 (SD 1.01) | 3.47 (SD 1.08) | 1.08 (SD 0.38) |

The mean accumulation ratios ranged from 2.74 to 3.56 for Cmax and from 3.04 to 3.47 for $AUC_{24hr}$ as the ratio of parameters on Day 21 compared with Day 1. There was no marked trend by dose level in clearance (Cl/F) and volume of distribution (Vd/F) for Day 1 and Day 21.

Figure 3:
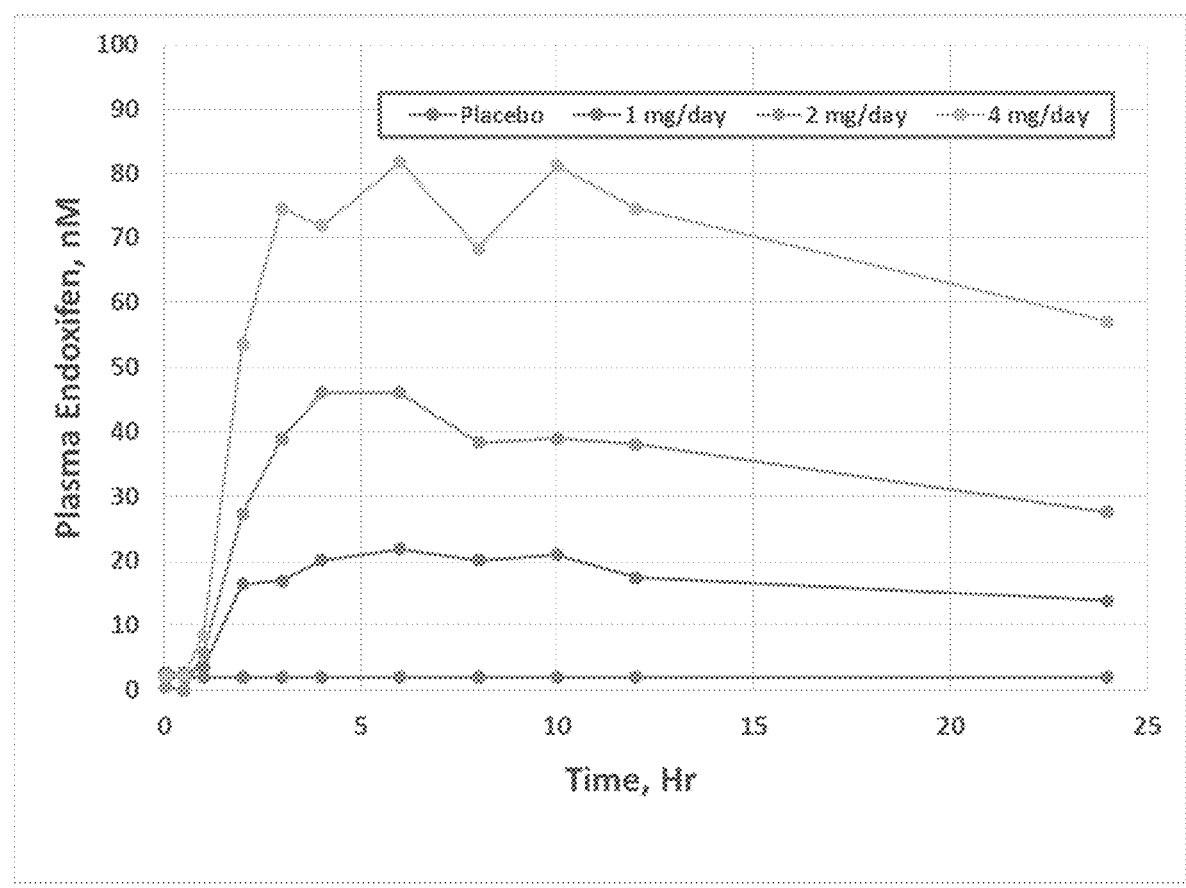
FIG. 3 shows the time to maximum serum levels (nM) of endoxifen following treatment with placebo or 1 mg, 2 mg or 4 mg endoxifen capsules.

Time to maximum serum endoxifen levels is achieved by about 10 hours and that there is dose-related increase in serum endoxifen levels (FIG. 3 and FIG. 4). Serum endoxifen levels ranged from about 25 nM to about 80 nM.

Pharmacokinetic assessment of pre-dose trough concentration from Day 8 to Day 21 (FIG. 4) showed attainment of straight line after day 14. Steady state levels of serum endoxifen appear to be being achieved by Day 7 with daily dosing. The pre-dose serum concentrations indicate little accumulation after 17 days for 4 mg of (Z)-Endoxifen.

TABLE 21

Parameter estimates of dose linearity for endoxifen

| Pharmacokinetic Parameter (log) | Analyte | Day | β Estimate | Two-sided 95% Confidence Interval | $r^2$ |
|---|---|---|---|---|---|
| Cmax | Endoxifen | 1 | 0.808 | (0.487-1.130) | 0.66 |
| | | 21 | 1.055 | (0.655-1.455) | 0.68 |
| $AUC_{24\ hr}$ | Endoxifen | 1 | 0.873 | (0.548-1.199) | 0.69 |
| | | 21 | 1.008 | (0.582-1.433) | 0.63 |

TABLE 22

Comparison of (Z)-endoxifen concentrations (Oral) with published literature.

| (Z)-Endoxifen | Published Literature Result of Average Plasma (Z)-Endoxifen Css | | Study Result of Average Serum (Z)-Endoxifen Css | | % Ratio of Css Study/ |
|---|---|---|---|---|---|
| Dose | ng/mL | nM | ng/mL | nM | Literature |
| 1 mg | 12.4 | 33.1 | 19.1 | 51.1 | 154% |
| 2 mg | 18.6 | 49.8 | 38 | 101.7 | 204% |
| 4 mg | 56.8 | 152.1 | 85.1 | 227.9 | 150% |
| 8 mg | 96.8 | 259.2 | — | — | — |

Css = Average Concentration at Steady State (AUCtau/tau)

Published Literature
1. Wu X et al. Cancer Res. 2009 Mar. 1; 69(5):1722-7. PubMed PMID: 19244106
2. Ahmad A et al. Breast Cancer Res Treat. 2010 July; 122(2):579-84. PubMed PMID:20052538
3. Ahmad A et al. J Clin Oncol 30, 2012 (suppl; abstr 3089)
4. Goetz M P et al. San Antonio Breast Conference 2013 [PD3-4]
5. Goetz M P et al. San Antonio Breast Conference 2015. [PD203]
6. Ahmad A et al. Clin Transl Sci. 2016 Jun. 27. doi: 10.1111/cts.12407. PubMed PMID: 27346789
7. Lee O et al. Cancer Chemother Pharmacol. 2015 December; 76(6):1235-46

Thus, data from this study suggest that safety and tolerability of oral endoxifen is generally comparable to oral tamoxifen and that subjects administered with (Z)-endoxifen compositions have plasma endoxifen levels that are within the range that has been shown to have therapeutic effect in the adjuvant setting in women with breast cancer. (Z)-Endoxifen is rapidly absorbed and systemically available and that it displays dose proportionality in peak drug concentrations in serum (C(max)) and area under the concentration-time curve extrapolated from 0 to infinity ($AUC_{0\text{-}inf}$) over the dose range 1 mg-4.0 mg.

Example 16: Therapeutic Treatment of Tamoxifen-Refractory Breast Cancer by Oral Administration of Z-Endoxifen Free Base An objective of the study is to demonstrate that stable and therapeutic (Z)-endoxifen levels can be achieved in tamoxifen-refractory patients by supplementing tamoxifen with (Z)-endoxifen. Plasma endoxifen levels will be used as a surrogate endpoint to predict clinical benefit as well as the rate of recurrence in this population and to confirm the safety and tolerability of (Z)-endoxifen administration when compared with tamoxifen.

Generally healthy subjects with early stage estrogen receptor positive breast cancer who are on adjuvant therapy of tamoxifen for at least 30 days will be enrolled for the study for up to 6 months. At least seventy-five tamoxifen-refractory breast cancer subjects will be enrolled in the study to ensure an evaluable population consists of at least 25 tamoxifen and 25 (Z)-endoxifen subjects is achieved. Additional subjects may be enrolled to achieve the desired population of tamoxifen-refractory subjects. These subjects will have been diagnosed with breast cancer and undergone mastectomy or lumpectomy.

After at least 30 days of oral tamoxifen, endoxifen plasma levels will be measured. If the endoxifen level is below 30 or 40 nM, then 1 mg of oral (Z)-endoxifen will be added to the oral tamoxifen adjuvant regimen. Additional (Z)-endoxifen doses will be added until a stable endoxifen level of at least 40 nM but not more than 80 nM is achieved. The endpoint is to establish a therapeutically stable endoxifen level in the tamoxifen+endoxifen group for at least 6 months.

Example 17: Pre-Surgical Treatment of Estrogen Receptor Positive Breast Cancer by Oral Administration of Z-Endoxifen-D-Gluconate An objective is to determine if Z-Endoxifen-D-gluconate reduces tumor activity in pre-surgical estrogen receptor positive breast cancer patients. Upon the initial diagnosis of ER+ breast cancer, 8 patients will be assigned to one of 3 groups, where each patient will receive 1, 2, or 4 mg of (Z)-endoxifen-D-gluconate for 21 days prior to surgery.

The biomarker KI-67 levels of the tumor will be compared from the time of initial biopsy and the surgical sample will be compared to determine if one of the 3 doses results in a decrease in tumor activity.

Example 18: Therapeutic Treatment of Breast Cancer by Oral Administration of (Z)-Endoxifen D-Gluconate An objective of the study is to demonstrate that therapeutic (Z)-endoxifen levels in the subject's plasma can be achieved in tamoxifen-refractory patients initiating adjuvant breast cancer therapy. Plasma endoxifen levels will be used as a surrogate endpoint to predict clinical benefit as well as the rate of recurrence in this population and to confirm the safety and tolerability of oral (Z)-endoxifen D-gluconate administration when compared with tamoxifen.

Generally healthy subjects with estrogen receptor positive breast cancer for whom tamoxifen is indicated as part of their complete treatment regimen will be enrolled for the study for up to 6 months. At least seventy five tamoxifen-refractory breast cancer subjects will be enrolled in the study to ensure an evaluable population consists of at least 25 tamoxifen and 25 (Z)-endoxifen subjects is achieved. Additional subjects may be enrolled to achieve the desired population of tamoxifen-refractory subjects. These subjects will have been diagnosed with breast cancer and undergone mastectomy or lumpectomy.

Immediately after mastectomy or lumpectomy, 25 subjects will be assigned to the tamoxifen group and administered daily with oral 20 mg Tamoxifen for a period of 3 months. Additional 25 subjects will be assigned to the (Z)-endoxifen group and administered daily with oral 10 mg tablet of (Z)-endoxifen D-gluconate for a period of 3 months. Blood will be drawn from each subject at day 0 (baseline), and on days 7, 14, 21, 28, 60 and 90. Plasma (Z)-endoxifen levels, hematology, chemistry, and coagulation parameters will be taken for both treatment sets on day 0 (baseline measurement), as wells as on days 7, 14, 21, 28, 60 and 90.

The plasma (Z)-endoxifen levels of the two treatment sets will be compared to each other. If the plasma endoxifen levels of the tamoxifen treated subjects are less than 30 nM, then those subjects will be transferred to the (Z)-endoxifen therapy group and the treatment will continue for an additional 6 months. If the plasma endoxifen levels of the tamoxifen treated subjects are above 30 nM, they will continue to be treated with tamoxifen. Bloods samples will continue to be drawn weekly until the end of the study to monitor the subjects' plasma (Z)-endoxifen levels, hematology, chemistry, and coagulation parameters. Recurrence of cancer in the subjects will be monitored and compared between the treatment groups. Safety and efficacy will be evaluated every 3 months until the end of the study.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An oral formulation comprising an endoxifen composition encapsulated in an enteric capsule, wherein the endoxifen composition comprises a compound of Formula (III):

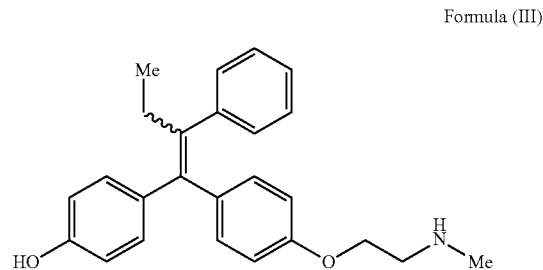 [SMILES: CCC(=C(c1ccc(O)cc1)c1ccc(OCCNC)cc1)c1ccccc1]

Formula (III)

wherein at least 90% by weight of the compound of Formula (III) is (Z)-endoxifen.

2. The oral formulation of claim 1, wherein the oral formulation is a delayed-release formulation.

3. The oral formulation of claim 1, wherein the enteric capsule is uncoated.

4. The oral formulation of claim 1, wherein the enteric capsule further comprises an enteric coating.

5. The oral formulation of claim 1, formulated such that the oral formulation is resistant to dissolution in an acidic environment for at least 2 hours, as measured in a dissolution test performed according to a method of USP 711.

6. The oral formulation of claim 1, formulated such that the oral formulation releases no more than 10% of the (Z)-endoxifen over 2 hours in gastric fluid, as measured in a dissolution test performed according to a method of USP 711.

7. The oral formulation of claim 1, formulated such that the oral formulation releases at least 50% of the (Z)-endoxifen within 8 hours in intestinal fluid, as measured in a dissolution test performed according to a method of USP 711.

8. The oral formulation of claim 1, wherein the enteric capsule comprises hydroxypropylmethyl cellulose.

9. The oral formulation of claim 1, wherein the endoxifen composition further comprises a filler.

10. The oral formulation of claim 9, wherein the filler comprises talc, calcium carbonate, a sugar, a salt, microcrystalline cellulose, methyl cellulose, carboxymethyl cellulose, kaolin, mannitol, silicic acid, sorbitol, starch, pregelatinized starch, or combinations thereof.

11. The oral formulation of claim 1, wherein the endoxifen composition further comprises a disintegrant.

12. The oral formulation of claim 1, wherein the endoxifen composition further comprises a lubricant.

13. The oral formulation of claim 12, wherein the lubricant comprises calcium stearate, magnesium stearate, zinc stearate, mineral oil, glycerin, sorbitol, mannitol, polyethylene glycol, stearic acid, sodium lauryl sulfate, talc, hydrogenated vegetable oil, ethyl oleate, ethyl laureate, agar, or combinations thereof.

14. The oral formulation of claim 1, wherein the endoxifen composition comprises from 0.01 mg to 200 mg (Z)-endoxifen per enteric capsule.

15. A method of delivering (Z)-endoxifen to a subject, the method comprising administering to the subject an oral formulation comprising an endoxifen composition encapsulated in an enteric capsule, wherein the endoxifen composition comprises a compound of Formula (III):

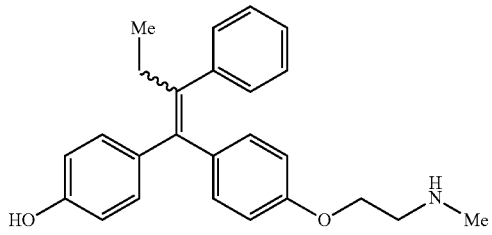

Formula (III)

wherein at least 90% by weight of the compound of Formula (III) is (Z)-endoxifen.

16. The method of claim 15, further comprising releasing no more than 10% of the (Z)-endoxifen in a stomach of the subject within 2 hours following administration.

17. The method of claim 15, further comprising releasing at least 50% of the (Z)-endoxifen in a small intestine of the subject within 8 hours following administration.

18. The method of claim 15, further comprising producing an area under curve ($AUC_{0-inf}$) of (Z)-endoxifen in the subject of from 200 hr*ng/mL to 10,000 hr*ng/mL per 4 mg of (Z)-endoxifen administered.

19. The method of claim 15, further comprising producing a maximum blood plasma concentration ($C_{max}$) of (Z)-endoxifen in the subject of from 14 ng/mL to 62 ng/mL per 4 mg of (Z)-endoxifen administered.

20. The method of claim 15, further comprising treating a hormone-dependent breast disorder or a hormone-dependent reproductive tract disorder in the subject.

21. The method of claim 20, wherein the hormone-dependent breast disorder or the hormone-dependent reproductive tract disorder is a benign breast disorder, hyperplasia, atypia, atypical ductal hyperplasia, atypical lobular hyperplasia, increased breast density, gynecomastia, ductal carcinoma in situ, lobular carcinoma in situ, breast cancer, precocious puberty, McCune-Albright Syndrome, endometrial cancer, ovarian cancer, uterine cancer, cervical cancer, vaginal cancer, or vulvar cancer.

22. The method of claim 20, wherein the hormone-dependent breast disorder or the hormone-dependent reproductive tract disorder is tamoxifen-refractory or tamoxifen resistant.

* * * * *

(12) POST-GRANT REVIEW CERTIFICATE (291st)
United States Patent
Sun et al.

(10) Number: US 11,572,334 J1
(45) Certificate Issued: Apr. 18, 2025

(54) METHODS FOR MAKING AND USING ENDOXIFEN

(71) Applicants: Yao-Lin Sun; ChangJung Wu; Steven C. Quay; LungHu Wang; ChuanDer Huang

(72) Inventors: Yao-Lin Sun; ChangJung Wu; Steven C. Quay; LungHu Wang; ChuanDer Huang

(73) Assignee: ATOSSA THERAPEUTICS, INC.

Trial Number:

PGR2023-00043 filed Aug. 18, 2023

Post-Grant Review Certificate for:

Patent No.: 11,572,334
Issued: Feb. 7, 2023
Appl. No.: 17/580,428
Filed: Jan. 20, 2022

The results of PGR2023-00043 are reflected in this post-grant review certificate under 35 U.S.C. 328(b).

POST-GRANT REVIEW CERTIFICATE
U.S. Patent 11,572,334 J1
Trial No. PGR2023-00043
Certificate Issued Apr. 18, 2025

AS A RESULT OF THE POST-GRANT REVIEW PROCEEDING, IT HAS BEEN DETERMINED THAT:

Claims 1-22 are cancelled.

\* \* \* \* \*